United States Patent
Steele et al.

(10) Patent No.: US 11,384,371 B2
(45) Date of Patent: Jul. 12, 2022

(54) HYDROXYLATION OF BRANCHED ALIPHATIC OR AROMATIC SUBSTRATES EMPLOYING THE AMYCOLATOPSIS LURIDA CYTOCHROME P450

(71) Applicant: HYPHA DISCOVERY LIMITED, Abingdon (GB)

(72) Inventors: Jonathan Charles Paul Steele, Uxbridge (GB); Antonio De Riso, Uxbridge (GB); Headley St Edward Williams, Ajax (CA); Richard Kerry Phipps, Uxbridge (GB); Stephen Keith Wrigley, Uxbridge (GB); Kinga Linda Nytko, Uxbridge (GB); Vincent Poon, Uxbridge (GB); Sebastian Schulz, Dresden (DE); John Maxim Ward, London (GB)

(73) Assignee: HYPHA DISCOVERY LIMITED, Abingdon (GB)

( * ) Notice: Subject to any disclaimer, the term of this patent is extended or adjusted under 35 U.S.C. 154(b) by 0 days.

(21) Appl. No.: 16/349,296

(22) PCT Filed: Nov. 15, 2017

(86) PCT No.: PCT/GB2017/053432
§ 371 (c)(1),
(2) Date: May 13, 2019

(87) PCT Pub. No.: WO2018/091885
PCT Pub. Date: May 24, 2018

(65) Prior Publication Data
US 2019/0367957 A1    Dec. 5, 2019

(30) Foreign Application Priority Data
Nov. 15, 2016 (GB) .................................... 1619344

(51) Int. Cl.
C12P 17/18 (2006.01)
C12P 7/42 (2006.01)
C12P 7/66 (2006.01)
C12P 17/16 (2006.01)

(52) U.S. Cl.
CPC ............. *C12P 17/182* (2013.01); *C12P 7/42* (2013.01); *C12P 7/66* (2013.01); *C12P 17/165* (2013.01); *C12P 17/167* (2013.01)

(58) Field of Classification Search
CPC .. C12P 7/66; C12P 17/167; C12P 7/42; C12P 17/182; C12P 17/165
See application file for complete search history.

(56) References Cited

U.S. PATENT DOCUMENTS 6,884,608 B2 * 4/2005 Basch .................... C07K 14/79
                                                                435/189
2014/0038850 A1   2/2014 Fasan et al.

FOREIGN PATENT DOCUMENTS

| WO | WO 2003/057830 | 7/2003 |
| WO | WO 2004/078978 | 9/2004 |
| WO | WO 2011/038313 | 3/2011 |
| WO | WO 2012/109586 | 8/2012 |
| WO | WO 2013/073775 | 5/2013 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Dennig A., Engineering of cytochrome P450 monooxygenases for application in phenol synthesis. Doctoral Thesis, 2013, pp. 1-222, Aachen University zur Erlangung, Germany. (Year: 2013).*
Devos et al., Practical limits of function prediction. Proteins: Structure, Function, and Genetics. 2000, vol. 41: 98-107. (Year: 2000).*
Lepri et al., Metabolism study and biological evaluation of bosentan derivative. Eur. J. Med. Chem., 2016, vol. 121: 658-670. (Year: 2016).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Adam et al., Biocatalytic hydroxylation of hydrocarbons with topsoil-microorganism *Bacillus megaterium*. J. Org. Chem., 2000, vol. 65: 878-882. (Year: 2000).*
Fasan et al., Tunung P450 enzymes as oxidation catalysts. ACS Catal., 2012, vol. 2: 647-666. (Year: 2012).*
Roper et al., Biocatalysis for organic chemists: Hydroxylations. Organic Synthesis Uding Biocatalysis, Elsevier Inc., 2016, Chapter 8 , pp. 213-241 (available online Sep. 11, 2015). (Year: 2016).*
Alkyl, https://en.wikipedia.org/wiki/Alkyl, 4 pages downloaded on Mar. 11, 2021. (Year: 2021).*
Le Gal., et al., Diversity of selective environmental substrates for human P450 2A6: alkoxyethers, nicotine, coumarin, N-nitrosodiethylamine, and N-nitrobenzylmethylamine. Toxicology Lett., 2003, vol. 144: 77-91. (Year: 2003).*
Mantyla et al., Synthesis and antileishmanial activity of novel buparvaquone oxime derivatives. Biorg. Med. Chem., 2004, vol. 12: 3497-3502. (Year: 2004).*
Nakamura et al., Coumarin substrates for cytochrome P450 2D6 flourescence assays. Anal. Biochem., 2001, vol. 292: 280-286. (Year: 2001).*

(Continued)

*Primary Examiner* — Ganapathirama Raghu
(74) *Attorney, Agent, or Firm* — Saliwanchik, Lloyd & Eisenschenk

(57) ABSTRACT

The use of a cytochrome P-450 enzyme comprising SEQ ID NO: 3, or a variant enzyme having at least 70% identity thereto and having CYP-450 activity, for the hydroxylation of an organic compound.

15 Claims, 33 Drawing Sheets

Specification includes a Sequence Listing.

(56) References Cited

OTHER PUBLICATIONS

Database UniProt [Online] Accession No. A0A093BCG8, May 11, 2016, XP-002777466.
Written Opinion in International Application No. PCT/GB2017/053432, dated Apr. 12, 2018, pp. 1-15.
Basch, J. and Chiang, S-J. "Cloning and expression of a cytochrome P450 hydroxylase gene from *Amycolatopsis orientalis*: hydroxylation of epothilone B for the production of epothilone F" *J Ind Microbiol Biotechnol*, 2007, 34:171-176.
Appleby, C.A. "A soluble haemoprotein P 450 from nitrogen-fixing Rhizobium bacteroids" *Biochim. Biophys. Acta.*, 1967, 147:399-402.
Broadbent, D.A. and Cartwright, N.J. "Bacterial attack on phenolic ethers electron acceptorsubstrate binding proteins in bacterial O-dealkylases: purification and characterization of cytochrome P450$_{npd}$ of *Nocardia*" *Microbios*, 1974, 9:119-130.
Danielson, P.B. "The Cytochrome P450 Superfamily: Biochemistry, Evolution and Drug Metabolism in Humans" *Current Drug Metabolism*, 2002, 3:561-597.
Hanukoglu, I. "Electron transfer proteins of cytochrome P450 systems" *Advances in Molecular and Cell Biology*, 1996, 14:29-56.
Hussain, H.A. and Ward, J.M. "Enhanced Heterologous Expression of Two Streptomyces griseolus Cytochrome P450s and *Streptomyces coelicolor* Ferredoxin Reductase as Potentially Efficient Hydroxylation Catalysts" *Applied and Environmental Microbiology*, 2003, 69(1):373-382.
Lamb, D.C. et al. "The First Virally Encoded Cytochrome P450" *J. Virology*, 2009, 83(16):8266-8269.
Narhi, L.O. and Fulco, A.J. "Characterization of a Catalytically Self-sufficient 119,000-Dalton Cytochrome P-450 Monooxygenase Induced by Barbiturates in *Bacillus megaterium*" *J. Biol. Chem.*, 1986, 261(16)7160-7169.
Sariaslani, F.S. and Kunz, D.A. "Induction of cytochrome P-450 in *Streptomyces griseus*" *Biochem and Biophys Research Communications*, 1986, 141(2):405-410.
Schwalb, H. et al. "Purification and characterization of pentobarbital-induced cytochrome P-450$_{BM-1}$ from *Bacillus megaterium* ATCC 14581 " *Biochimica et Biophysica Acta*, 1985, 838:302-311.
Shafiee, A. and Hutchinson, C.R. "Macrolide Antibiotic Biosynthesis: Isolation and Properties of Two Forms of 6-Deoxyerythronolide B Hydroxylase from *Saccharopolyspora erythraea (Streptomyces erythreus)*?" *Biochemistry*, 1987, 26:6204-6210.
Sigel, A et al. (Eds.), Metal Ions in Life Sciences, vol. 3, "The Ubiquitous Roles of Cytochrome P450 Proteins", 2007, John Wiley & Sons, Ltd.
Yu, C-A. and Gunsalus, I.C. "Cytochrome P-450$_{cam}$. I. Crystallization and properties" *J. Biol. Chem.*, 1974, 249(1):94-101.
Office Action dated Sep. 16, 2021, issued in Japanese Patent Application 2019-547195.

* cited by examiner

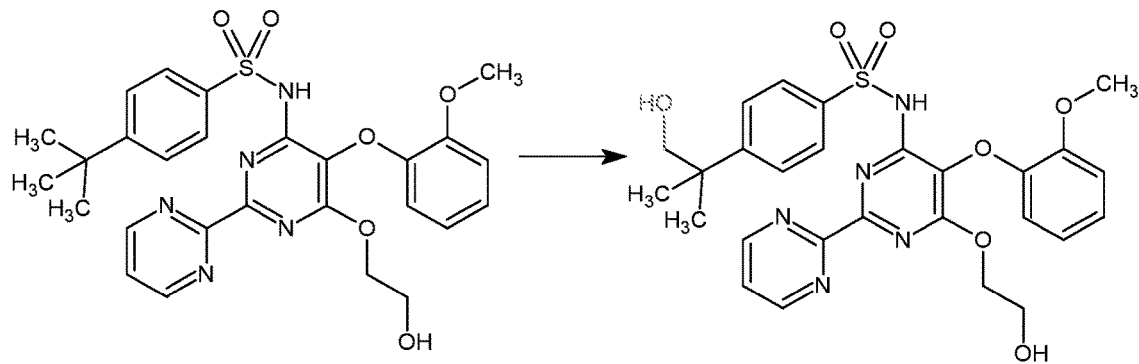
(a)
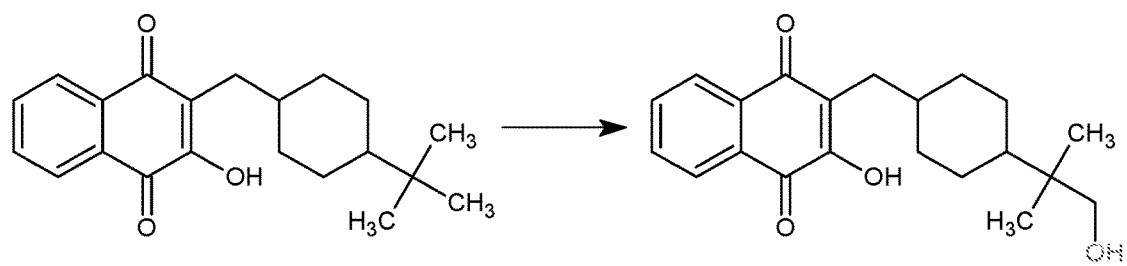
(b)
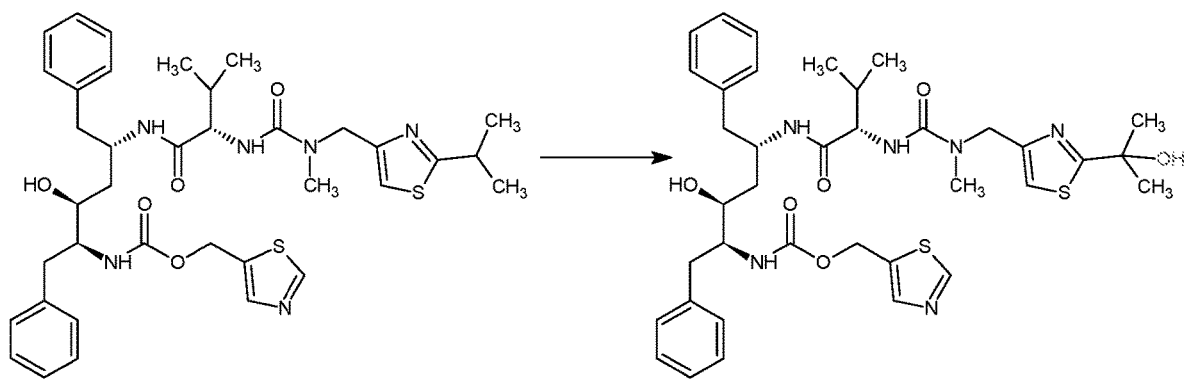
(c)
Figure 1a

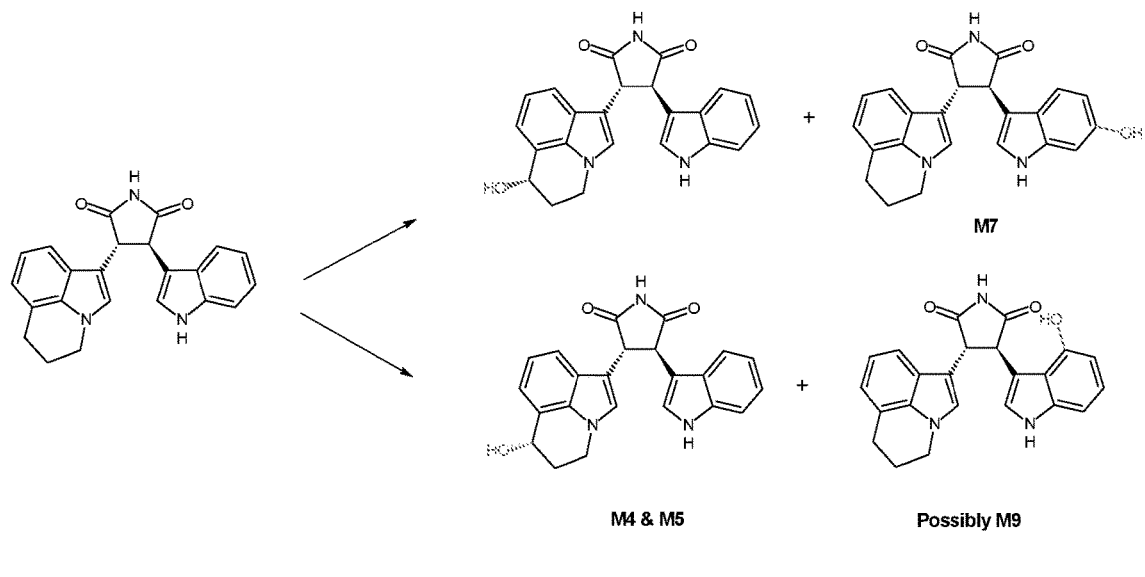
(d)
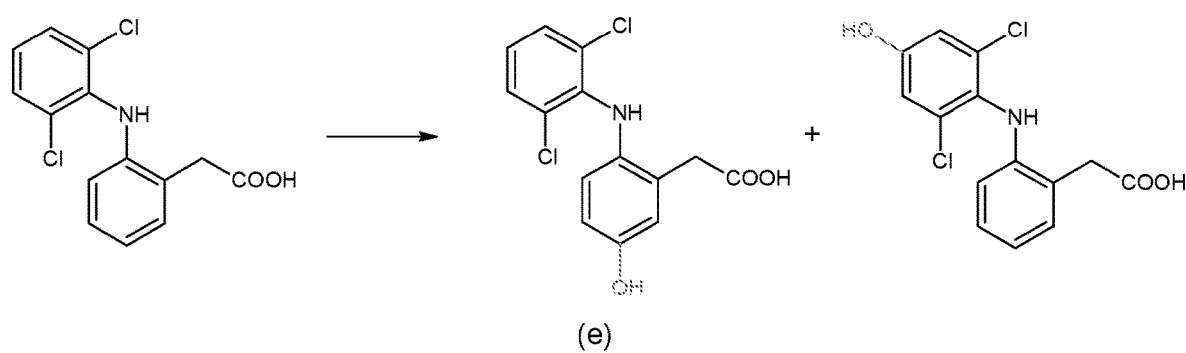
(e)
Figure 1b

SEQ ID NO: 1 aluC09-aluF03
P450 aluC09: BB31_01535
Ferredoxin aluF03: BB31_01530
Strand: both minus
Original sequence download (NCBI):  1418 bp
>gi|755908329|gb|CP007219.1|:290463-291880 Amycolatopsis lurida NRRL 2430, complete genome TTAAGCGAGCGACAAGGCCTGCCCCGGGCAGATGTGCACGGCGGTGCGGGCGTTTTCT
TCCGCCTCTTCG
CCTTCAGGCTCGGCGTTCAGCACGAGGACCGTTCCGTCGTCCTCGCTCTGATCGAACAG
ATCGGGATCGG
TGAGCACGCACTGGCCCGCGCCCACGCATTTCCCGGTGTCCGCGATGATCTTCATGGCT
CCTCCTACCAG
GTGACCGGAAGGGCGTGGAGGCCGTAGATCGTCGAATCGTGCTTGAACGGCAGTTCGT
CGACCGGAACGG
CGATCCGGAGGCCCGGCACTCGCCGGAACAACGTATCGAAGACGATCTGGAGTTCCAA
CCTCGCCAAGTT
CTGGCCGAGACACTGGTGCACCCCGAATCCGAACGCGACGTGATGCCGCGCGCCGCGT
TCGATGTCGAAG
GTGTCCGGGTTCTCGAAGCCGTCCGGATCGTGGTTGCCCGCGTTGCTCAGGCCCACCA
CCCCTTCCCCCG
CGCGGATCAGCGTTCCGCCGATCTCGACGTCCGCCGTGGCGAAGCGTGAGGTCGCCGT
TTCCGCGATCGT
GAAGACCCGCAGGAGTTCCTCGATGGCGGCGAGGGTCTTGCCGGGGTCTGCCTTGATC
TTCGCGAGCTGA
TCGGGATTCTCCAGCAGGGTCACCGTGCCGAGCGAGATCATGTTCGCCGTGGTCTCGTG
TCCGGCGATGA
GCAGCAGGAACGCCAGCCCGACGAGTTCACCGTGGTCGGCCTCGCCCGTTTCCCGCTG
TTTCAGGATCTG
ACGGCCGAGGAGGTCGTCCTCGGTGGCGTTCGCCTCCTTCTTGGTGACCAGTTCGTCGA
GATAGTTTTCG
AGCTGCTCGAACGCGGTCATCCGTTCTTCGGCGGTGACCTCCCGGCTGAGCATCCTGGA
ACTGCAGGACT
GGAAGAACTCGTGGTCCGAATAGGGGACGCCGAGCAGTTCGCAGATCACCAGCGAGGG
AACGGGCAGGGA
AAGCGCCTGGACGAGATCGGCGGGTTTGGGGCCCGCGAGCAGGGCGTCGAGATGTTC
GTCGACGATCTGC
TGAATTCGCGGCTGGAGCGCCTTCATCCGCTTGACGGTGAATTCCCCGACGACGTCACG
CCTGGCCCGGC
TGTGTTCCGGCGGATCCATCGCGATGAGGGAGGGGCGGAACGGCTTGTCCTCGCGGCG
GATCTGCCGCGC
GACCATCAGCGGGAACGACGGGCTCTGCCGGTCGGAACTGAAATGCGGGCTGCTCAGC
ATTTCGCGGATG
TCTTCGAGCCGGGTGAGCGCCCAAGCCGTTTGACCGGACGGGAGACCGACCCGGGAAA
CCGGACTTTCCC
GGCGAAGCCGTTCGTATTCGGGCGGCGGCGAAAACGGGCATTTCCGGGCCAGCGGCAA
GGTCGCGGTGGT
TTCCTCGACGTCAGTCAT

SEQ ID NO: 2

Reverse complement of original sequence download (NCBI): 1418 bp
>gi|755908329|gb|CP007219.1|:290463-291880 Amycolatopsis lurida NRRL 2430, complete genome REVERSE COMPLEMENT

Figure 2a

*ATG*ACTGACGTCGAGGAAACCACCGCGACCTTGCCGCTGGCCCGGAAATGCCCGTTTTCG
CCGCCGCCCGAATACGAACGGCTTCGCCGGGAAAGTCCGGTTTCCCGGGTCGGTCTCCC
GTCCGGTCAAACGGCTTGGGCGCTCACCCGGCTCGAAGACATCCGCGAAATGCTGAGCA
GCCCGCATTTCAGTTCCGACCGGCAGAGCCCGTCGTTCCCGCTGATGGTCGCGCGGCAG
ATCCGCCGCGAGGACAAGCCGTTCCGCCCCTCCCTCATCGCGATGGATCCGCCGGAACA
CAGCCGGGCCAGGCGTGACGTCGTCGGGGAATTCACCGTCAAGCGGATGAAGGCGCTCC
AGCCGCGAATTCAGCAGATCGTCGACGAACATCTCGACGCCCTGCTCGCGGGCCCCAAAC
CCGCCGATCTCGTCCAGGCGCTTTCCCTGCCCGTTCCCTCGCTGGTGATCTGCGAACTGC
TCGGCGTCCCCTATTCGGACCACGAGTTCTTCCAGTCCTGCAGTTCCAGGATGCTCAGCC
GGGAGGTCACCGCCGAAGAACGGATGACCGCGTTCGAGCAGCTCGAAAACTATCTCGAC
GAACTGGTCACCAAGAAGGAGGCGAACGCCACCGAGGACGACCTCCTCGGCCGTCAGAT
CCTGAAACAGCGGGAAACGGGCGAGGCCGACCACGGTGAACTCGTCGGGCTGGCGTTCC
TGCTGCTCATCGCCGGACACGAGACCACGGCGAACATGATCTCGCTCGGCACGGTGACC
CTGCTGGAGAATCCCGATCAGCTCGCGAAGATCAAGGCAGACCCCGGCAAGACCCTCGC
CGCCATCGAGGAACTCCTGCGGGTCTTCACGATCGCGGAAACGGCGACCTCACGCTTCG
CCACGGCGGACGTCGAGATCGGCGGAACGCTGATCCGCGCGGGGAAGGGGTGGTGGG
CCTGAGCAACGCGGGCAACCACGATCCGGACGGCTTCGAGAACCCGGACACCTTCGACA
TCGAACGCGGCGCGCGGCATCACGTCGCGTTCGGATTCGGGGTGCACCAGTGTCTCGGC
CAGAACTTGGCGAGGTTGGAACTCCAGATCGTCTTCGATACGTTGTTCCGGCGAGTGCCG
GGCCTCCGGATCGCCGTTCCGGTCGACGAACTGCCGTTCAAGCACGATTCGACGATCTAC
GGCCTCCACGCCCTTCCGGTCACCTGG*TAG*GAGGAGCCATGAAGATCATCGCGGACACC
GGGAAATGCGTGGGCGCGGGCCAGTGCGTGCTCACCGATCCCGATCTGTTCGATCAGAG
CGAGGACGACGGAACGGTCCTCGTGCTGAACGCCGAGCCTGAAGGCGAAGAGGCGGAA
GAAAACGCCCGCACCGCCGTGCACATCTGCCCGGGGCAGGCCTTGTCGCTCGCTTAA

*P450 (italics)*
Ferredoxin
Start and stop codons in bold

Protein sequences
(translated using Expasy from DNA sequences above)

SEQ ID NO: 3 (amino acid sequence of AluC09 (404 aa))
MTDVEETTATLPLARKCPFSPPPEYERLRRESPVSRVGLPSGQTAWALTRLEDIREMLSS
PHFSSDRQSPSFPLMVARQIRREDKPFRPSLIAMDPPEHSRARRDVVGEFTVKRMKALQP
RIQQIVDEHLDALLAGPKPADLVQALSLPVPSLVICELLGVPYSDHEFFQSCSSRMLSRE
VTAEERMTAFEQLENYLDELVTKKEANATEDDLLGRQILKQRETGEADHGELVGLAFLLL
IAGHETTANMISLGTVTLLENPDQLAKIKADPGKTLAAIEELLRVFTIAETATSRFATAD
VEIGGTLIRAGEGVVGLSNAGNHDPDGFENPDTFDIERGARHHVAFGFGVHQCLGQNLAR
LELQIVFDTLFRRVPGLRIAVPVDELPFKHDSTIYGLHALPVTW SEQ ID NO: 4 (amino acid sequence of AluF03 (64 aa))
MKIIADTGKCVGAGQCVLTDPDLFDQSEDDGTVLVLNAEPEGEEAEENARTAVHICPGQA
LSLA SEQ ID NO: 9 (synthetic DNA of ferredoxin$_{fd1}$ and ferredoxin reductase$_{SCF15A}$
subcloned into pD454-SR plasmid via *NdeI* and *NotI* by DNA2.0)
ATGTCTCATATGGGCGGCGAATTCATGACCATGCGGGTGAGTGCGGATCGGA
CGGTCTGCGTCGGTGCCGGGCTGTGTGCGCTGACGGCGCCGGGCGTCTTCG
ACCAGGACGACGACGGGATCGTCACGGTGCTGACGGCCGAACCCGCCGCCG
ACGACGACCGGCGCACCGCGCGCGAGGCCGGCCATCTCTGTCCGTCCGGTG
CGGTCCGCGTCGTCGAGGACACGGAATAATAGGAAGCTT*ATG*CCCCGCCCTC
TGCGGGTAGCCATCGTCGGATCCGGCCCGGCCGGGATCTACGCCGCCGACG
CCCTGCTCAAGTCCGAAGTGGCCGCCGACCCCGGTGT

Figure 2b

*TTCCATCGACATCTTCGAGCGCATGCCCGCCCCGTTCGGCCTCATCCGGTAC*
*GGCGTCGCGCCCGACCACCCGCGGATCAAGGGCATCATCACGGCCCTCCAC*
*CAGGTGCTCGACAAGCCGCAGATCCGCCTCTTCGGCAACGTGAACTACCCCA*
*CCGACGTCAGCCTGGACGATCTGCGCGCCTTCTACGACGGTGTGATCTTCGC*
*CACCGGCGCCACGGCGGACCGGGACCTGTCCCTCCCGGGCATCGACCTCGA*
*CGGCTCGTACGGCGCGGCCGACTTCGTCGCCTGGTACGACGGCCACCCCGA*
*CTTCCCGCGCACCTGGCCGCTGGAGGCGGAGAAAGTCGCCGTCCTCGGTGT*
*CGGCAACGTCGCCCTGGACATCGCGCGCGTCCTCGCCAAGACGGCCGACGA*
*GCTGCTGCCGACCGAGATCCCGCCGAACGTCTACGAGGGCCTCAAGGCCAA*
*CAAGGCGCTGGAGGTGCACGTCTTCGGCCGCCGCGGCCCGGCGCAGGCGA*
*AGTTCAGCCCGATGGAGCTGCGGGAGCTGGACCACTCCCCAACATCGAGGT*
*GATCGTCGACCCCGAGGACATCGACTACGACGAGGGCTCGATCGCGACCCG*
*GCGCGGCAACAAGCAGGCCGACATGGTCGCCAAGACCCTGGAGAACTGGGC*
*GATCCGCGACGTCGGCGACCGGCCGCACAAGCTGTTCCTGCACTTCTTCGAG*
*TCGCCCGCGGAGATCCTCGGCGAGGACGGCAGGGTGACCGGCCTGCGCAC*
*CGAGCGCACGGAGCTGGACGGCACGGGCAACGTCAAGGGCACCGGCGAGTT*
*CAAGGACTGGGACGTCCAGGCGGTCTACCGGGCCGTCGGCTACCTCTCCGA*
*CCAGCTGCCCAAGCTGCCCTGGGACCTCGAGACGGGCACGGTCCCGGACGC*
*GGGCGGCCGGGTCGTCCAGGAGTCCGGCGAGCACCTCCAGTCGACGTACGT*
*CACCGGCTGGATCCGGCGCGGTCCGATCGGCCTGATCGGCCACACCAAGGG*
*CGACGCCAACGAGACGGTGTCCAACCTGCTGGACGACTACGCGAACGGCCG*
*TCTCCAGACGCCCTCCTCCCCCGCTCCCGAGGCCGTGGACGCGTTCCTCGC*
*CGAGCGGAACGTCCGCTTCACCACCTGGGACGGCTGGTACCGGCTCGACGC*
*CGCGGAGAAGGCGCAGGGCGAACCGCACGGGCGTGAGCGCGTGAAGTACG*
*TCGAGCGCGAGGACATGCTCCGCGAGAGCGGCGCCTAATGAGCGGCCGC*

*Ferredoxin reductase* (italics)
<u>Ferredoxin (underlined)</u>
Start and stop codons in bold

Protein sequences
(translated using Expasy from DNA sequences above)

<u>SEQ ID NO: 10</u> (amino acid sequence of ferredoxin$_{Fd1}$ (69 aa))
MTMRVSADRTVCVGAGLCALTAPGVFDQDDDGIVTVLTAEPAADDDRRTAREAGHLCPSGAVRVVEDTE <u>SEQ ID NO: 11</u> (amino acid sequence of ferredoxin reductase$_{SCF15A}$ (454 aa))
MPRPLRVAIVGSGPAGIYAADALLKSEVAADPGVSIDIFERMPAPFGLIRYGVAPD
HPRIKGIITALHQVLDKPQIRLFGNVNYPTDVSLDDLRAFYDGVIFATGATADRDLS
LPGIDLDGSYGAADFVAWYDGHPDFPRTWPLEAEKVAVLGVGNVALDIARVLAKT
ADELLPTEIPPNVYEGLKANKALEVHVFGRRGPAQAKFSPMELRELDHSPNIEVIV
DPEDIDYDEGSIATRRGNKQADMVAKTLENWAIRDVGDRPHKLFLHFFESPAEILG
EDGRVTGLRTERTELDGTGNVKGTGEFKDWDVQAVYRAVGYLSDQLPKLPWDL
ETGTVPDAGGRVVQESGEHLQSTYVTGWIRRGPIGLIGHTKGDANETVSNLLDDY
ANGRLQTPSSPAPEAVDAFLAERNVRFTTWDGWYRLDAAEKAQGEPHGRERVK
YVEREDMLRESGA <u>Figure 2c</u>

SEQ ID NO: 14 (Coding sequence of ferredoxin reductase$_{camA}$ and ferredoxin$_{camB}$)

*ATGAACGCAAACGACAACGTGGTCATCGTCGGTACCGGACTGGCTGGCGTTG*
*AGGTCGCCTTCGGCCTGCGCGCCAGCGGCTGGGAAGGCAATATCCGGTTGG*
*TGGGGGATGCGACGGTAATTCCCCATCACCTACCACCGCTATCCAAAGCTTAC*
*TTGGCCGGCAAAGCCACAGCGGAAAGCCTGTACCTGAGAACCCCAGATGCCT*
*ATGCAGCGCAGAACATCCAACTACTCGGAGGCACACAGGTAACGGCTATCAA*
*CCGCGACCGACAGCAAGTAATCCTATCGGATGGCCGGGCACTGGATTACGAC*
*CGGCTGGTATTGGCTACCGGAGGGCGTCCAAGACCCCTACCGGTGGCCAGT*
*GGCGCAGTTGGAAAGGCGAACAACTTTCGATACCTGCGCACACTCGAGGACG*
*CCGAGTGCATTCGCCGGCAGCTGATTGCGGATAACCGTCTGGTGGTGATTGG*
*TGGCGGCTACATTGGCCTTGAAGTGGCTGCCACCGCCATCAAGGCGAACATG*
*CACGTCACCCTGCTTGATACGGCAGCCCGGGTTCTGGAGCGGGTTACCGCCC*
*CGCCGGTATCGGCCTTTTACGAGCACCTACACCGCGAAGCCGGCGTTGACAT*
*ACGAACCGGCACGCAGGTGTGCGGGTTCGAGATGTCGACCGACCAACAGAA*
*GGTTACCGCCGTCCTCGCGAGGACGGCACAAGGCTGCCAGCGGATCTGGT*
*AATCGCCGGGATTGGCCTGATACCAAACTGCGAGTTGGCCAGTGCGGCCGG*
*CCTGCAGGTTGATAACGGCATCGTGATCAACGAACACATGCAGACCTCTGATC*
*CCTTGATCATGGCCGTCGGCGACTGTGCCCGATTTCACAGTCAGCTCTATGAC*
*CGCTGGGTGCGTATCGAATCGGTGCCCAATGCCTTGGAGCAGGCACGAAAGA*
*TCGCCGCCATCCTCTGTGGCAAGGTGCCACGCGATGAGGCGGCGCCCTGGT*
*TCTGGTCCGATCAGTATGAGATCGGATTGAAGATGGTCGGACTGTCCGAAGG*
*GTACGACCGGATCATTGTCCGCGGCTCTTTGGCGCAACCCGACTTCAGCGTT*
*TTCTACCTGCAGGGAGACCGGGTATTGGCGGTCGATACAGTGAACCGTCCAG*
*TGGAGTTCAACCAGTCAAAACAAATAATCACGGATCGTTTGCCGGTTGAACCA*
*AACCTACTCGGTGACGAAAGCGTGCCGTTAAAGGAAATCATCGCCGCCGCCA*
*AAGCTGAACTGAGTAGTGCCTGAAATCTATACCCACAATAAATCACCGTTTTG*
CCCCATAGCGTGTGAGGATAAACAG<u>ATGCTAAAGTAGTGTATGTGTCACATG</u>
<u>ATGGAACGCGTCGCGAACTGGATGTGGCGGATGGCGTCAGCCTGATGCAGG</u>
<u>CTGCAGTCTCCAATGGTATCTACGATATTGTCGGTGATTGTGGCGGCAGCGC</u>
<u>CAGCTGTGCCACCTGCCATGTCTATGTGAACGAAGCGTTCACGGACAAGGTG</u>
<u>CCCGCCGCCAACGAGCGGGAAATCGGCATGCTGGAGTGCGTCACGGCCGAA</u>
<u>CTGAAGCCGAACAGCAGGCTCTGCTGCCAGATCATCATGACGCCCGAGCTGG</u>
<u>ATGGCATCGTGGTCGATGTTCCCGATAGGCAATGGTAA</u>

*Ferredoxin reductase* (italics)
<u>Ferredoxin (underlined)</u>
Start and stop codons in bold

Figure 2d

Protein sequences
(translated using Expasy from DNA sequences above)

SEQ ID NO: 15 (amino acid sequence of CamA (422 aa))
MNANDNVVIVGTGLAGVEVAFGLRASGWEGNIRLVGDATVIPHHLPPLSKAYLAG
KATAESLYLRTPDAYAAQNIQLLGGTQVTAINRDRQQVILSDGRALDYDRLVLATG
GRPRPLPVASGAVGKANNFRYLRTLEDAECIRRQLIADNRLVVIGGGYIGLEVAAT
AIKANMHVTLLDTAARVLERVTAPPVSAFYEHLHREAGVDIRTGTQVCGFEMSTD
QQKVTAVLCEDGTRLPADLVIAGIGLIPNCELASAAGLQVDNGIVINEHMQTSDPLI
MAVGDCARFHSQLYDRWVRIESVPNALEQARKIAAILCGKVPRDEAAPWFWSDQ
YEIGLKMVGLSEGYDRIIVRGSLAQPDFSVFYLQGDRVLAVDTVNRPVEFNQSKQI
ITDRLPVEPNLLGDESVPLKEIIAAAKAELSSA SEQ ID NO: 16 (amino acid sequence of CamB (107 aa))
MSKVVYVSHDGTRRELDVADGVSLMQAAVSNGIYDIVGDCGGSASCATCHVYVN
EAFTDKVPAANEREIGMLECVTAELKPNSRLCCQIIMTPELDGIVVDVPDRQW SEQ ID NO: 23 (synthetic DNA of truncated P450$_{BM3}$ subcloned into pET29a
plasmid via *Ndel* and *Notl* by Genscript)
CATATGATAATACGCCGGCGGCAGCGGCGGCAGCATTCCTTCACCTAGCACT
GAACAGTCTGCTAAAAAAGTACGCAAAAAGGCAGAAAACGCTCATAATACGCC
GCTGCTTGTGCTATACGGTTCAAATATGGGAACAGCTGAAGGAACGGCGCGT
GATTTAGCAGATATTGCAATGAGCAAAGGATTTGCACCGCAGGTCGCAACGCT
TGATTCACACGCCGGAAATCTTCCGCGCGAAGGAGCTGTATTAATTGTAACGG
CGTCTTATAACGGTCATCCGCCTGATAACGCAAAGCAATTTGTCGACTGGTTA
GACCAAGCGTCTGCTGATGAAGTAAAAGGCGTTCGCTACTCCGTATTTGGATG
CGGCGATAAAAACTGGGCTACTACGTATCAAAAAGTGCCTGCTTTTATCGATG
AAACGCTTGCCGCTAAAGGGGCAGAAAACATCGCTGACCGCGGTGAAGCAGA
TGCAAGCGACGACTTTGAAGGCACATACGAAGAATGGCGTGAACACATGTGG
AGTGACGTAGCAGCCTACTTTAACCTCGACATTGAAAACAGTGAAGATAATAA
ATCTACTCTTTCACTTCAATTTGTCGACAGCGCCGCGGATATGCCGCTTGCGA
AAATGCACGGTGCGTTTTCAACGAACGTCGTAGCAAGCAAAGAACTTCAACAG
CCAGGCAGTGCACGAAGCACGCGACATCTTGAAATTGAACTTCCAAAAGAAG
CTTCTTATCAAGAAGGAGATCATTTAGGTGTTATTCCTCGCAACTATGAAGGAA
TAGTAAACCGTGTAACAGCAAGGTTCGGCCTAGATGCATCACAGCAAATCCGT
CTGGAAGCAGAAGAAGAAAATTAGCTCATTTGCCACTCGCTAAAACAGTATC
CGTAGAAGAGCTTCTGCAATACGTGGAGCTTCAAGATCCTGTTACGCGCACG
CAGCTTCGCGCAATGGCTGCTAAAACGGTCTGCCCGCCGCATAAAGTAGAGC
TTGAAGCCTTGCTTGAAAAGCAAGCCTACAAAGAACAAGTGCTGGCAAAACGT
TTAACAATGCTTGAACTGCTTGAAAATACCCGGCGTGTGAAATGAAATTCAG
CGAATTTATCGCCCTTCTGCCAAGCATACGCCCGCGCTATTACTCGATTTCTT
CATCACCTCGTGTCGATGAAAACAAGCAAGCATCACGGTCAGCGTTGTCTCA
GGAGAAGCGTGGAGCGGATATGGAGAATATAAAGGAATTGCGTCGAACTATC
TTGCCGAGCTGCAAGAAGGAGATACGATTACGTGCTTTATTTCCACACCGCAG
TCAGAATTTACGCTGCCAAAAGACCCTGAAACGCCGCTTATCATGGTCGGACC
GGGAACAGGCGTCGCGCCGTTTAGAGGCTTTGTGCAGGCGCGCAAACAGCT
AAAAGAACAAGGACAGTCACTTGGAGAAGCACATTTATACTTCGGCTGCCGTT
CA

Figure 2e

CCTCATGAAGACTATCTGTATCAAGAAGAGCTTGAAAACGCCCAAAGCGAAGG
CATCATTACGCTTCATACCGCTTTTCTCGCATGCCAAATCAGCCGAAAACATA
CGTTCAGCACGTAATGGAACAAGACGGCAAGAAATTGATTGAACTTCTTGATC
AAGGAGCGCACTTCTATATTTGCGGAGACGGAAGCCAAATGGCACCTGCCGT
TGAAGCAACGCTTATGAAAGCTATGCTGACGTTCACCAAGTGAGTGAAGCAG
ACGCTCGCTTATGGCTGCAGCAGCTAGAAGAAAAAGGCCGATACGCAAAAGA
CGTGTGGGCTGGGTAATGAGCGGCCGC

Stop codons in bold
Protein sequences
(translated using Expasy from DNA sequences above)

SEQ ID NO: 24 (amino acid sequence of truncated P450 BM3 (596 aa))
GSGGSIPSPSTEQSAKKVRKKAENAHNTPLLVLYGSNMGTAEGTARDLADIAMSK
GFAPQVATLDSHAGNLPREGAVLIVTASYNGHPPDNAKQFVDWLDQASADEVKG
VRYSVFGCGDKNWATTYQKVPAFIDETLAAKGAENIADRGEADASDDFEGTYEE
WREHMWSDVAAYFNLDIENSEDNKSTLSLQFVDSAADMPLAKMHGAFSTNVVAS
KELQQPGSARSTRHLEIELPKEASYQEGDHLGVIPRNYEGIVNRVTARFGLDASQ
QIRLEAEEEKLAHLPLAKTVSVEELLQYVELQDPVTRTQLRAMAAKTVCPPHKVEL
EALLEKQAYKEQVLAKRLTMLELLEKYPACEMKFSEFIALLPSIRPRYYSISSSPRV
DEKQASITVSVVSGEAWSGYGEYKGIASNYLAELQEGDTITCFISTPQSEFTLPKD
PETPLIMVGPGTGVAPFRGFVQARKQLKEQGQSLGEAHLYFGCRSPHEDYLYQE
ELENAQSEGIITLHTAFSRMPNQPKTYVQHVMEQDGKKLIELLDQGAHFYICGDGS
QMAPAVEATLMKSYADVHQVSEADARLWLQQLEEKGRYAKDVWAG SEQ ID NO: 25 (amino acid sequence of P450$_{aluC09\_BM3}$ fusion protein)

ATGACTGACGTCGAGGAAACCACCGCGACCTTGCCGCTGGCCCGGAAATGC
CCGTTTTCGCCGCCGCCCGAATACGAACGGCTTCGCCGGGAAAGTCCGGTTT
CCCGGGTCGGTCTCCCGTCCGGTCAAACGGCTTGGGCGCTCACCCGGCTCG
AAGACATCCGCGAAATGCTGAGCAGCCCGCATTTCAGTTCCGACCGGCAGAG
CCCGTCGTTCCCGCTGATGGTCGCGCGGCAGATCCGCCGCGAGGACAAGCC
GTTCCGCCCCTCCCTCATCGCGATGGATCCGCCGGAACACAGCCGGGCCAG
GCGTGACGTCGTCGGGGAATTCACCGTCAAGCGGATGAAGGCGCTCCAGCC
GCGAATTCAGCAGATCGTCGACGAACATCTCGACGCCCTGCTCGCGGGCCCC
AAACCCGCCGATCTCGTCCAGGCGCTTTCCCTGCCCGTTCCCTCGCTGGTGA
TCTGCGAACTGCTCGGCGTCCCCTATTCGGACCACGAGTTCTTCCAGTCCTG
CAGTTCCAGGATGCTCAGCCGGGAGGTCACCGCCGAAGAACGGATGACCGC
GTTCGAGCAGCTCGAAAACTATCTCGACGAACTGGTCACCAAGAAGGAGGCG
AACGCCACCGAGGACGACCTCCTCGGCCGTCAGATCCTGAAACAGCGGGAAA
CGGGCGAGGCCGACCACGGTGAACTCGTCGGGCTGGCGTTCCTGCTGCTCA
TCGCCGGACACGAGACCACGGCGAACATGATCTCGCTCGGCACGGTGACCC
TGCTGGAGAATCCCGATCAGCTCGCGAAGATCAAGGCAGACCCCGGCAAGAC
CCTCGCCGCCATCGAGGAACTCCTGCGGGTCTTCACGATCGCGGAAACGGC
GACCTCACGCTTCGCCACGGCGGACGTCGAGATCGGCGGAACGCTGATCCG
CGCGGGGGAAGGGGTGGTGGGCCTGAGCAACGCGGGCAACCACGATCCGG
ACGGCTTCGAGAACCCGGACACCTTCGACATCGAACGCGGCGCGCGGCATC
ACGTCGCGTTCGGATTCGGGGTGCACCAGTGTCTCGGCCAGAACTTGGCGAG
GTTGGAACTCCAGATCGTCTTCGATACGTTGTTCCGGCGAGTGCCGGGCCTC
CGGATCGCCGTTCC

Figure 2f

```
GGTCGACGAACTGCCGTTCAAGCACGATTCGACGATCTACGGCCTCCACGCC
CTTCCGGTCACCTGGGGCGGCAGCGGCGGCAGCGGCGGCAGCATTCCTTCA
CCTAGCACTGAACAGTCTGCTAAAAAAGTACGCAAAAAGGCAGAAAACGCTCA
TAATACGCCGCTGCTTGTGCTATACGGTTCAAATATGGGAACAGCTGAAGGAA
CGGCGCGTGATTTAGCAGATATTGCAATGAGCAAAGGATTTGCACCGCAGGT
CGCAACGCTTGATTCACACGCCGGAAATCTTCCGCGCGAAGGAGCTGTATTA
ATTGTAACGGCGTCTTATAACGGTCATCCGCCTGATAACGCAAAGCAATTTGT
CGACTGGTTAGACCAAGCGTCTGCTGATGAAGTAAAAGGCGTTCGCTACTCC
GTATTTGGATGCGGCGATAAAAACTGGGCTACTACGTATCAAAAAGTGCCTGC
TTTTATCGATGAAACGCTTGCCGCTAAAGGGGCAGAAAACATCGCTGACCGC
GGTGAAGCAGATGCAAGCGACGACTTTGAAGGCACATACGAAGAATGGCGTG
AACACATGTGGAGTGACGTAGCAGCCTACTTTAACCTCGACATTGAAAACAGT
GAAGATAATAAATCTACTCTTTCACTTCAATTTGTCGACAGCGCCGCGGATATG
CCGCTTGCGAAAATGCACGGTGCGTTTTCAACGAACGTCGTAGCAAGCAAAG
AACTTCAACAGCCAGGCAGTGCACGAAGCACGCGACATCTTGAAATTGAACTT
CCAAAAGAAGCTTCTTATCAAGAAGGAGATCATTTAGGTGTTATTCCTCGCAAC
TATGAAGGAATAGTAAACCGTGTAACAGCAAGGTTCGGCCTAGATGCATCACA
GCAAATCCGTCTGGAAGCAGAAGAAGAAAAATTAGCTCATTTGCCACTCGCTA
AAACAGTATCCGTAGAAGAGCTTCTGCAATACGTGGAGCTTCAAGATCCTGTT
ACGCGCACGCAGCTTCGCGCAATGGCTGCTAAAACGGTCTGCCCGCCGCATA
AAGTAGAGCTTGAAGCCTTGCTTGAAAAGCAAGCCTACAAAGAACAAGTGCTG
GCAAAACGTTTAACAATGCTTGAACTGCTTGAAAAATACCCGGCGTGTGAAAT
GAAATTCAGCGAATTTATCGCCCTTCTGCCAAGCATACGCCCGCGCTATTACT
CGATTTCTTCATCACCTCGTGTCGATGAAAAACAAGCAAGCATCACGGTCAGC
GTTGTCTCAGGAGAAGCGTGGAGCGGATATGGAGAATATAAAGGAATTGCGT
CGAACTATCTTGCCGAGCTGCAAGAAGGAGATACGATTACGTGCTTTATTTCC
ACACCGCAGTCAGAATTTACGCTGCCAAAAGACCCTGAAACGCCGCTTATCAT
GGTCGGACCGGGAACAGGCGTCGCGCCGTTTAGAGGCTTTGTGCAGGCGCG
CAAACAGCTAAAAGAACAAGGACAGTCACTTGGAGAAGCACATTTATACTTCG
GCTGCCGTTCACCTCATGAAGACTATCTGTATCAAGAAGAGCTTGAAAACGCC
CAAAGCGAAGGCATCATTACGCTTCATACCGCTTTTTCTCGCATGCCAAATCA
GCCGAAAACATACGTTCAGCACGTAATGGAACAAGACGGCAAGAAATTGATTG
AACTTCTTGATCAAGGAGCGCACTTCTATATTTGCGGAGACGGAAGCCAAATG
GCACCTGCCGTTGAAGCAACGCTTATGAAAAGCTATGCTGACGTTCACCAAGT
GAGTGAAGCAGACGCTCGCTTATGGCTGCAGCAGCTAGAAGAAAAAGGCCGA
TACGCAAAAGACGTGTGGGCTGGGTAA
```

Start & Stop codons in bold
Protein sequences
(translated using Expasy from DNA sequences above)

SEQ ID NO: 26 (amino acid sequence of AluC09_BM3 (1004 aa))
MTDVEETTATLPLARKCPFSPPPEYERLRRESPVSRVGLPSGQTAWALTRLEDIR
EMLSSPHFSSDRQSPSFPLMVARQIRREDKPFRPSLIAMDPPEHSRARRDVVGEF
TVKRMKALQPRIQQIVDEHLDALLAGPKPADLVQALSLPVPSLVICELLGVPYSDH
EFFQSCSSRMLSREVTAEERMTAFEQLENYLDELVTKKEANATEDDLLGRQILKQ
RETGEADHGELVGLAFLLLIAGHETTANMISLGTVTLLENPDQLAKIKADPGKTLAA
IEELLRVFTIAETATSRFATADVEIGGTLIRAGEGVVGLSNAGNHDPDGFENPDTFD
IERGARHHVAFGFGVHQCLGQNLARLELQIVFDTLFRRVPGLRIAVPVDELPFKHD
STIYGLHALPVTWGGSGGSGGSIPSPSTEQSAKKVRKKA

Figure 2g

ENAHNTPLLVLYGSNMGTAEGTARDLADIAMSKGFAPQVATLDSHAGNLPREGA
VLIVTASYNGHPPDNAKQFVDWLDQASADEVKGVRYSVFGCGDKNWATTYQKV
PAFIDETLAAKGAENIADRGEADASDDFEGTYEEWREHMWSDVAAYFNLDIENSE
DNKSTLSLQFVDSAADMPLAKMHGAFSTNVVASKELQQPGSARSTRHLEIELPKE
ASYQEGDHLGVIPRNYEGIVNRVTARFGLDASQQIRLEAEEEKLAHLPLAKTVSVE
ELLQYVELQDPVTRTQLRAMAAKTVCPPHKVELEALLEKQAYKEQVLAKRLTMLE
LLEKYPACEMKFSEFIALLPSIRPRYYSISSSPRVDEKQASITVSVVSGEAWSGYG
EYKGIASNYLAELQEGDTITCFISTPQSEFTLPKDPETPLIMVGPGTGVAPFRGFVQ
ARKQLKEQGQSLGEAHLYFGCRSPHEDYLYQEELENAQSEGIITLHTAFSRMPNQ
PKTYVQHVMEQDGKKLIELLDQGAHFYICGDGSQ
MAPAVEATLMKSYADVHQVSEADARLWLQQLEEKGRYAKDVWAG

Figure 2h

Chromatograms of post-reaction extract using lyophilised material of recombinant P450$_{aluC09}$, ferredoxin$_{aluF03}$ and ferredoxin reductase$_{SCF15A}$ as described in Example 7 dosed with 100mg/L bosentan. Top to bottom is UV$_{268nm}$, EIC$_{552m/z}$ (bosentan (1.75 mins)) and EIC$_{568m/z}$ (hydroxy-bosentan (1.43 mins, 29.4% yield of parent derived products)).

Chromatograms of post-reaction extract using lyophilised material of recombinant P450$_{aluC09}$, ferredoxin$_{aluF03}$ and ferredoxin reductase$_{SCF15A}$ as described in Example 7 dosed with 100mg/L diclofenac. Top to bottom is UV$_{275nm}$, EIC$_{294m/z}$ (diclofenac (1.82 mins)) and EIC$_{310m/z}$ (hydroxy-diclofenac products are at 1.58 and 1.64 minutes 7.4% and 7.6% respectively, of parent derived products).

Chromatograms of post-reaction extract using lyophilised material of recombinant P450$_{aluC09}$, ferredoxin$_{aluF03}$ and ferredoxin reductase$_{SCF15A}$ as described in Example 7 dosed with 100mg/L epothilone B. Top to bottom is UV$_{275nm}$, EIC$_{508m/z}$ (epothilone B (1.66 mins)) and EIC$_{524m/z}$ (hydroxy-epothilone B (1.48 minutes, 2.5% yield of parent derived products)).

Chromatograms of post-reaction extract using lyophilised material of recombinant P450$_{aluC09}$, ferredoxin$_{aluF03}$ and ferredoxin reductase$_{SCF15A}$ as described in Example 7 dosed with 100mg/L buparvaquone. Top to bottom is UV$_{256nm}$, EIC$_{508m/z}$ (buparvaquone (2.47 mins)) and EIC$_{524m/z}$ (hydroxy-buparvaquone (1.96 minutes, 13.1% yield of parent derived products)).

Chromatograms of post-reaction extract using lyophilised material of recombinant P450$_{aluC09}$, ferredoxin$_{aluF03}$ and ferredoxin reductase$_{SCF15A}$ as described in Example 7 dosed with 100mg/L ritonavir (HP-β-CD formulated). Top to bottom is UV$_{240nm}$, EIC$_{721m/z}$ (ritonavir (1.84 mins)) and EIC$_{737m/z}$ (hydroxy-ritonavir (1.62 minutes, 15.5% yield of parent derived products)).

Chromatograms of post-reaction extract using lyophilised material of recombinant P450$_{aluC09}$, ferredoxin$_{aluF03}$ and ferredoxin reductase$_{SCF15A}$ as described in Example 7 dosed with 100mg/L BIRB796. Top to bottom is UV$_{296nm}$, EIC$_{526m/z}$ (BIRB796 (1.28 mins)) and EIC$_{542m/z}$ (hydroxy-BIRB796 (1.09 minutes, 7.4% yield of parent derived products)).

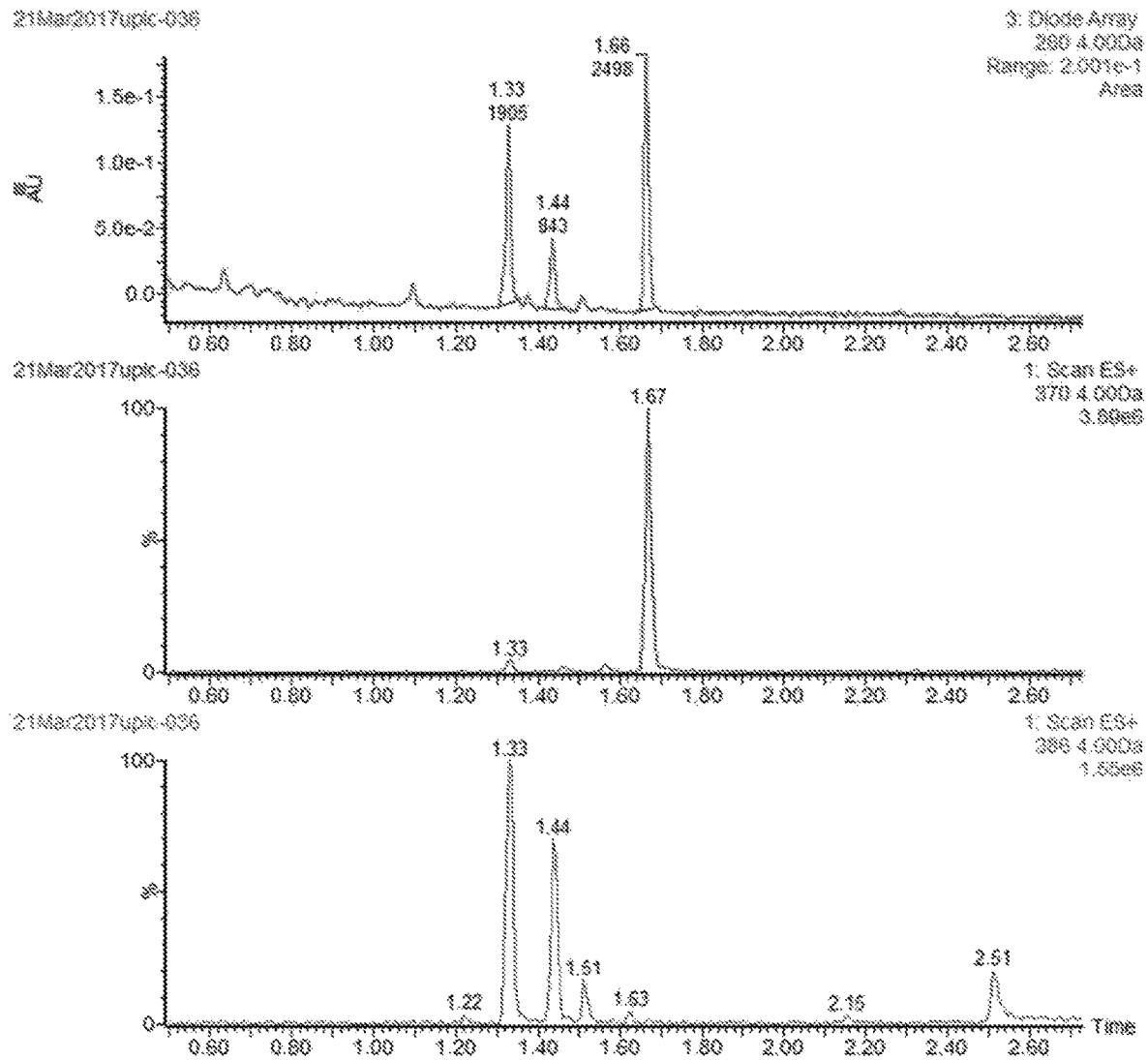

Chromatograms of post-reaction extract using lyophilised material of recombinant P450$_{aluC09}$, ferredoxin$_{aluF03}$ and ferredoxin reductase$_{SCF15A}$ as described in Example 7 dosed with 100mg/L tivantinib. Top to bottom is UV$_{280nm}$, EIC$_{370m/z}$ (tivantinib (1.67 mins)) and EIC$_{386m/z}$ (hydroxylated tivantinib metabolites (1.33 minutes (M4/M5), 1.44 minutes (M7) and 1.51 minutes (M9), total yield 52.3 % of parent derived products)).

Figure 5g

HYDROXYLATION OF BRANCHED ALIPHATIC OR AROMATIC SUBSTRATES EMPLOYING THE AMYCOLATOPSIS LURIDA CYTOCHROME P450

CROSS-REFERENCE TO RELATED APPLICATION

This application is the U.S. national stage application of International Patent Application No. PCT/GB2017/053432, filed Nov. 15, 2017.

The Sequence Listing for this application is labeled "Seq-List.txt" which was created on May 7, 2019 and is 44 KB. The entire content of the sequence listing is incorporated herein by reference in its entirety.

FIELD OF THE INVENTION

The present invention relates to the use of a cytochrome P-450 enzyme for catalysing the hydroxylation of organic substrates.

BACKGROUND OF INVENTION

Cytochrome P450 (CYP) is a superfamily of haem-thiolate proteins named for the spectral absorbance peak of their carbon-monoxide bound species at 450 nm. They are found in all kingdoms of life such as animals, plants, fungi, protists, bacteria, archeae, and furthermore a putative P450 from giant virus *A. polyphaga* has been recently proposed, Lamb, D C; Lei, L; Warrilow, A G; Lepesheva, G I; Muffins, J G; Waterman, M R; Kelly, S L (2009). "*The first virally encoded cytochrome P450*". Journal of Virology. 83 (16): pp8266-9. Cytochrome P450 have not been identified in *E. coli*, Roland Sigel; Sigel, Astrid; Sigel, Helmut (2007). The Ubiquitous Roles of Cytochrome P450 Proteins: Metal Ions in Life Sciences. New York: Wiley. ISBN 0-470-01672-8; Danielson PB (December 2002). "The cytochrome P450 superfamily: biochemistry, evolution and drug metabolism in humans". Curr. Drug Metab. 3 (6): pp561-97.

Cytochrome P450 shows extraordinary diversity in their reaction chemistry supporting the oxidative, peroxidative and reductive metabolism of a diversity of a range of endogenous and xenobiotic substrates.

In humans, cytochrome P450 are best known for their central role in phase I drug metabolism where they are of critical importance for two of the most significant problems in clinical pharmacology: drug interaction and inter-individual variability in drug metabolism.

The most common reaction catalyzed by cytochromes P450 is a mono-oxygenase reaction. Cytochrome P450 mono-oxygenases use a haem group to oxidise molecules, often making them more water-soluble by either adding or unmasking a polar group. In general the reaction catalysed by these enzymes can be summarised as:

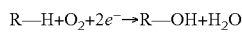

$$R\text{—}H + O_2 + 2e^- \rightarrow R\text{—}OH + H_2O$$

Where R—H is the substrate and R—OH is the oxygenated substrate. The oxygen is bound to the haem group in the core of the CYP enzyme, protons (H$^+$) are usually derived from the reduced cofactor NADH or NADPH through specific amino acids in the CYP enzyme. CYP enzymes can receive electrons from a range of redox partner proteins such as cytochrome b5, a ferredoxin reductase and a ferredoxin, and adrenodoxin reductase and adrenodoxin.

Although classification and nomenclature of cytochrome P450 is quite complex, they can be classified by their redox partner transfer protein system, proposed by I. Hanukoglu (1996). "*Electron Transfer Proteins of Cytochrome P450 Systems*". Advances in Molecular and Cell Biology. Advances in Molecular and Cell Biology. 14: 29-56. In summary, cytochromes P450 can be classified into the following groups:

Microsomal P450 systems which utilise cytochrome P540 reductase or cytochrome b5 to transfer electrons from cofactor to cytochrome P450;

Mitochondrial P450 systems which utilise adrenodoxin reductase and adrenodoxin to transfer electrons from reduced cofactor to cytochrome P450;

Bacterial P450 systems which utilise ferredoxin reductase and ferredoxin to transfer electrons from reduced cofactor to cytochrome P450;

CYB5R-cytb5-P450 systems, which utilise cytochrome b5 for the electron transfer from the cofactor to the cytochrome P450;

FMN-Fd-P450 systems in which the electron partner reductase is a fused FMN domain;

P450 only systems that do not require redox partner proteins, e.g., P450$_{BM-3}$.

Isolated bacterial cytochrome P450 enzymes are known, including P450$_{cam}$, from *Pseudomonas putida*, J Biol Chem (1974) 249, 94; P450$_{BM-1}$ and P450$_{BM-3}$ both from *Bacillus megaterium* ATCC 14581, Biochim Biophys Acta (1985) 838, 302, and J Biol Chem (1986) 261, 1986, 7160; P450a, P450b, and P450c from *Rhizobium japonicum*, Biochim Biophys Acta (1967) 147, 399; and P450npd from *Nocardia* NHI, Microbios (1974) 9, 119.

However, cytochrome P450 enzymes purified from Actinomycete microorganisms remain relatively unreported. The induction of a cytochrome P-450 in *Streptomyces griseus* by soybean flour (P450$_{soy}$) is described in Biochem and Biophys Res Comm (1986) 141, 405. Other reported examples include the isolation and properties of two forms of a P450 effecting pesticide inactivation (P450$_{SU1}$ & $_{SU2}$) and two forms of 6-deoxyerythronolide B hydroxylase from *Saccharopolyspora erythraea* (originally classified as *Streptomyces erythraeus*) as described in Biochemistry (1987) 26, 6204. U.S. Pat. No. 6,884,608 describes enzymatic hydroxylation of epothilone B to epothilone F, effected with a hydroxylation enzyme produced by a strain of *Amycolatopsis orientalis* (originally classified as *Streptomyces orientalis*).

In the field of medicinal chemistry, modifications to chemical compounds are used to modify the properties of such chemical compounds. For example, tertiary butyl moieties are often used by medicinal chemists in the synthesis of drug-like molecules for introduction of hydrophobicity. However, further modifications thereof can be used to improve potency, selectivity and solubility profiles of such compounds, for example hydroxylations can be used. Hydroxylations are also the main route of metabolic degradation, another important aspect of pharmacology and medicinal chemistry. Methods for the production of these hydroxylated metabolites are sought using biotransformation with animal tissues.

SUMMARY OF THE INVENTION

It has surprisingly been found that a cytochrome P-450 enzyme found in *Amycolatopsis lurida* NRRL-2430 can be used for the hydroxylation of a wide range of organic substrates.

In particular, a cytochrome P-450 enzyme having the SEQ ID NO: 3 can be used for the hydroxylation of organic compounds in order to activate or modify the compound's physicochemical and pharmacological properties. In a particularly preferred embodiment, the cytochrome P-450 enzyme having the SEQ ID NO: 3 is used for the hydroxylation of isopropyl or tertiary butyl moieties, or chemicals containing such moiety, for the purposes of C—H activation or modification of the compound's physicochemical and pharmacological properties.

A first aspect of the invention provides the use of a cytochrome P-450 enzyme comprising SEQ ID NO: 3, or a variant enzyme having at least 70% identity thereto and having CYP-450 activity, for the hydroxylation of an organic compound.

A second aspect of the invention provides a method for the production of a hydroxylated organic compound, comprising reacting the organic compound with an enzyme preparation containing in part the cytochrome P-450 enzyme comprising SEQ ID NO: 3, or a variant enzyme having at least 70% identity thereto and having CYP-450 activity.

A third aspect of the invention provides a kit comprising i) a cytochrome P-450 enzyme comprising SEQ ID NO: 3, or a variant enzyme having at least 70% identity thereto and having CYP-450 activity, or ii) a microorganism that expresses a cytochrome P-450 enzyme comprising SEQ ID NO: 3, or a variant enzyme having at least 70% identity thereto and having CYP-450 activity, wherein the kit further comprises instructions and other cofactor reagents for use for the hydroxylation of an organic compound.

BRIEF DESCRIPTION OF THE FIGURES

FIG. 1 shows schematic examples of the biotransformation effected by the present invention. FIG. 1(a) shows hydroxylation of bosentan; FIG. 1(b) shows hydroxylation of buparvaquone; FIG. 1(c) shows hydroxylation of ritonavir; FIG. 1(d) shows hydroxylation of tivantinib; FIG. 1(e) shows hydroxylation of diclofenac.

FIG. 2 shows various ID sequences. SEQ ID NO: 1 is the nucleic acid sequence of P450 aluC09 and ferredoxin aluF03; SEQ ID NO: 2 is the coding sequence of P450 aluC09 and ferredoxin aluF03; SEQ ID NO: 3 is the amino acid sequence of P450 AluC09, SEQ ID NO: 4 is the amino acid sequence of ferredoxin AluF03, SEQ ID NO: 9 is the synthetic DNA subcloned into pD454-SR plasmid via NdeI and NotI by DNA2.0; SEQ ID NO: 10 is the amino acid sequence of Ferredoxin Fd1; SEQ ID NO: 11 is the amino acid sequence of Ferredoxin reductase SCF15A, SEQ ID NO: 14 is the coding sequence of ferredoxin reductase camA and ferredoxin camB, SEQ ID NO: 15 is the amino acid sequence of ferredoxin reductase CamA; SEQ ID NO: 16 is the amino acid sequence of ferredoxin CamB; SEQ ID NO: 23 is the synthetic DNA subcloned into pET29a via NdeI and NotI by Genscript); SEQ ID NO: 24 is the amino acid sequence of the truncated P450 BM3; SEQ ID NO: 25 is the coding sequence of P450 aluC09 fused in-frame with the reductase domain of P450 BM3 SEQ ID NO: 26 is the amino acid sequence of P450 AluC09 fused in-frame with the reductase domain of P450 BM3.

FIGS. 5a to 5g show UPLC chromatograms of various reactions performed at 100 uL screening scale.

DESCRIPTION OF THE PREFERRED EMBODIMENTS

Figure 3:
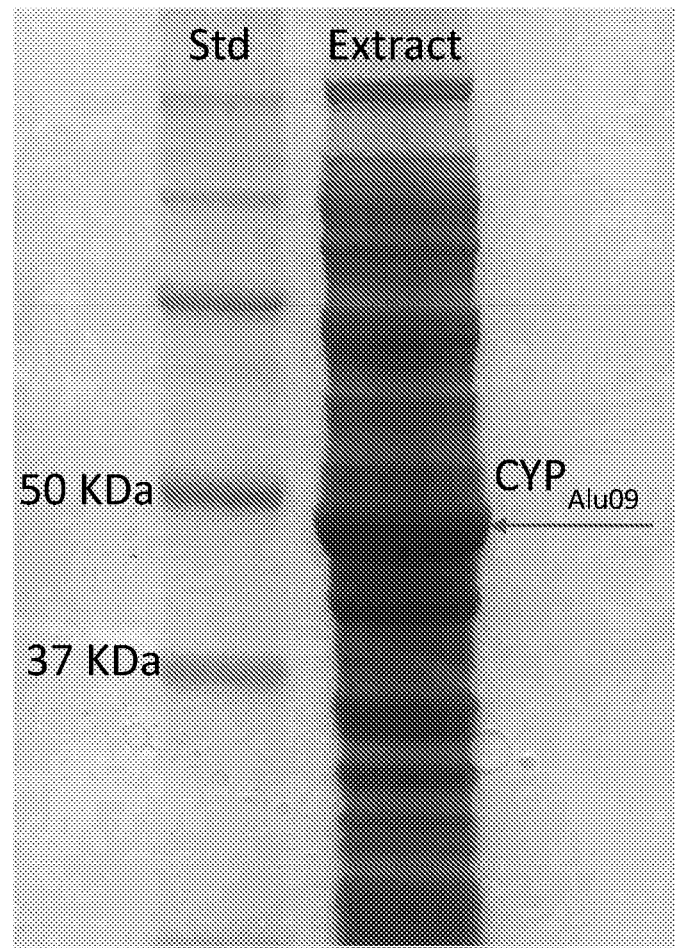
FIG. 3 shows SDS-PAGE analysis of crude enzyme extracts containing P450$_{aluC09}$ protein (see arrow). The samples were prepared from IPTG-induced culture of E. coli BL21 Star (DE3) pLysS cells containing the pQR368bb-aluC09-aluF03 plasmid.
Figure 4:
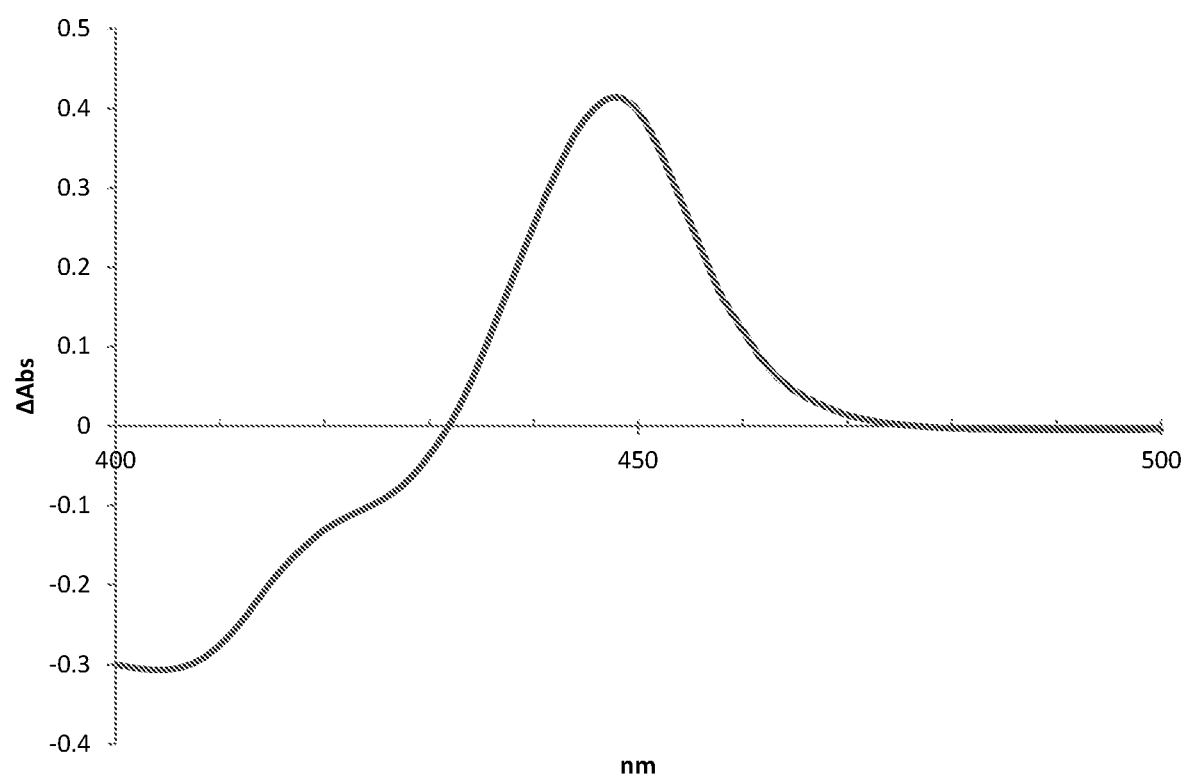
FIG. 4 shows the carbon monoxide difference spectrum of the crude enzyme extract containing P450$_{aluC09}$ protein. The sample was prepared from IPTG-induced culture of E. coli BL21 Star (DE3) pLysS cells containing the pQR368bb-aluC09-aluF03 plasmid.
Figure 5A:
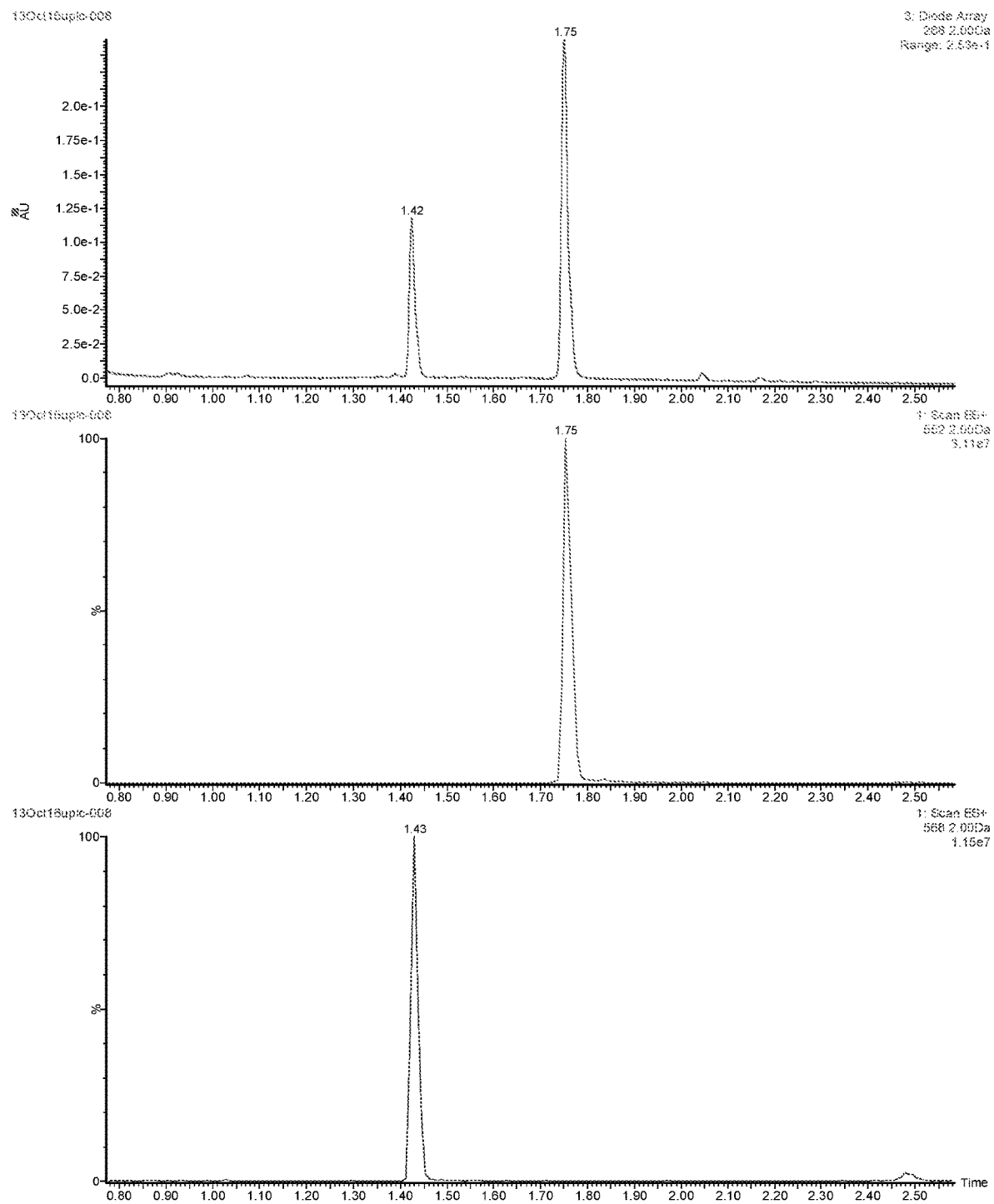
Figure 5B:
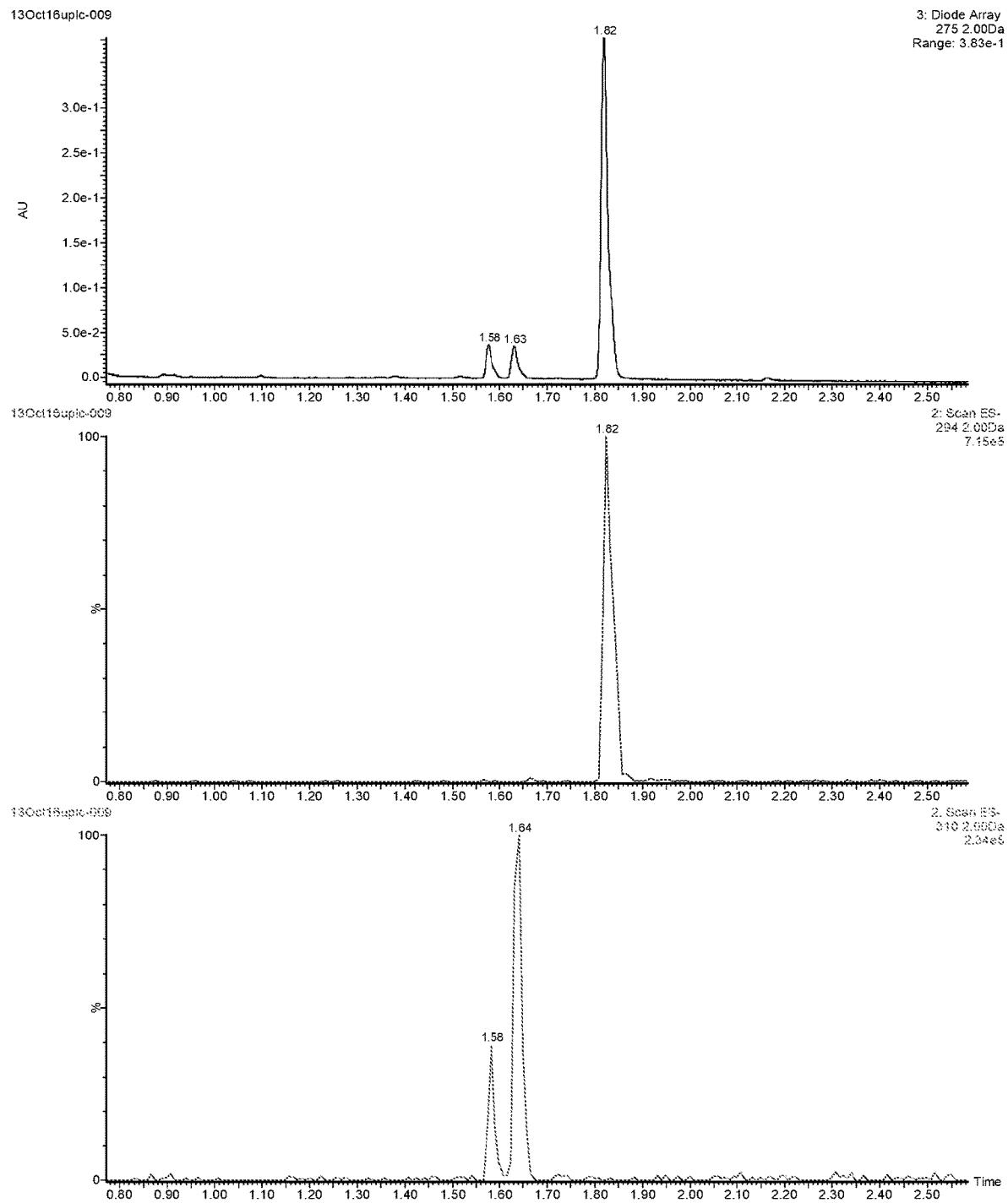
Figure 5C:
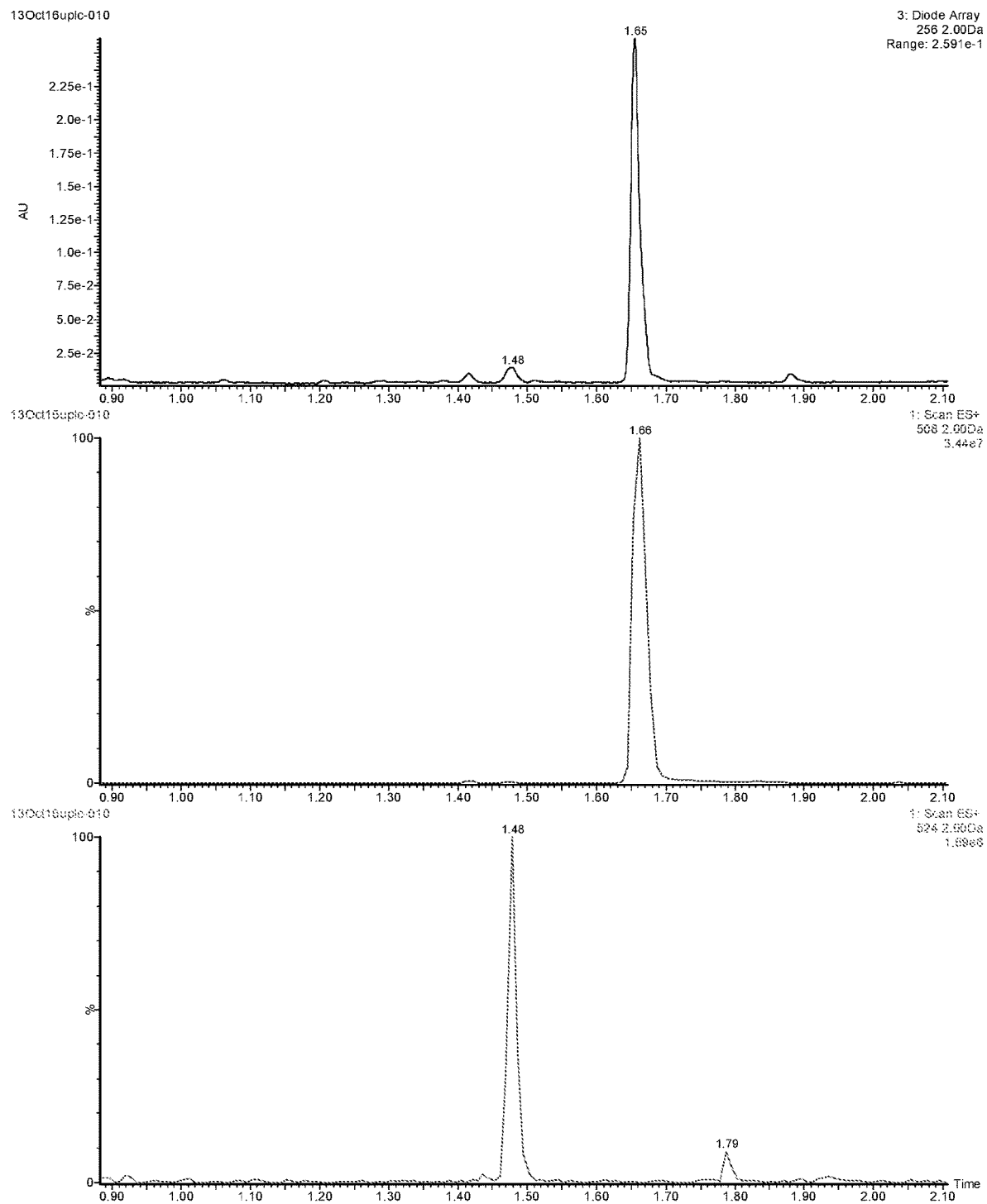
Figure 5D:
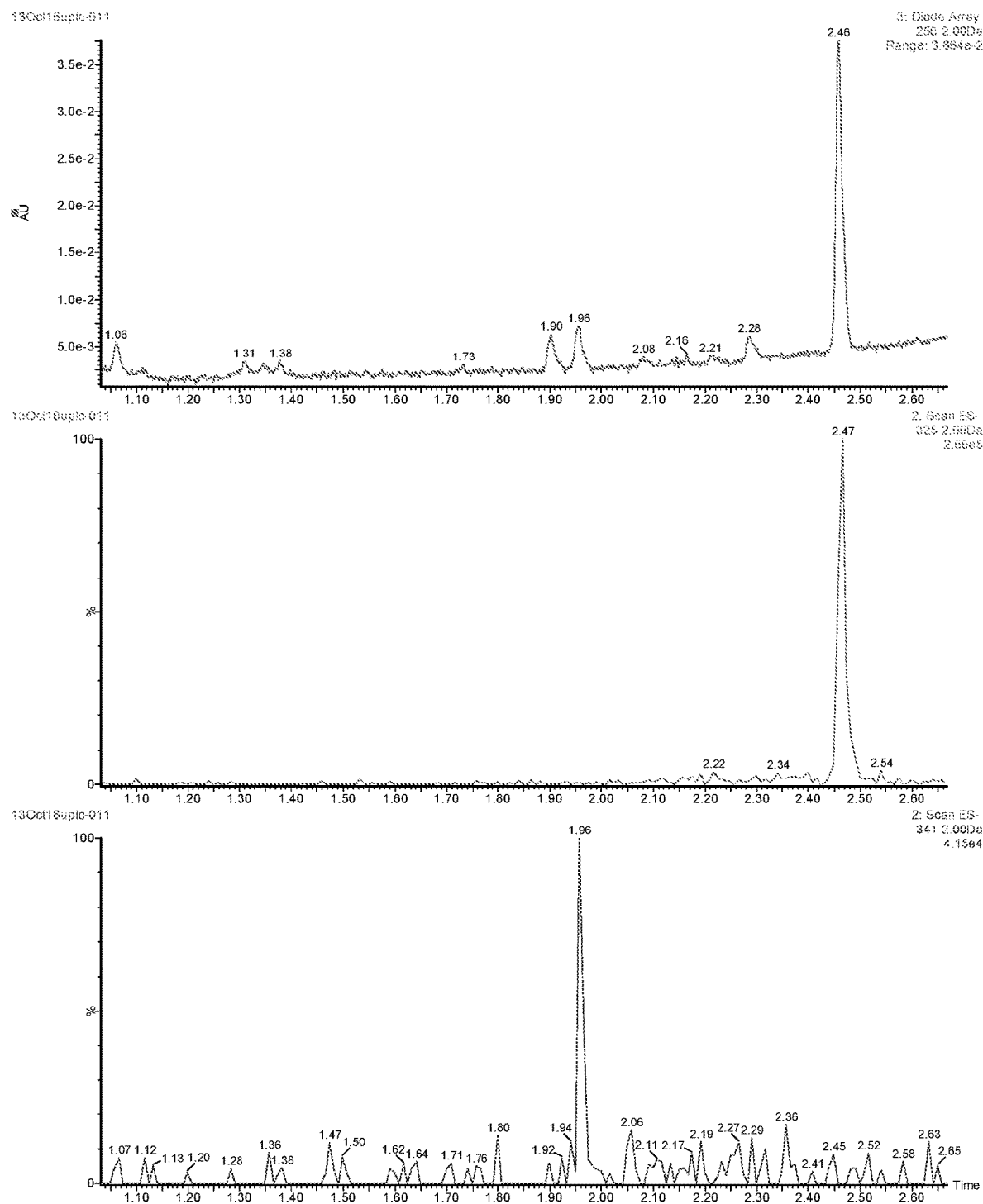
Figure 5E:
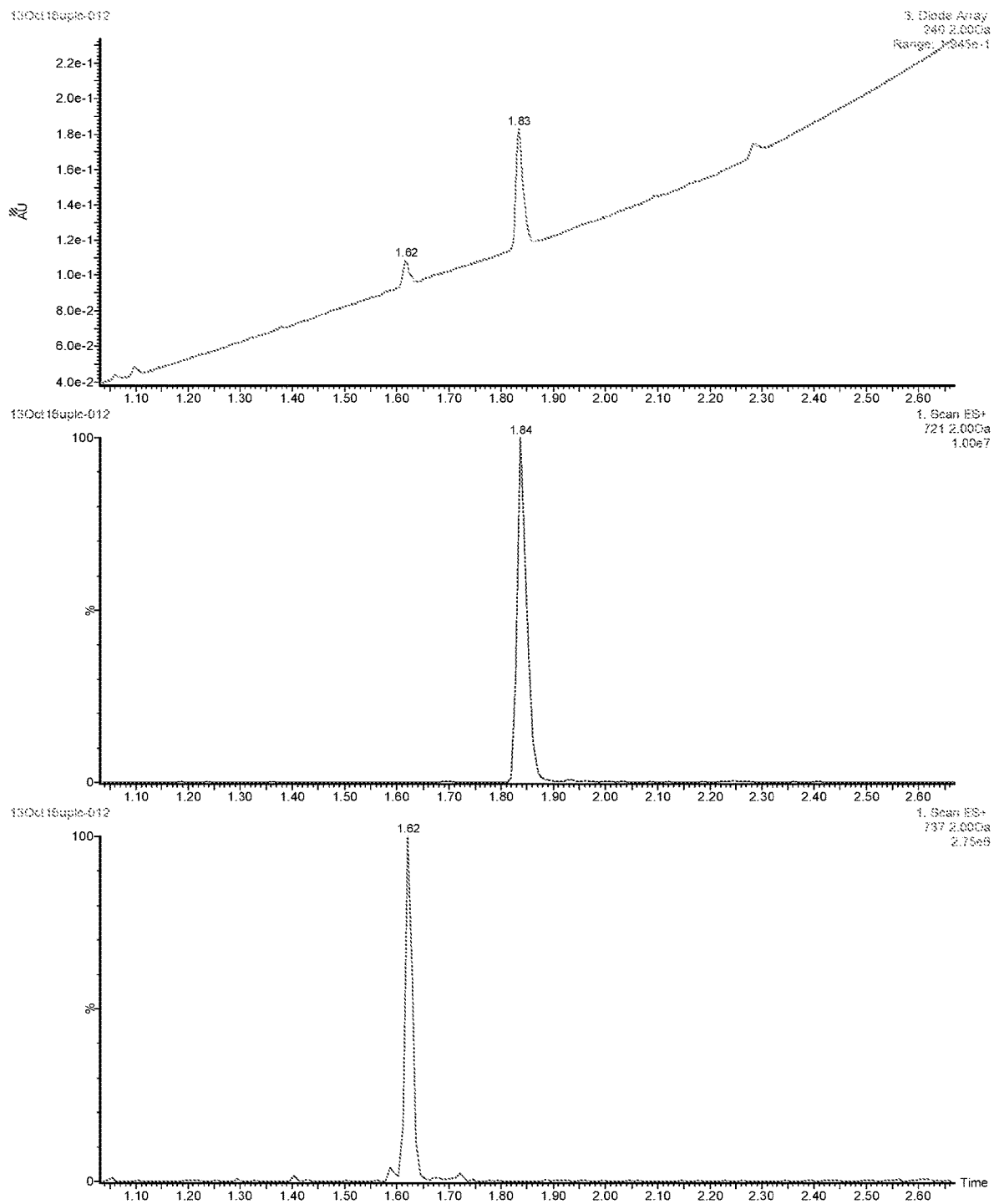
Figure 5F:
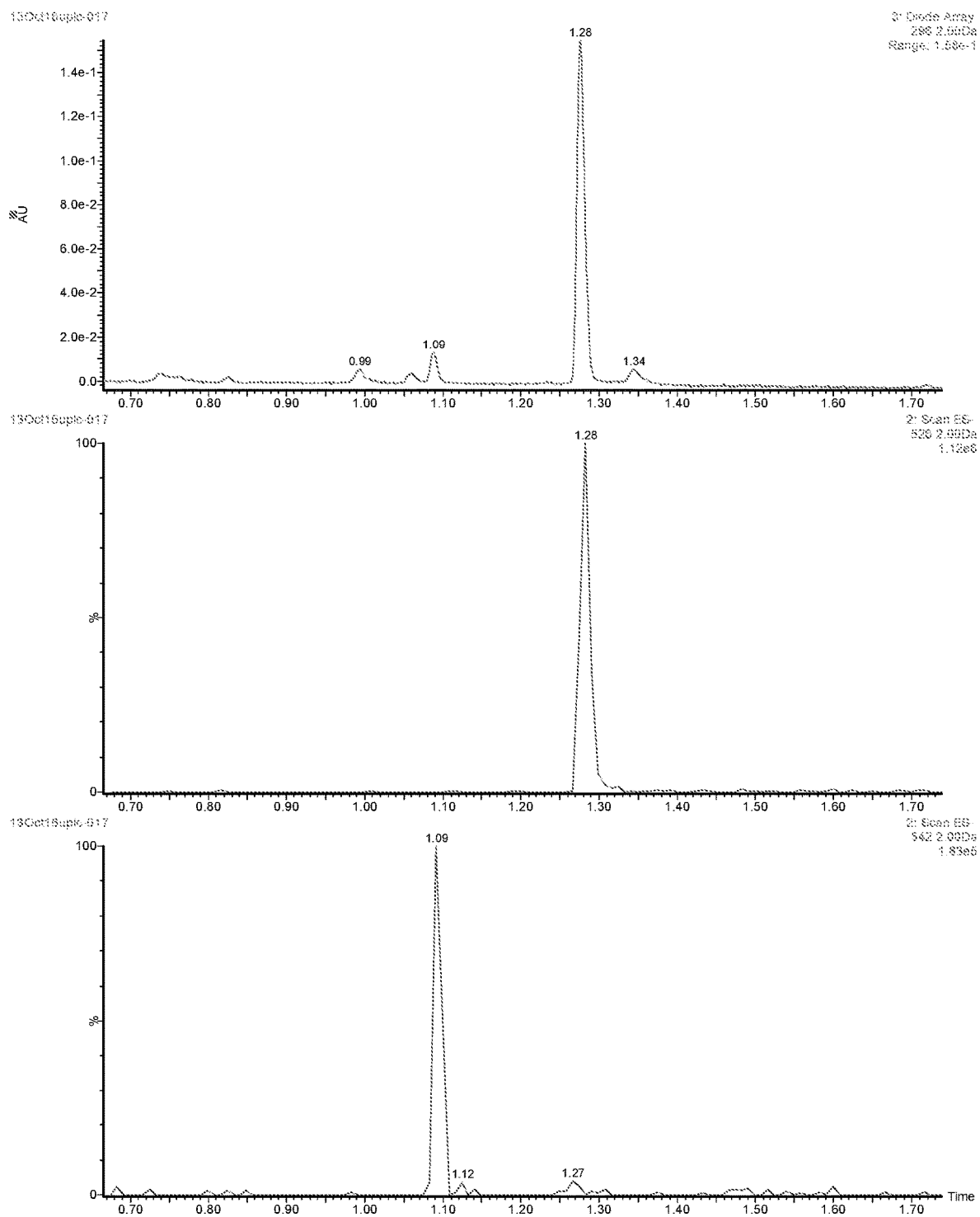
Figure 6:
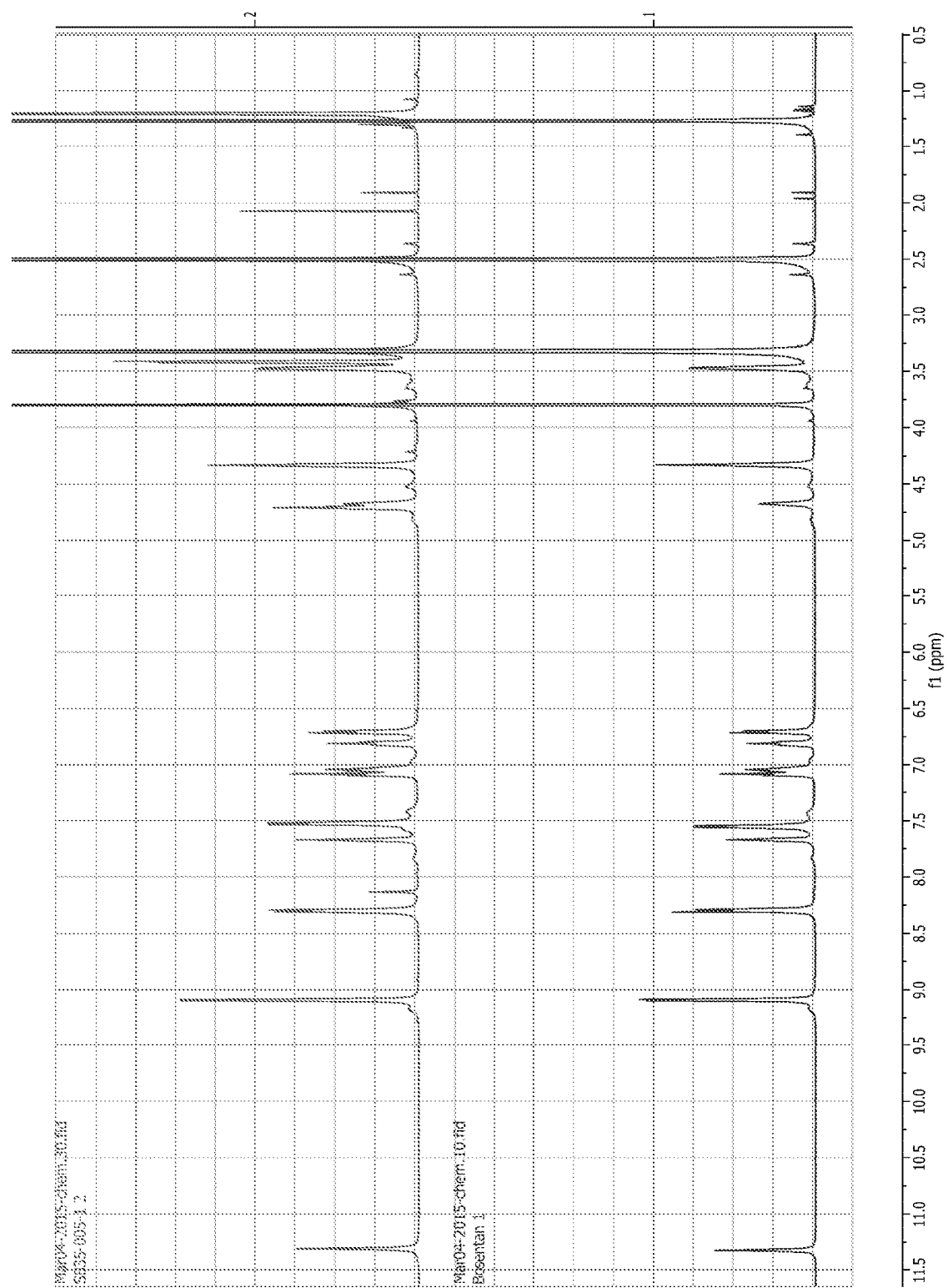
FIG. 6 shows the 1H-NMR spectra of OH-Bosentan (top) compared to bosentan (bottom) both in DMSO-d6: the appearance of a new signal at 3.42 ppm ((2H, doublet, C$\underline{H}_2$OH), and the reduction of the methyl signal integral from 9H in bosentan compared to 6H in hydroxybosentan confirm the point of hydroxylation as the t-butyl group.
Figure 7:
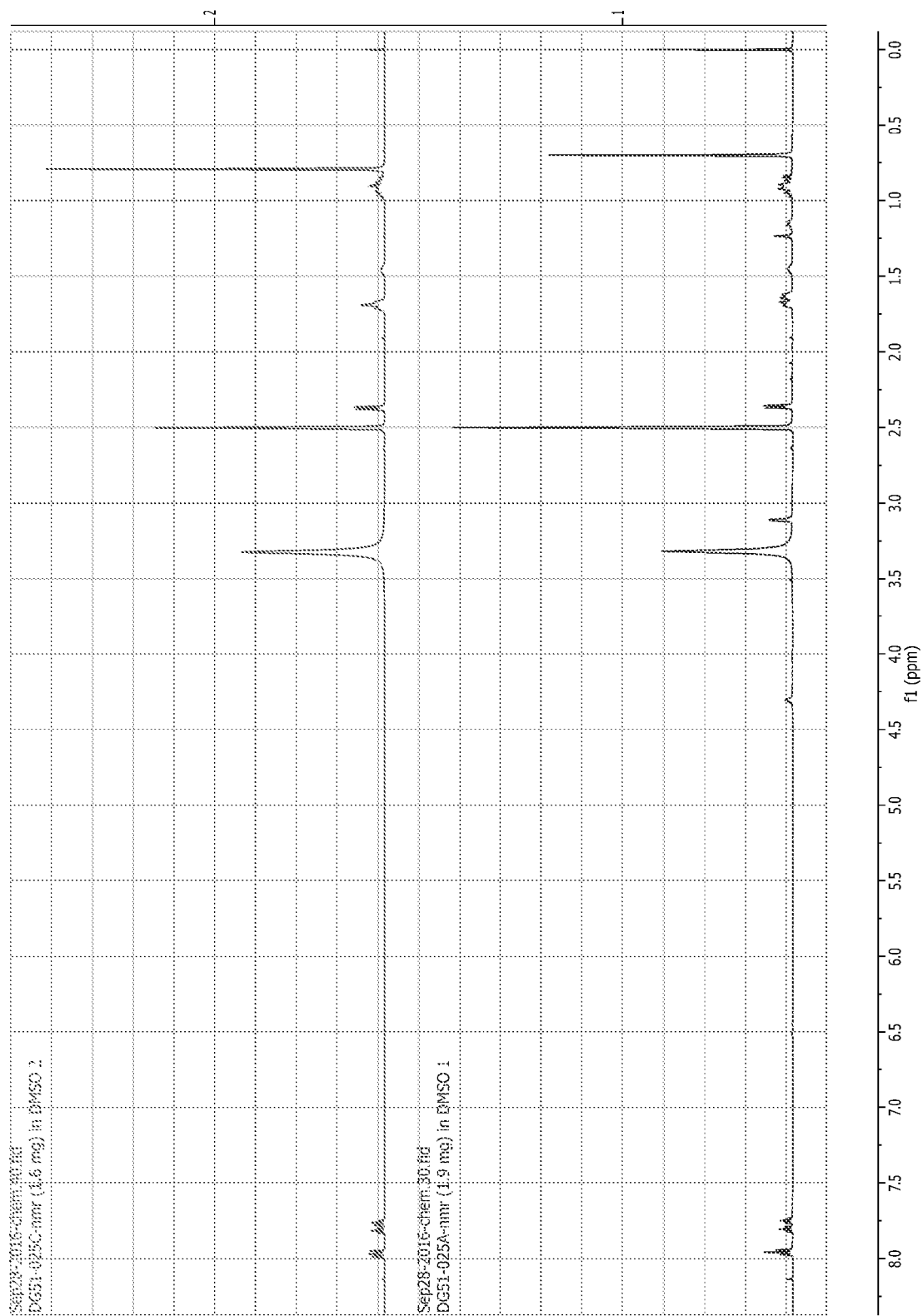
FIG. 7 shows the 1H-NMR spectra in DMSO-d6 of HO-Buparvaquone (bottom) compared to buparvaquone (top): appearance of new signals at 4.31 ppm (1H, triplet, hydroxyl proton) and 3.12 ppm (2H, doublet, CH$_2$OH), and the reduction of the methyl signal integral from 9H in buparvaquone compared to 6H in hydroxybuparvaquone confirm the point of hydroxylation as the t-butyl group.
Figure 8:
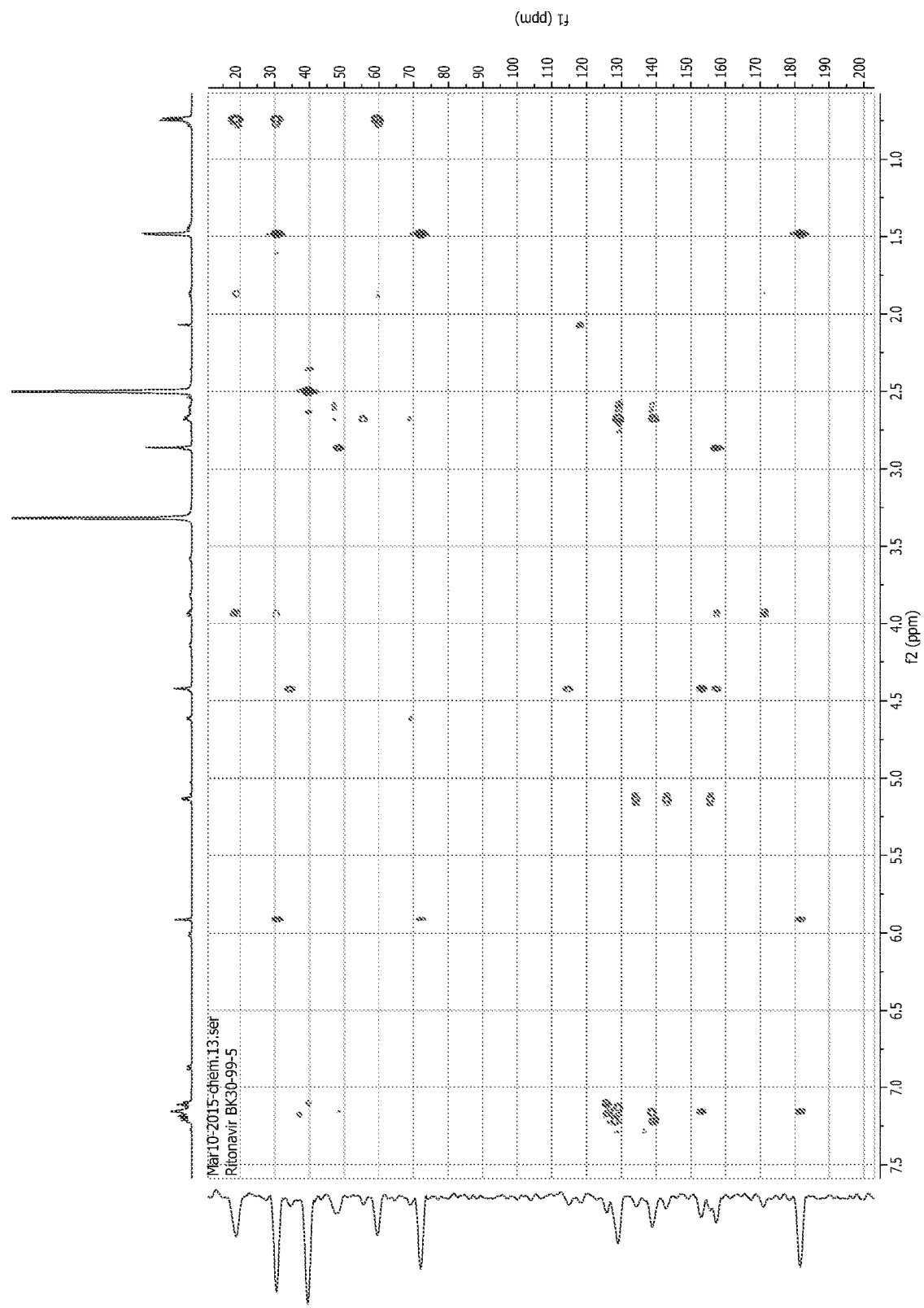
FIG. 8 shows the HMBC NMR spectrum of ε-HO—N-methylisopropylthiazoloylmethyl-ritonavir in DMSO-d6. The isopropyl methyl signals are now singlets at 1.49 and 1.48 ppm and show correlations to the hydroxylated bridging carbon at 71.5 ppm, the thiazolyl carbon at 181 ppm, and to each other's carbons at 30 ppm. The new hydroxyl proton is evident as a singlet at 5.91 ppm and shows correlations to the same carbons. The thiazolyl proton singlet at 7.16 ppm also correlates to the carbon at 181 ppm.
Figure 9:
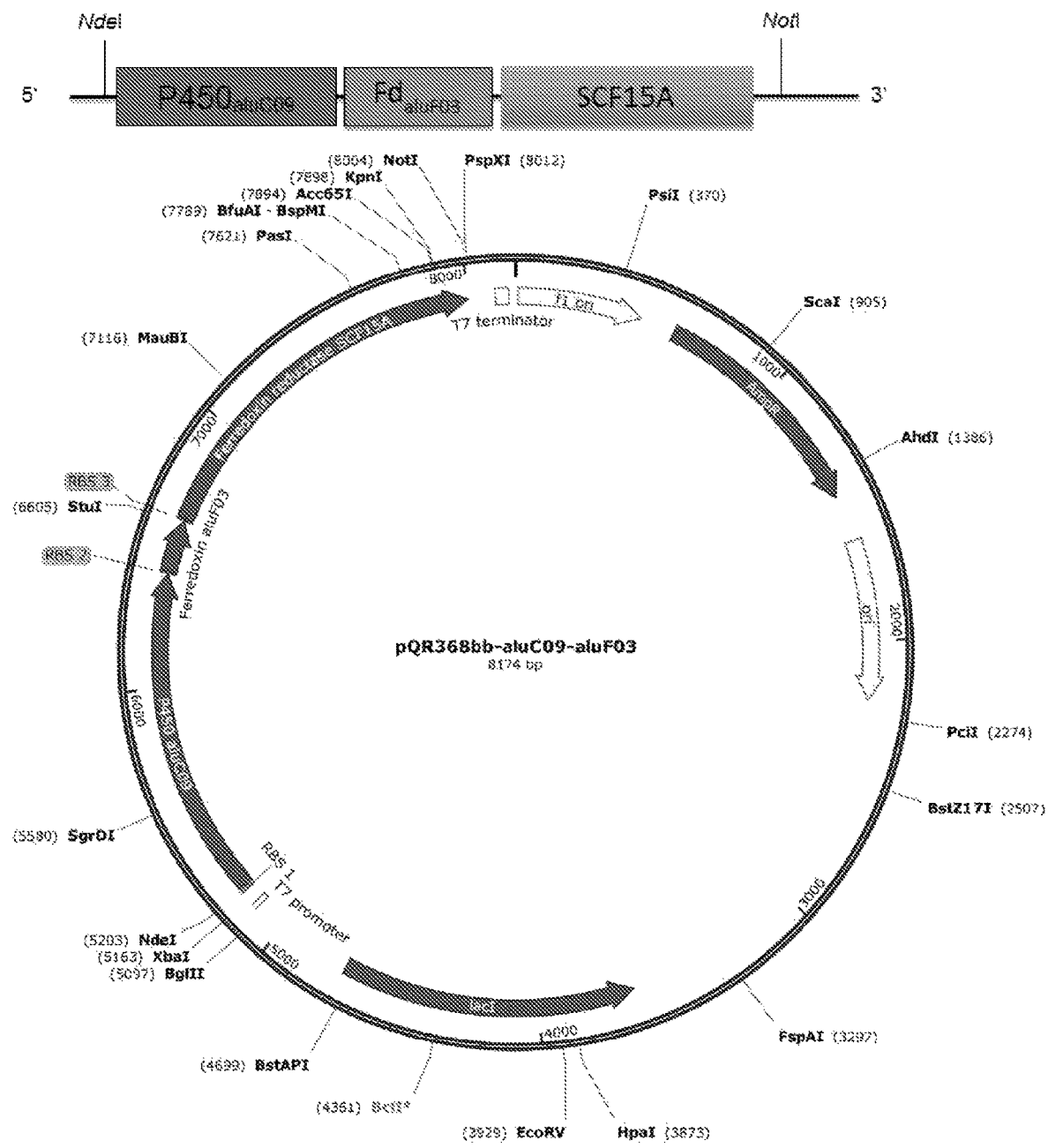
FIG. 9. shows expression vector pQR368bb-aluC09-aluF03.

A first aspect of the invention provides the use of a cytochrome P-450 enzyme comprising SEQ ID NO: 3, or a variant enzyme having at least 70% identity thereto and having CYP-450 activity, for the hydroxylation of an organic compound.

Specifically, the present invention provides the use of the enzyme cytochrome P-450$_{aluC09}$. This enzyme has amino acid sequence as shown in SEQ ID NO: 3.

The enzyme is present in the strain *Amycolatopsis lurida*, deposited in the ARS Culture Collection, National Center for Agricultural Utilization Research, 1815 North University Street, Peoria, Ill. 61604, USA, under the Accession number NRRL 2430. The strain has also been deposited with the American Tissue Culture Collection, with the accession number ATCC 14930.

When this enzyme, or a variant thereof, is combined with suitable reductase components, it is able to hydroxylate organic compounds.

The enzyme cytochrome P-450$_{aluC09}$ can be extracted, with or without purification from the known *Amycolatopsis lurida* NRRL-2430, or other bacterial strain, or similarly extracted, with or without purification from a recombinant expression system via cloning of cytochrome P-450$_{aluC09}$ into an expression system, such as *E. coli*, as will be understood by the skilled person.

Actinomycetes including *Amycolatopsis lurida* NRRL-2430 readily undergo mutation both through natural causes and as a result of artificial treatments such as UV irradiation, radiation treatment and chemical treatment. The present invention embraces all productive mutants of *Amycolatopsis lurida* NRRL-2430. These mutant strains also include any strains obtained by gene manipulation such as gene recombination, transduction and transformation. It is also well-known that the properties of Actinomycetes change in some degree even for the same strain after successive cultures. Therefore, strains cannot always be differentiated taxonomically because of a slight difference in culture properties. This invention embraces all strains that can produce one or more of the cytochromes P-450 enzymes, and especially strains that cannot be clearly differentiated from strain NRRL-2430 or its mutants.

One of skill in the art will appreciate that the present invention can include variants of those particular amino acids sequences which are exemplified herein. Particularly preferred are variants having an amino acid sequence similar to that of the amino acid sequences disclosed herein, in which one or more amino acids residues are substituted, deleted or added in any combination. Especially preferred are silent substitutions, additions and deletions, which do not alter the properties and activities of the protein of the present invention. Various amino acids have similar properties, and one or more such amino acids of a substance can often be substituted by one or more other amino acids without eliminating a desired activity of that substance. Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Variants include naturally occurring and artificial variants. Artificial variants may be generated using mutagenesis techniques, including those applied to nucleic acid molecules, cells or organisms. Preferably, the variants have substantial identity to the amino acid sequences exemplified herein. As used herein, the term "variant" or "mutant thereof" refers to amino acid sequences which have "substantial identity", preferably having at least 70%, 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%,99.5%, 99.6%, 99.1%, 99.8% or 99.9% identity with SEQ ID NO 3. Desirably, the term "substantial identity" indicates that said sequence has a greater degree of identity with any of the sequences described herein than with prior art amino acid sequences. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applied mutatis mutandis to all amino acid sequences disclosed in the present application.

"In a preferred embodiment, the term "variant" or "mutant thereof" generally refers to a sequence having at least 70% identity to SEQ ID No 3 and CYP450 activity, more preferably least 90% identity thereto or at least 95% identity thereto, further preferably 96% identity thereto, even more preferably 97% identity thereto, most preferably 100% identity thereto.

A variety of different compounds can be hydroxylated using the claimed cytochrome P-450 enzyme. In a preferred embodiment, the organic compound to be hydroxylated will have a rate of conversion to the hydroxylated derivative of at least 3%, more preferably at least 5%, more preferably at least 10%, more preferably at least 25%, more preferably at least 50%, even more preferably at least 70% and most preferably a rate of conversion to the hydroxylated derivative of 100%, using the same conditions described in Example 7 herein.

Preferably, the organic compound to be hydroxylated is not epothilone.

The compound to be hydroxylated by the cytochrome P-450 enzyme may have an optionally substituted branched alkyl group, such as isopropyl or tert butyl, which is hydroxylated; or an aromatic group, such as an optionally substituted aryl or heteroaryl, which is hydroxylated.

There is a particularly high conversion rate from these compounds to their hydroxylated derivatives when using the claimed cytochrome P-450 enzyme.

Preferably, the compound to be hydroxylated is of formula Ia or Ib:

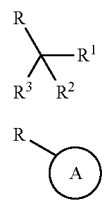

where R represents the rest of the compound, and where $R^1$, $R^2$ and $R^3$ are independently selected from H or $C_{1-12}$ alkyl or $C_{6-10}$ aryl, or wherein any two of $R^1$, $R^2$ and $R^3$ may be joined to form an optionally substituted cycloalkyl or heterocycloalkyl or $R^1$, $R^2$ and $R^3$ may be joined together with their bridging carbon to form an olefin, aryl or heteroaryl, and wherein A is optionally substituted benzyl, aryl or heteroaryl.

Preferably R is an optionally substituted alkyl; an optionally substituted olefin, an optionally substituted aryl, optionally substituted heteroaryl or optionally substituted heterocycloalkyl.

Preferably, A is benzyl, aryl or heteroaryl, optionally substituted with one or more halogen atoms, $C_1$-$C_8$ alkyl, $C_1$-$C_8$ alkoxy, —COOH, $C_1$-$C_8$—COOH, cyano, amino or alkylamino groups.

More preferably, A is benzyl, aryl or heteroaryl optionally substituted with one or more halogen atoms, $C_1$-$C_4$ alkyl, —COOH or $C_1$-$C_4$ Alkyl-COOH groups.

More preferably, A is $C_6$ aryl or $C_4$-$C_{20}$ bicyclic or tricyclic heteroaryl, optionally substituted with $C_1$-$C_8$ alkyl, $C_1$-$C_8$ alkoxy, —COOH, $C_1$-$C_8$—COOH, cyano, amino or alkylamino groups.

Most preferably, A is indolyl, isindolyl, azaindolyl or a group having the formula.

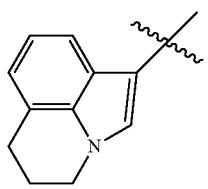 [SMILES: *c1cn2c3c(cccc13)CCC2]

As used herein "alkyl" means a $C_1$-$C_{10}$ alkyl group, which can be linear or branched or cyclic. Examples include propyl and butyl, pentyl, hexyl, cyclopentyl and cyclohexyl. Preferably, it is a $C_3$-$C_{10}$ alkyl moiety. More preferably it is a $C_5$-$C_6$ alkyl moiety. Preferably the alkyl is an optionally substituted cyclohexyl.

As used herein "alkoxy" means on alkyl group, as defined above, having an oxygen atom attached thereto.

As used herein "halogen" refers to fluorine, chlorine, bromine and iodine.

As used here the term "alkylamino" means at least one alkyl group, as defined herein, is appended to the parent molecular moiety though an amino group. By way of non-limiting example, suitable alkylamino groups include methlamino, ethlamino, proylamino, butylamino and hexylamino.

The term "alkenyl" means a straight or branched hydrocarbon chain containing at least one carbon-carbon double bond and from 1 to 10 carbon atoms.

For the avoidance of any doubt, the term cycloalkyl is a cyclic alkyl group.

As used herein "aryl" means an optionally substituted monocyclic, bicyclic or tricyclic aromatic radical, such as phenyl, biphenyl, napthyl, anthracenyl. Preferably the aryl is an optionally substituted $C_6$ aryl.

As used herein "heteroaryl" means an optionally substituted monocyclic, bicyclic or tricyclic aromatic radical containing at least one and up to four heteroatoms selected from oxygen, nitrogen and sulfur, such as furanyl, pyrrolyl, thiazolyl, isothiazolyl, tetrazolyl, imidazolyl, oxazolyl, isoxazolyl, thienyl, pyrazolyl, pyridinyl, pyrazinyl, pyrimidinyl, indolyl, azaindolyl, isoindolyl, quinolyl, isoquinolyl, triazolyl, thiadiazolyl, oxadiazolyl. Preferably the heteroaryl is an optionally substituted thioazole.

As used herein heterocycloalkyl means an optionally substituted cycloalkyl wherein one to four carbon atoms have been substituted with a heteroatom. Preferably, the heteroatoms are selected from nitrogen, oxygen, sulphur or phosphorous.

As used herein the term "optionally substituted" means an H has been removed from a compound and replaced with an organic fragment such as those those comprising a combination of any of carbon, hydrogen, nitrogen, oxygen and sulphur.

Preferably the compound of formula I has a molecular weight of from 50 to 2000, such as from 100 to 700, more preferably from 200 to 500.

Preferably at least 2 of $R^1$, $R^2$ and $R^3$ are selected from $C_{1-12}$ alkyl or $C_{6-10}$ aryl. Preferably, $R^1$, $R^2$ and $R^3$ are independently selected from H, $C_{1-6}$ alkyl or $C_{6-10}$ aryl, preferably with the proviso that either one or none of $R^1$, $R^2$ and $R^3$ is H. Most preferably, $R^1$, $R^2$ and $R^3$ are independently selected from H, methyl, ethyl, propyl, butyl, t-butyl, pentyl and hexyl preferably with the proviso that either one or none of $R^1$, $R^2$ and $R^3$ is H.

In a particularly preferred embodiment, the compound to be hydroxylated is of formula (II), where R represents the rest of the compound and where $R^1$ is $CH_3$ or H:

(II)

In this case, the cytochrome P-450 enzyme catalyses the following reaction:

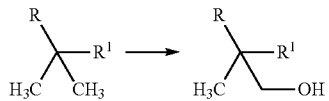

Where $R^1$ = H, $CH_3$

Therefore, in a particular preferred embodiment, the organic compound contains an isopropyl or tert-butyl group. Most preferably, the group to be hydroxylated is a tert-butyl moiety. The cytochrome P-450 enzyme catalyses the conversion of a substrate compound with a tert-butyl moiety to a hydroxylated-tert-butyl derivative.

In a particularly preferred embodiment, the cytochrome P-450 enzyme is reacted with a compound such as bosentan, diclofenac, buparvaquone, tivantinib, BIRB796 or ritonavir. Most preferably, the cytochrome P-450 enzyme is reacted with bosentan, buparvaquone, BIRB796 or ritonavir.

The compounds of formula I are typically of the following structural formulae:

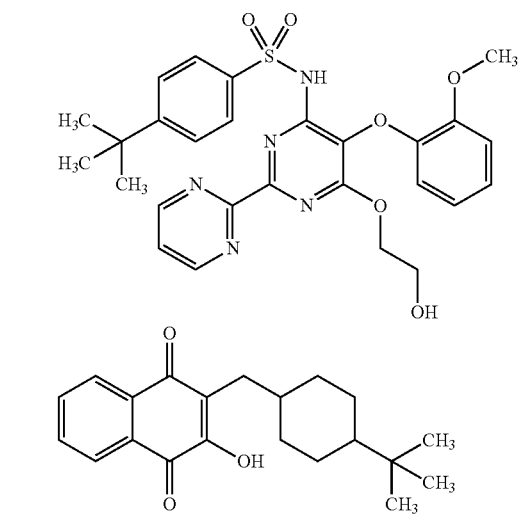

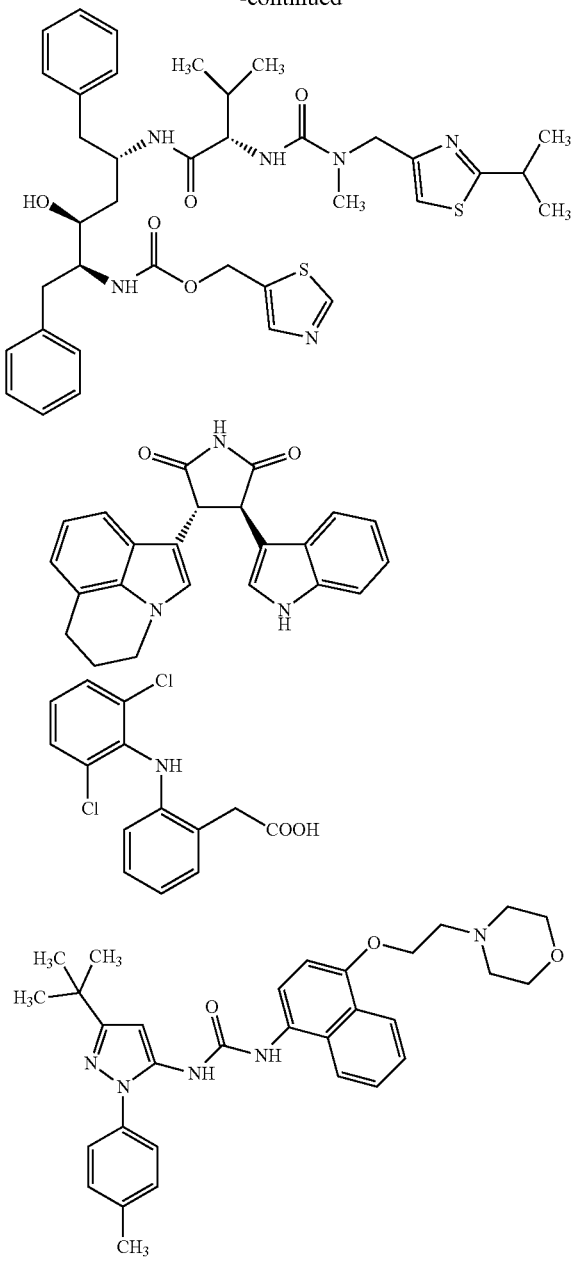

The cytochrome P-450 enzyme may optionally be used in combination with reductase components, which activate the cytochrome P-450. In a preferred embodiment, ferredoxin and ferredoxin reductase components are used. Any components which activate the cytochrome P-450 may also be used, including small-molecule chemicals acting directly or indirectly, protein chemicals in solution or those fused directly or by peptide linkage, or electronic via electrode. In a particularly preferred embodiment, the enzyme cytochrome P-450aluC09 having SEQ ID NO 3, or a variant enzyme having at least 70% identity thereto and having CYP-450 activity, is combined with suitable ferredoxin and ferredoxin reductase components to give an effective system to convert a substrate compound to a hydroxylated derivative.

In a preferred embodiment, the cytochrome P-450 enzyme or variant thereof is present in *Amycolatopsis lurida* (NRRL-2430) cells.

In another preferred embodiment, the cytochrome P-450 enzyme or variant thereof is expressed by at least one recombinant microorganism comprising heterologous nucleic acid encoding the enzyme, derived from *Amycolatopsis lurida* (NRRL 2430). As used herein the term "comprising" is intended to mean containing at least the claimed sequence, but may include other sequences. In one embodiment, the recombinant microorganism comprises a heterologous nucleic acid encoding the enzyme or variant thereof. In an alternative embodiment, the recombinant microorganism also comprises a heterologous nucleic acid encoding a reductase agent.

In another aspect of the invention, there is provided a method for the production of a hydroxylated organic compound, comprising reacting the organic compound with a cytochrome P-450 enzyme comprising SEQ ID NO: 3, or a variant enzyme having at least 70% identity thereto and having CYP-450 activity.

The choice of compound to be hydroxylated is discussed above.

In a preferred embodiment, the enzyme is used to catalyse the hydroxylation of a propyl group or a butyl group, more preferably an isopropyl or isobutyl group or tert-butyl group. Most preferably, the enzyme is used to catalyse the hydroxylation of a tert-butyl moiety. The cytochrome P-450 enzyme is able to catalyse the conversion of a substrate compound with a tert-butyl moiety to a hydroxylated-tert-butyl derivative.

In a particularly preferred embodiment, the compound to be hydroxylated is bosentan, diclofenac, tivantinib, buparvaquone, BIRB796 or ritonavir. Most preferably, the compound to be hydroxylated is bosentan, buparvaquone, BIRB796 or ritonavir.

Optionally, one or more additional component(s) may be used to activate the cytochrome P-450 enzyme. In an embodiment according to the present invention, the cytochrome P-450 enzyme is used in combination with reductase components, preferably with ferredoxin and ferredoxin reductase components.

In a preferred embodiment of the invention, the cytochrome P-450 enzyme or variant thereof is present in *Amycolatopsis lurida* (NRRL-2430) cells. The cells may be dosed with the organic compound to be hydroxylated. The method may optionally comprise an additional step wherein the cells are subsequently harvested and purified to obtain the hydroxylated compound.

Culture of the *Amycolatopsis lurida* NRRL-2430 to produce the P-450 enzyme extracts is suitably performed by seeding of a conventional culture medium containing nutrients well-known for use with such microorganisms. Thus, the culture medium contains sources of assimilable carbon and of assimilable nitrogen. The culture medium may also contain inorganic salts. Examples of sources of assimilable carbon include glucose, sucrose, starch, glycerin, millet jelly, molasses and soybean oil. Examples of sources of assimilable nitrogen include soybean solids (such as soybean meal or soybean flour), wheat germ, meat extracts, peptone, corn steep liquor, dried yeast and ammonium salts, such as ammonium sulphate. If required, inorganic salts, such as sodium chloride, potassium chloride, calcium carbonate and various phosphates, may also be included. The medium is preferably sterilized and has a pH adjusted to 5 to 8.

The skilled person will understand that the particular cultivation technique employed is not critical to the invention and any technique commonly used for the cultivation of Actinomycete bacteria may equally be employed with the present invention. In general the techniques employed will be chosen having regard to industrial efficiency. Thus, liquid culture is generally preferred and the submerged culture method is most convenient from the industrial point of view. Cultivation is preferably carried out under aerobic conditions.

The enzymes of this invention are inducible enzymes, and are not produced unless an induction agent is present. For preference, but not limited to, the induction agent is selected to be the same as the intended substrate for the isolated enzyme. When from 4 hours to 3 days have elapsed after inoculation, preferably 0.05 to 5 mM, more preferably 0.2 mM of induction agent is added, and then cultivation is continued for 2 hours to 1 week, preferably for about one day. The temperature of cultivation is typically 20° to 45° C., preferably 25° to 30° C., optimally about 27° C. Shake culture or aeration techniques can be adopted.

The cells obtained by the cultivation may be disrupted by cell disruption techniques such as high-pressure homogenisation in buffer solution. The supernatant obtained by centrifugation gives the crude enzyme solution. For example, the enzyme of the present invention can be obtained in a supernatant produced by centrifugation at 38,000×g for 20 minutes.

In an alternative embodiment, the cytochrome P-450 enzyme or variant thereof is expressed by at least one recombinant microorganism comprising heterologous nucleic acid encoding the enzyme, derived from *Amycolatopsis lurida* (NRRL 2430).

Here, the at least one recombinant microorganism can be dosed with an organic compound to be hydroxylated. This method may optionally comprise a purification step to obtain the hydroxylated compound.

In a preferred embodiment, this can be achieved by the recombinant expression of the functional cytochrome P-450aluC09 protein with intact haem. This can be expressed with any or all of the cofactor enzymes. In a particularly preferred embodiment, ferredoxin and ferredoxin reductase may be expressed.

This can be achieved by polycistronic plasmid use or via fusion-protein, either via linkers or directly into a single protein product.

Alternatively, the functional cytochrome P-450aluC09 protein may be expressed alone without mixing with cofactor enzymes. In a preferred embodiment, cofactor enzymes may be titrated in to provide the active enzyme reaction after material production. The cofactors may be obtained by extraction from wild-type or recombinant materials derived from plants or microbial fermentation. Hussain & Ward., Appl Environ Microbiol. 2003; 69(1):373-382, describe the cloning techniques that may be used.

The native organism, host strain expressing the recombinant enzyme or extracted enzyme is contacted directly with the substrate, preferably in an aqueous medium, either mono, bi or triphasic, with such multiphase systems being either in dispersed or layered form. Reaction conditions, including choice of pH and temperature will be evident to the skilled person, based on conventional techniques. For example, a selected microbial growth medium or phosphate buffer solution at a pH value in the range of from 5 to 12, more preferably 6.5 to 11.0, most preferably around 7.4 may be used. Of particular note is the activity of this recombinant enzyme at elevated pH values e.g., pH value of 11. The ability to catalyse reactions at such a pH affords a particular commercial advantage because increased substrate loading may be achieved for selected substrates with improved solubility at a higher pH, such as compounds with a carboxyl moiety. Other advantages of catalysis at higher pH are the ability to directly utilise the product from a prior step resulting in such products, such as chemical synthesis, base-catalysed hydrolysis of a feedstock, or reaction product from another enzyme where increasing pH has been used to stop that reaction. The reaction temperature is preferably within the range from 10° to 45° C., more preferably from 25° to 30° C. The concentration of the substrate in the reaction medium is preferably within the range from 0.01 to 5.0% by weight. The time allowed for the reaction is normally from 1 minute to 5 days, more usually from 1 hour to 16 hours, although this may vary, depending upon the concentration of substrate in the reaction mixture, the reaction temperature, and other factors. The extracted enzyme material can either be used directly after extraction, after storage in frozen solution. In a particularly preferred embodiment, the extracted enzyme material can be dried, preferably by lyophilisation, for later use with or without the addition of other components required for reaction, such as other enzyme cofactor components.

After completion of the conversion reaction, the hydroxylated compound can be isolated using conventional procedures, including, for instance, filtration, solvent extraction, chromatography, crystallization, and other isolation procedures. Such procedures will be selected having due regard to the identity of the product. Before, during or after the isolation, the product may or may not be derivatised, as desired.

The starting materials as substrates for the enzyme may by either derived from synthetic routes, naturally occurring, either via natural biomass such as plant material, or produced by fermentation, or by mixed routes thereof. Enzyme reactions can also be performed using pure or non-purified materials, the resulting reaction may be used to aid later purifications of reacted or unreacted components.

Of the substrate compounds used as starting materials, free bases, alkali metal salts, e.g. the sodium or potassium salts, or acid salts of organic or inorganic nature such as tosylate or hydrochlorides, are suitable for use.

After completion of the conversion reaction, the desired compound can be obtained from the reaction system, collected, isolated and purified by conventional means if required, or onward used directly in unpurified form. For example, the reaction product is centrifuged or filtered and the supernatant or filtrate is extracted with a hydrophobic resin, ion-exchange resin or water-immiscible organic solvent such as ethyl acetate. After evaporation of the solvent of the extract, the remaining crude hydroxylated compound, for example the remaining crude hydroxylated tert-butyl compound, may be purified by subjecting it to column chromatography using silica gel or alumina or reversed-phase stationary phase, and by eluting with a suitable eluent. If the starting material is a mixture, then the product can be isolated as a mixture of hydroxylated compounds which if desired can be separated using chromatography or other suitable techniques.

In general, the hydroxylated compounds may have improved pharmaceutical or agrochemical properties, such as bioactivity potency, improved solubility characteristics, reduced off-target interactions, or simply of further utility, such as for onward synthesis, or be useful for an analytical standard. Particularly preferred are the hydroxylated compounds of formulas (I) & (II) discussed above.

The present invention is further illustrated with reference to two classes of substrates of markedly different structure, namely aromatic-tBu compounds such as bosentan, and compounds in which the tBu is not directly bonded to an aromatic carbo-cycle system such as buparvaquone.

When the cytochrome P-450 enzyme preparation of this invention is reacted with bosentan as substrate at pH 7.4 for 5 minutes with (a) ferredoxin, (b) ferredoxin-NADP$^+$-reductase, (c) NADP$^+$, (d) NADPH regeneration system, and (e) dissolved oxygen, the temperature of reaction ranges at least from 4° C. to 60° C. The optimum pH for each cytochrome ranges from 6.5 to 11.0. Each cytochrome is stable when kept for 24 hours at 4° C. at pH 7.4.

The use of ferredoxin, ferredoxin-NADP$^+$-reductase, oxygen and NADPH is not essential. Any components which can activate the cytochrome P-450 may be adopted.

Measurement of the enzyme activity is normally effected in one of two ways:

(i) Measurement on Cytochrome P-450$_{aluCO9}$

Measurement is performed according to the method of Omura and Sato et al. (J Biol Chem, 239. 1964, 2370). That is to say, cytochrome P-450$_{aluCO9}$ is analyzed quantitatively using the following formula, based on the difference in the absorbance of the reduced CO versus the reduced difference spectrum at 450 nm and 490 nm.

$$\text{Cytochrome } P450 \text{ (mM)} = \frac{\text{Abs}(450 \text{ nm}) - \text{Abs}(490 \text{ nm})}{91 \text{ (mM cm}^{-1}) \times l(\text{cm})}$$

(ii) Measurement of Rate of Formation of Hydroxy-Bosentan from Bosentan

The following cocktail of components is employed:

| | |
|---|---|
| Potassium phosphate buffer pH 7.4 | 50 mM |
| MgCl$_2$ | 5 mM |
| Enzyme solution containing expressed Fd, FdR, P450 concentration | 2.4 µM in CYP |
| NADP$^+$ | 1 mM |
| Glucose-6-phosphate | 5 mM |
| Glucose-6-phosphate dehydrogenase | 2 UN/ml |
| Bosentan substrate | 0.1 mg/ml |
| Total volume | 0.50 ml |

To measure enzyme activity the components of the table are mixed, the solution is shaken at 30° C. for 16-20 hours, and then 500 µl of acetonitrile is added and the reaction stopped. The amount of hydroxy-bosentan formed by the enzyme system is determined with HPLC or UPLC.

Using the test methods for determining activity, the loss of activity with change in temperature and pH can be determined.

For example, the cytochrome is fully inactivated at pH 7.4 and 70° C. for 60 minutes in the presence of 20% glycerol and 2 mM dithiothreitol. The cytochrome is inactivated at pH 3 or a more acidic pH.

In a further aspect, the invention provides a kit comprising i) a cytochrome P-450 enzyme comprising SEQ ID NO: 3, or a variant enzyme having at least 70% identity thereto and having CYP-450 activity, or ii) a microorganism that expresses a cytochrome P-450 enzyme comprising SEQ ID NO: 3, or a variant enzyme having at least 70% identity thereto and having CYP-450 activity, and wherein the kit further comprises instructions for use for the hydroxylation of an organic compound.

The kit allows the user to screen for the hydroxylation of compounds of interest.

In a preferred embodiment, the kit further comprises electron donating agents. The kit may preferably comprise as the electron donating agents ferredoxin reductase and a ferredoxin with cofactors NADH or NADPH or cofactor regeneration systems such as NAD+ or NADP+, glucose or glucose-6-phosphate, and glucose-dehydrogenase or glucose-6-phosphate dehydrogenase. However, any suitable electron donating agents may be used.

Optionally, the kit may further comprise a buffer, either separately or contained with the other components.

Preferably, the kit may further comprise one or more other CYP-450 enzymes.

Preferably, the cytochrome P-450 enzyme or microorganism is lyophilised or immobilised or tethered to other macromolecules or support materials such alginate beads, Nickel columns and electrochemical electrodes.

The methods of the present invention are demonstrated in the examples below. These examples are provided as an illustration only and should not be construed as limiting on the present invention.

EXAMPLES

Example 1: Production of Hydroxy-Bosentan Using *Amycolatopsis lurida* NRRL-2430 Fermentation Culture medium containing 5 g/L glycerol; 20 g/L glucose; 5 g/L yeast extract peptone; 2 g/L meat extract; 5 g/L mycological peptone; 1 g/L ammonium phosphate dibasic; 3 g/l sodium chloride; 0.3 g/L magnesium sulphate heptahydrate and 3.5 g/L calcium carbonate was prepared and adjusted to pH 7.0. Twelve Erlenmeyer flasks of 250 ml volume, each of which contained 50 ml of the medium, were sterilized at 115° C. for 15 minutes. *Amycolatopsis lurida* NRRL-2430 was recovered from cryo-vial stocks stored in liquid nitrogen and inoculated into two flasks containing 50 ml of the above described growth medium. After 2 days of growth at 27° C. and 200 rpm, the seed cultures (2% v/v) were used to inoculate 10×250 mL Erlenmeyer flasks each containing 50 mL of the above described growth medium. Cultures were fermented at 27° C. and 200 rpm for 24 hours and then 52.7 mg of bosentan was dissolved in 1.05 mL of DMSO; 100 µL of this solution was added to each flask to obtain a final concentration of 100 mg/L bosentan. Cultures were incubated at 27° C. and 200 rpm. After 27 hours the contents of all 10 flasks were combined and extracted twice with 500 mL of ethyl acetate and the resulting extract collected and dried to provide 189.3 mg crude extract.

The extract was dissolved in 2 ml DMSO:MeOH (3:1)), and purified by preparative HPLC as follows: Waters Symmetry Shield RP8 column (19×100 mm) and eluted at a flow rate of 17 ml/min with the following gradient. The gradient started at 90/5/5 (H2O/MeCN/2% formic acid in water) was held for 1 minute then increased to 80/15/5 in one minute, then slowly increased to 55/40/5 over 23.9 minutes, before being further increased to 0/95/5 over one minute (t=26 minutes), held for a further 2 minutes then returned to the starting conditions over 1 minute and re-equilibrated for a further 5 minutes before repeat. The target product eluted between 19 and 20.5 minutes, which upon drying provided 25.2 mg of hydroxylated bosentan product with a purity >95% by LC-UV.

$^1$H NMR (500 MHz, DMSO-d6): 11.31 (1H, s), 9.09 (2H, d, 4.9 Hz), 8.30 (2H, d, 8.2), 7.67 (1H, t, 4.8), 7.53 (2H, d, 8.4), 7.09 (1H, d, 8.1), 7.04 (1H, t, 7.6), 6.81, (1H, t, 7.6), 6.71 (1H, d, 8.0), 4.71 (1H, t, 5.3), 4.67 (1H, t, 5.3), 4.33 (2H, t, 5.4), 3.80 (3H, s), 3.47 (2H, m), 3.42 (2H, d, 4.8), 1.21, 6H, s).

Example 2: Production of Hydroxy-Buparvaquone Using *Amycolatopsis lurida* NRRL-2430 Fermentation Culture medium containing 5 g/L glycerol; 20 g/L glucose; 5 g/L yeast extract peptone; 2 g/L meat extract; 5 g/L mycological peptone; 1 g/L ammonium phosphate dibasic; 3 g/l sodium chloride; 0.3 g/L magnesium sulphate heptahydrate and 3.5 g/L calcium carbonate was prepared and adjusted to pH 7.0. Twelve Erlenmeyer flasks of 250 ml volume, each of which contained 50 ml of this medium, were sterilized at 117° C. for 15 minutes. *Amycolatopsis lurida* NRRL-2430 was recovered from cryo-vial stocks stored in liquid nitrogen and inoculated into two flasks containing 50 ml of the above described growth medium. After 2 days of growth at 27° C. and 200 rpm, the seed cultures (2% v/v) were used to inoculate 10×250 mL Erlenmeyer flasks each containing 50 mL of the above described growth medium. Cultures were fermented at 27° C. and 200 rpm for 24 hours before being dosed with 5 ml per flask of 1 mg/ml buparvaquone in 20% hydroxypropyl-β-cyclodextrin (prepared via 1 in 50 dilution of a stock solution of 52.6 mg buparvaquone in 1 ml DMSO), resulting in a concentration of 105 mg/L. Cultures were time-coursed after dosing to assess the production of the target metabolite hydroxy-buparvaquone. Based on time-course analysis cultures were harvested and extracted after 24 hours.

After culture, the cells were collected by centrifugation. The mass of cells was extracted with MeCN and taken to dryness under vacuum and lyophilization. The supernatant was adsorbed to HP20, washed with water and eluted with MeCN before concentration ready for purification as described below.

PURIFICATION: The combined extract was fractionated over a Waters X-Select C18 column (19×100 mm) and eluted at a flow rate of 20 ml/min with the following gradient. The gradient started at 95/5 (H2O/MeCN (both with 0.1% formic acid)) was held for 2 minutes then increased to 50/50 in 0.2 minutes, then increased to 20/80 over 9.8 minutes, increased to 2/98 over 0.2 minutes, held for a further 2.3 minutes then returned to the starting conditions over 0.1 minute and re-equilibrated for a further 0.4 minutes. The target eluted between 8 and 8.6 minutes, which upon drying provided 14.0 mg of hydroxylated buparvaquone product with a purity >95% by LC-UV.

$^1$H NMR (500 MHz, DMSO-d6): 7.96 (2H, t, 7.6 Hz), 7.81 (1H, td, 7.5, 1.4), 7.75 (1H, td, 7.5, 1.4), 4.31 (1H, t, 5.4), 3.11 (2H, d, 4.1), 2.36 (2H, d, 7.0), 1.68 (2H, m), 1.63 (2H, m), 1.46 (1H, m), 1.16 (1H, m), 0.90 (4H, m), 0.70 (6H, s).

Example 3: Production of Hydroxy-Ritonavir Using *Amycolatopsis lurida* NRRL-2430 Fermentation Culture medium containing 5 g/L glycerol; 20 g/L glucose; 5 g/L yeast extract peptone; 2 g/L meat extract; 5 g/L mycological peptone; 1 g/L ammonium phosphate dibasic; 3 g/l sodium chloride; 0.3 g/L magnesium sulphate heptahydrate and 3.5 g/L calcium carbonate was prepared and adjusted to pH 7.0. Forty two Erlenmeyer flasks of 250 ml volume, each of which contained 50 ml of the medium, were sterilized 115° C. for 15 minutes. *Amycolatopsis lurida* NRRL-2430 was recovered from cryo-vial stocks stored in liquid nitrogen and inoculated into two flasks containing 50 ml of the above described growth medium. After 2 days of growth at 27° C. and 200 rpm, the seed cultures (2% v/v) were used to inoculate 40×250 mL Erlenmeyer flasks each containing 50 mL of the above described growth medium. Cultures were fermented at 27° C. and 200 rpm for 24 hours before being dosed with ritonavir at a concentration of 100 mg/L. Ritonavir was formulated before being dosed, as described for buparvaquone in Example 2, above. Cultures were time-coursed daily after dosing to assess the production of the target metabolite hydroxy-ritonavir. Based on time-course analysis cultures were harvested and extracted after 72 hours.

After culture, the cells were collected by centrifugation. The mass of cells was extracted with MeCN and taken to dryness under vacuum and lyophilization. The supernatant was adsorbed to HP20, washed with water and eluted with MeCN.

PURIFICATION: The combined extracts were fractionated over a Waters Novapak C18 column (40×100 mm)+ guard column (40×10 mm) at a flow rate of 50 ml/min and a gradient starting at 90/5/5% (H2O/MeCN/200 mM ammonium formate+2% formic acid in water), holding for 1.1 minutes, then increasing to 45/50/5 at 17 minutes, increased again to 0/95/5 over 1 minute, washed for 4 minutes, returned to start conditions over 1 minutes and re-equilibrated over 4 minutes. The impure target hydroxyl-ritonavir eluted between 16.0 and 17.5 minutes.

The target product was then purified over a Waters Symmetry Shield RP8 column (19×100 mm) and eluted at a flow rate of 17 ml/min with the following gradient. The gradient started at 90/5/5 (H2O/MeCN/2% formic acid in MeCN) was held for 1 minute then increased to 60/30/5 in one minute and held for a further 20 minutes then increased to 0/95/5 over 2 minutes, held for a further 2 minutes then returned to the starting conditions over 1 minute and re-equilibrated for a further 4 minutes. The target eluted between 13 and 14 minutes, which upon drying provided 21.5 mg of hydroxylated ritonavir product with a purity >95% by LC-UV.

$^1$H NMR (500 MHz, DMSO-d6): 9.05 (1H, s), 7.85 (1H, s), 7.70 (1H, d, 8.4), 7.16 (14H, m), 6.87 (1H, d, 9.4), 6.01 (1H, d, 8.7), 5.91 (1H, s), 5.15 (2H, m), 4.62 (1H, d, 6.3), 4.42 (2H, s), 4.14 (1H, m), 3.92, 1H, dd, 8.7, 7.7), 3.82 (1H, q, 9.3), 3.58 (1H, q, 8.8), 2.86 (3H, s), 2.67 (2H, m), 2.62 (2H, m), 1.88 (1H, m), 1.49 (3H, s), 1.48 (3H, s), 1.45 (1H, m), 0.77 (1H, m), 0.74 (6H, d, 6.8).

The isopropyl methyls at 1.49 and 1.48 ppm are now singlets following hydroxylation at the bridging methine position.

Example 3a: Production of Hydroxylated Tivantinib Metabolites Using *Amycolatopsis lurida* NRRL-2430 Fermentation Culture medium containing 5 g/L glycerol; 20 g/L glucose; 5 g/L yeast extract peptone; 2 g/L meat extract; 5 g/L mycological peptone; 1 g/L ammonium phosphate dibasic; 3 g/l sodium chloride; 0.3 g/L magnesium sulphate heptahydrate and 3.5 g/L calcium carbonate was prepared and adjusted to pH 7.0. Forty Erlenmeyer flasks of 250 ml volume, each of which contained 50 ml of the medium, were sterilized at 115° C. for 15 minutes. *Amycolatopsis lurida* NRRL-2430 was recovered from cryo-vial stocks stored in liquid nitrogen and inoculated into two flasks containing 50 ml of the above described growth medium. After 2 days of growth at 27° C. and 200 rpm, the seed cultures (2% v/v) were used to inoculate 40×250 mL Erlenmeyer flasks each containing 50 mL of the above described growth medium. Cultures were fermented at 27° C. and 200 rpm for 24 hours and then tivantinib was dissolved in DMSO and added to each flask to obtain a final concentration of 100 mg/L tivantinib. Cultures were incubated at 27° C. and 200 rpm. After 72 hours the contents of all 40 flasks were combined and centrifugated. The mass of cells was extracted with MeCN (1.5 L) and concentrated by rotary evaporation. The aqueous broth supernatant was adsorbed to HP20 (500 ml), washed with water, eluted with MeCN (1.5 L) and concentrated by rotary evaporation. The HP20 and cell extract concentrates were combined (500 ml) and extracted with ethyl acetate (3×500 ml). The combined ethyl acetate layers were rotary evaporated to dryness and the resulting material partitioned between acetonitrile-H2O (9:1, 500 ml) and hexane (500 ml). The hexane layer was discarded and the acetonitrile layer concentrated to dryness. This material was fractionated by reversed phase HPLC using a Waters Novapak C18 column (40×100 mm)+guard column (40×10 mm) at a flow rate of 50 ml/min and a gradient starting at 90/5/5% (H2O/MeCN/200 mM ammonium formate+2% formic acid in water), holding for 1.1 minutes, then increasing linearly to 15/80/5 over the next 10 minutes, increased again to 0/95/5 over 1 minute, washed for 2 minutes, returned to start conditions over 1 minute and re-equilibrated over 5 minutes. Fractions containing monohydroxylated metabolites were found to have eluted between 6.5 and 8.0 minutes (fractions 14-16) and these were concentrated to dryness for further purification.

Fraction 14 was further purified using a Waters X-Select C18 column (19×100 mm) and eluted at a flow rate of 20 ml/min with the following gradient. The gradient started at 95/5 (10 mM aqueous ammonium bicarbonate/MeCN) was held for 2 minutes then increased to 75/25 in 0.1 minutes and held at this composition for a further 14.9 minutes, then increased to 95/5 over 0.1 minutes, held for a further 1 minute then returned to the starting conditions over 0.1 minute and re-equilibrated for a further 0.9 minutes. The peaks eluting between 13-14 minutes and 14-15 minutes were separately collected and concentrated to dryness to yield 19.0 and 6.8 mg respectively of compounds identified by NMR as tivantinib metabolites M4 and M5 (T. Murai et al. (2014) Metabolism and disposition of [$^{14}$C]tivantinib after oral administration to humans, dogs and cats. Xenobiotica 44: 996-1008), although it was not possible to distinguish the two epimers.

$^1$H NMR (500 MHz, DMSO-d6):

First metabolite: 11.45 (1H, bs), 11.03 (1H, d, 2.8 Hz), 7.41 (1H, d, 7.8 Hz), 7.38 (1H, d, 2.5 Hz), 7.36 (1H, d, 8.4 Hz), 7.36 (1H, s), 7.27 (1H, d, 8.0 Hz), 7.08 (1H, ddd, 8.2, 7.1, 1.1 Hz), 7.05 (1H, d, 7.1 Hz), 6.96 (1H, d, 8.0 Hz), 6.95 (1H, t, 7.7 Hz), 5.34 (1H, d, 5.4 Hz), 4.89 (1H, q, 5.1 Hz), 4.53 (1H, d, 7.0 Hz), 4.48 (1H, d, 7.0 Hz), 4.14 (2H, m), 2.11 (2H, m).

Second metabolite: 11.51 (1H, bs), 11.02 (1H, d, 2.9 Hz), 7.41 (1H, d, 7.9 Hz), 7.37 (1H, d, 2.7 Hz), 7.36 (1H, m), 7.35 (1H, s), 7.27 (1H, d, 8.2), 7.08 (1H, ddd, 8.1, 7.0, 1.1 Hz), 7.05 (1H, d, 7.1 Hz), 6.96 (1H, t, 7.8 Hz), 6.94 (1H, t, 8.0 Hz), 5.34 (1H, q, 5.3 Hz), 4.90 (1H, d, 5.2 Hz), 4.51 (1H, d, 6.9 Hz), 4.48 (1H, d, 7.0 Hz), 4.14 (2H, m), 2.11 (2H, m).

Fraction 15 was further purified using a Waters Xbridge phenyl column (19×100 mm) eluted at a flow rate of 20 ml/minute with the following gradient: starting at 95/5 (0.1% aqueous ammonia/MeCN), this composition was held for 2.5 minutes then linearly increased to 5/95 over the next 7.5 minutes and held at this composition for a further 0.9 minutes, before returning to the starting conditions over 0.1 minute and re-equilibrating for a further 1.0 minutes. The peak eluting between 6.0 and 6.5 minutes was collected and concentrated to dryness to yield 6.6 mg of tivantinib metabolite M7 (T. Murai et al. (2014) Metabolism and disposition of [$^{14}$C]tivantinib after oral administration to humans, dogs and cats. Xenobiotica 44: 996-1008) as identified by NMR spectroscopy.

$^1$H NMR (500 MHz, DMSO-d6): 11.38 (1H, bs), 10.61 (1H, d, 2.4 Hz), 8.93 (1H, bs), 7.31 (1H, s), 7.17 (1H, d, 7.5 Hz), 7.16 (1H, d, 8.5 Hz), 7.13 (1H, d, 2.1 Hz), 6.88 (1H, t, 7.4 Hz), 6.84 (1H, d, 6.8 Hz), 6.71 (1H, d, 2.1 Hz), 6.49 (1H, dd, 8.5, 2.2 Hz), 4.44 (1H, d, 6.7 Hz), 4.35 (1H, d, 6.7 Hz), 4.10 (2H, dd, 6.6, 4.6 Hz), 2.90 (2H, t, 6.0 Hz), 2.10 (2H, dt, 11.1, 5.6 Hz).

Fraction 16 was further purified purified using a Waters Xbridge phenyl column eluted at a flow rate of 20 ml/min with the following gradient. The gradient started at 95/5 (0.1% aqueous ammonia/MeCN), was held for 2 minutes then increased to 85/15 in 0.1 minutes and then linearly increased to 75/25 Over the next 7.9 minutes, then increased to 95/5 over 0.1 minutes, held for a further 0.8 minute then returned to the starting conditions over 0.1 minute and re-equilibrated for a further 1.0 minutes. The peak eluting between 5.7 and 6.3 minutes was collected and concentrated to dryness to yield 0.6 mg of a compound which may be tivantinib metabolite M9 (T. Murai et al. (2014) Metabolism and disposition of [$^{14}$C]tivantinib after oral administration to humans, dogs and cats. Xenobiotica 44: 996-1008) as identified by NMR spectroscopy.

$^1$H NMR (500 MHz, DMSO-d6): 11.06 (1H, d, 2.5 Hz), 7.32 (1H, s), 7.24 (1H d 2.6 Hz), 7.16 (1H, d, 7.8 Hz), 6.88 (1H, t, 7.4 Hz), 6.84 (1H, d, 7.2 Hz), 6.82 (1H, d, 8.0 Hz), 6.75 (1H, t, 7.7 Hz), 6.49 (1H, d, 7.4 Hz), 4.47 (1H, d, 6.8 Hz), 4.41 (1H, d, 6.8 Hz), 4.09 (2H, t, 5.7 Hz), 2.90 (2H, t, 6.0 Hz), 2.11 (2H, p, 5.6 Hz).

Example 3b: Production of Hydroxylated Diclofenac Metabolites Using *Amycolatopsis lurida* NRRL-2430 Fermentation Culture medium containing 5 g/L glycerol; 20 g/L glucose; 5 g/L yeast extract peptone; 2 g/L meat extract; 5 g/L mycological peptone; 1 g/L ammonium phosphate dibasic; 3 g/l sodium chloride; 0.3 g/L magnesium sulphate heptahydrate and 3.5 g/L calcium carbonate was prepared and adjusted to pH 7.0. Twenty Erlenmeyer flasks of 250 ml volume, each of which contained 50 ml of the medium, were sterilized at 115° C. for 15 minutes. *Amycolatopsis lurida* NRRL-2430 was recovered from cryo-vial stocks stored in liquid nitrogen and inoculated into two flasks containing 50 ml of the above described growth medium. After 2 days of growth at 27° C. and 200 rpm, the seed cultures (2% v/v) were used to inoculate 20×250 mL Erlenmeyer flasks each containing 50 mL of the above described growth medium. Cultures were fermented at 27° C. and 200 rpm for 24 hours and then diclofenac dissolved in DMSO was added to each flask to obtain a final concentration of 100 mg/L diclofenac. Cultures were incubated at 27° C. and 200 rpm. After 22 hours the contents of all 20 flasks were combined and centrifuged to separate the aqueous supernatant from the cells. The cells were extracted with acetonitrile (900 ml) for 1 hour and then centrifuged again to collect the acetonitrile extract. This was mixed with the aqueous broth supernatant and ammonium sulphate (132 g) added. The mixture was stirred until 2 phases separated. The acetonitrile layer was collected and rotary evaporated to yield an aqueous concentrate. This material was fractionated by reversed phase HPLC using a Waters Symmetry Shield RP8 column (19× 100 mm) and eluted at a flow rate of 17 ml/min with the following gradient. The gradient started at 55/45/5 (H2O/

MeCN/200 mM ammonium acetate+2% formic acid in H$_2$O) and increased linearly to 45/50/5 over 10 minutes and held for a further 20 minutes at this concentration before returning to the starting conditions. The eluate was monitored at 280 nm and the peaks eluting at 6.5 and 9 minutes were collected and concentrated to dryness to yield 5-hydroxydiclofenac (11.6 mg) and 4'-hydroxydiclofenac (12.4 mg), respectively.

$^1$H NMR (500 MHz, DMSO-d6):

5-hydroxydiclofenac: 7.43 (2H, d, 8.1 Hz), 7.03 (1H, t, 8.1 Hz), 6.65 (1H, d, 2.8 Hz), 6.49 (1H, dd, 8.5, 2.8 Hz), 6.25 (1H, d, 8.5), 3.57 (2H, s).

4'-hydroxydiclofenac: 7.03 (1H, dd 7.5, 1.6 Hz), 6.92 (2H, s), 6.90 (1H, dd, 7.6, 1.6 Hz), 6.66 (1H, td, 7.4, 1.2 Hz), 6.08 (1H, dd, 8.0, 1.2 Hz), 3.43 (2H, s).

Example 4: Cloning of P450$_{aluC09}$ and Ferredoxin$_{aluF03}$ Extraction of Genomic DNA from *Amycolatopsis lurida* NRRL 2430

Genomic DNA (gDNA) was isolated from cell pellet of fermentation material of *Amycolatopsis lurida* NRRL 2430. Culture medium containing 4 g/L yeast extract; 10 g/L malt extract; 4 g/L glucose and adjusted to pH 7.0. Two Erlenmeyer flasks of 250 ml volume, each of which contained 50 ml of the medium, were sterilized 115° C. for 20 minutes. *Amycolatopsis lurida* (NRRL-2430) was recovered from cryo-vial stocks stored in liquid nitrogen and inoculated into the two flasks containing 50 ml of the above growth medium. After 2 days of growth at 27° C. and 200 rpm, 50 mls of culture were transferred to 50 ml centrifuge tubes and centrifuged to collect the pelleted cells. The pellet was washed once with an isotonic buffer to remove residual medium components before freezing the pellet at −80° C. for later extraction of genomic DNA as described below. The cell pellet was defrosted and resuspended in 7.5 ml TE buffer (10 mM Tris-HCl pH 7.5, 1 mM Na$_2$EDTA). Seventy-five µl of 20 mg/ml lysozyme solution was added and the solution was incubated at 37° C. for 1 hour, followed by addition of 750 µl of 10% (w/vol) SDS and mixing by inverting. After addition of 20 µl of 20 mg/ml pronase and incubation at 37° C. for 1.5 hours, the solution was supplemented with 16 µl of 10 mg/ml RNase solution, followed by another incubation step at 37° C. for 1 hour and 50° C. for 1 hour. Nine hundred µl of 0.5 M NaCl solution was added before the solution was extracted twice with an equal volume of phenol-chloroform-isoamylalcohol (25:24:1; Sigma-Aldrich). The aqueous layers were collected and gDNA was precipitated with 1 volume of isopropanol and centrifugation (10,000×g, 30 min, 20° C.). The gDNA pellet was washed once with 100% ethanol and twice with 70% ethanol (~30 ml each wash step). The gDNA pellet was air-dried and resuspended in 5 ml TE buffer. Concentration and purity of the gDNA was measured using a NanoDrop instrument (Thermo Scientific) and gDNA integrity was assessed by agarose gel electrophoresis.

PCR Reactions

The DNA sequence encoding the operon composed of P450$_{aluC09}$ (GenBank: AJK52184.1; Uniprot Accession: A0A093BCG8, Locus tag: BB31_01535) and ferredoxin$_{aluF03}$ (GenBank: AJK52183.1; UniProt Accession: A0A093BIZ3, Locus tag: BB31_01530), including intergenic region, was amplified from genomic DNA by PCR using the primers aluC09-F03_f (5'-primer sequence-3': gtttaactttaagaaggagatataCATATGACTGACGTCGAGGA-AACCAC) (SEQ ID NO: 5) and aluC09-F03_r (5'-primer sequence-3': gagggcggggcatAAGCTTCCTATTAAGCG-AGCGACAAGG) (SEQ ID NO: 6) in a total reaction volume of 50 µl. PCR reactions contained 10 µl of 5×HF buffer, 1.5 µl of DMSO, 1 µl of 10 mM of dNTPs, 0.5 µl of Phusion® High-Fidelity DNA Polymerase (1 unit; New England Biolabs), ~90 ng of genomic DNA, 0.5 µM of each forward and reverse primer and the reaction was filled up to a total volume of 50 µl with MilliQ®-H$_2$O. PCR reactions were performed on a Biorad C1000 Touch™ thermal cycler system with the following cycling conditions: 98° C. for 30 seconds, 35 cycles (98° C. for 10 seconds, 57° C. for 15 seconds, 72° C. for 45 seconds), 72° C. for 5 minutes. The expected size of the PCR amplicon was 1468 bp.

The DNA sequence encoding the plasmid backbone pQR368bb was amplified from plasmid pQR368 (Hussain & Ward. Appl Environ Microbiol. 2003; 69:373-82) by PCR using the primers pQR368_bbSCF15a_f (5'-primer sequence-3': taataggAAGCTTATGCCCCGCCCTCTGC-GGG) (SEQ ID NO: 7) and pQR368_bbSCF15a_r (5'-primer sequence-3': gccgccCATATGTATATCTCCTTCT-TAAAGTTAAAC) (SEQ ID NO: 8) in a total reaction volume of 50 µl. PCR reactions contained 10 µl of 5×HF buffer, 1.5 µl of DMSO, 1 µl of 10 mM of dNTPs, 0.5 µl of Phusion® High-Fidelity DNA Polymerase (1 unit), 15 ng of plasmid DNA pQR368, 0.5 µM of each forward and reverse primer and the reaction was filled up to a total volume of 50 µl with MilliQ®-H$_2$O. PCR reactions were performed on a Biorad C1000 Touch™ thermal cycler system with the following cycling conditions: 98° C. for 30 seconds, 35 cycles (98° C. for 10 seconds, 56° C. for 15 seconds, 72° C. for 3 minutes 25 seconds), 72° C. for 10 minutes. The expected size of the PCR amplicon was 6768 bp.

All PCR reactions were analysed by agarose gel electrophoresis and PCR products were extracted from the agarose gel using the QIAquick® Gel Extraction Kit (Qiagen). DNA concentrations of the purified PCR products were measured using the NanoDrop instrument (Thermo Scientific).

Cloning of P450aluC09-aluF03

The P450$_{aluC09}$-ferredoxin$_{aluF03}$ operon was cloned into the vector backbone pQR368bb by circular polymerase extension cloning (CPEC; Quan & Tian. Nat Protoc. 2011; 6:242-51).

Prior to CPEC, the pQR368bb amplicon was digested with restriction endonuclease NdeI to remove the 5' overhang introduced by primer pQR368_bbSCF15a_r. Restriction digestion was carried out for 4 h at 37° C. in a total volume of 100 µl containing 10 µl of 10× CutSmart Buffer®, 1.5 µl of NdeI (30 units; New England Biolabs), ~1.7 µg of pQR368bb PCR product and the reaction was filled up with MilliQ®-H$_2$O to 100 µl. The reaction was stopped by inactivation of NdeI at 65° C. for 20 min. The digested pQR368bb PCR product was purified using the QIAquick®PCR Purification Kit (Qiagen).

CPEC of the P450$_{aluC09}$-ferredoxin$_{aluF03}$ operon into pQR368bb was done in total reaction volume of 20 µl containing 4 µl of 5×HF buffer, 0.6 µl of DMSO, 1.6 µl of 10 mM dNTPs, 104 ng of pQR368bb vector backbone, 43 ng of P450$_{aluC09}$-ferredoxin$_{aluF03}$ PCR product and 0.2 µl of Phusion® High-Fidelity DNA Polymerase (0.4 units). OPEC reactions were performed on a Biorad C1000 Touch™ thermal cycler system with the following cycling conditions: 98° C. for 30 seconds, 5 cycles (98° C. for 10 seconds, 50° C. for 30 seconds, 72° C. for 2 minutes 45 seconds), 72° C. for 5 minutes. Four µl of the CPEC reaction were used to transform 50 µl chemically competent *E. coli* DH5α cells. Clones were selected on lysogeny broth (LB) plates containing 100 µg/ml ampicillin after 12-16 hours of incubation at 37° C. Clones were picked and cultivated in 5 ml LB containing 100 µg/ml ampicillin for 12-16 hours at 37° C. and 250 rpm. Recombinant plasmids were isolated from these cultures using the QIAprep® Spin Miniprep Kit (Qiagen) and analysed by restriction digest with appropriate enzymes.

DNA Sequencing and Analysis

DNA sequences of the cloned $P450_{aluC09}$-ferredoxin$_{aluF03}$ operon and the reductase part of the pQR368bb vector backbone were confirmed by Sanger sequencing at Eurofins Genomics (Germany). The constructed plasmid was designated as pQR368bb-aluC09-aluF03.

Construction of the Recombinant Expression Strain

The strain E. coli BL21 Star (DE3) pLysS (Invitrogen) was used as a host for recombinant expression of $P450_{aluC09}$, ferredoxin$_{aluF03}$ and ferredoxin reductase$_{SCF15A}$. To construct this expression strain, E. coli BL21 Star (DE3) pLysS cells were transformed with plasmid pQR368bb-aluC09-aluF03 using the heat shock procedure. Fifty µl chemically competent cells were mixed with 0.5 µl (68 ng) of plasmid pQR368bb-aluC09-aluF03 followed by incubation on ice for 50 min. Heat shock was performed for 45 sec in a water bath at 42° C. and cells were subsequently chilled on ice for approximately 2 min. After addition of 800 µl LB, cells were incubated for 1.5 h at 37° C. and 500 rpm in a Thermoshaker (Eppendorf). One µl of this mixture was mixed with 50 µl LB and plated on LB plates containing 100 µg/ml ampicillin and 34 µg/ml chloramphenicol. Plates were incubated at 37° C. for approximately 14 hours.

To prepare glycerol stocks of this expression strain, a single colony was picked and inoculated into 5 ml LB containing the same antibiotics and cultivated at 37° C. and 250 rpm for approximately 14 h. Five hundred µl of this culture were mixed with 500 µl 50% (vol/vol) glycerol in cryovials and stored at −80° C.

Example 5: Expression of Recombinant AluC09-AluF03

Transformation/Agar plates plate LB-Agar was supplemented with 100 µg/ml of Ampicillin and 25 µg/ml of chloramphenicol by streaking it with E. coli BL21 Star (DE3) pLysS harbouring plasmid pQR368bb-aluC09-aluF03 from a 50% glycerol frozen stock and incubate at 37° C. overnight.

Seeding: 5 ml of LB Miller media supplemented with 34 µg/ml of chloramphenicol and 100 µg/ml of ampicillin was inoculated with a single colony of E. coli BL21 Star(DE3) pLysS/pQR368bb-aluC09-aluF03 from an agar plate made as describe above. Cells were grown overnight at 37° C. and 200 rpm Inoculation: Into a 250 ml baffled flask, 50 ml of Terrific Broth media supplemented with 34 µg/ml of chloramphenicol with 100 µg/ml of ampicillin was inoculated with 0.5 ml of the seeding culture and then growth cells at 37° C. and 200 rpm until OD(600) reaches 0.6-0.8. At this point, gene expression was induced by adding IPTG to reach the final concentration of 0.1 mM and the culture was further supplemented with $FeSO_4$ and 5'-aminolevulinic acid to reach the concentration of 0.1 mM and 80 µg/ml of respectively. Induced cells were grown at 27° C. and 140 rpm for a further four hours and then the culture was harvested by centrifugation.

Example 6: Extraction & Processing of Enzyme Materials

Suspended cell pellets were provided as described in Example 5, containing recombinant $P450_{aluC09}$, ferredoxin$_{aluF03}$ and ferredoxin reductase$_{SCF15A}$ in 50 mM potassium phosphate buffer pH 7.4, 5 mM $MgCl_2$, 0.1 mM DTT, and 1 mM PMSF in a ratio of 15 ml of buffer per 1 g of cells. Lysed cells were produced by high pressure disruption using three cycles of 30 kpsi. Lysed material was centrifuged at 38,000×g for 30 minutes (4° C.) and the supernatant was sterilized by passing through 0.22 micron filter to provide the enzyme preparation containing 2.9 µM of recombinant $P450_{aluC09}$ and 919 UN of recombinant ferredoxin reductase. The crude extract was then dispensed into glass vials (0.5 ml per 2 ml vial), frozen and lyophilised using an Edwards Supermodulyo Freeze-dryer before being stored in a standard laboratory freezer at −20° C. until required for use.

Example 7: Hydroxylase Activity/Spectrum Testing

Lyophilised material of recombinant $P450_{aluC09}$, ferredoxin$_{aluF03}$ and ferredoxin reductase$_{SCF15A}$ was made as described in examples 5 and 6 and suspended in water to a final concentration of 2.9 µM of $P450_{aluC09}$ and 919 UN of ferredoxin reductase$_{SCF15A}$. Biocatalysis was performed at 30° C. in the following conditions: 50 mM potassium phosphate pH 7.4, 5 mM $MgCl_2$, 0.1 mg/ml substrate compound such as bosentan (CarboSynth Ltd, UK), buparvaquone (MedChemtronica, Sweden), BIRB796 (Stratech Scientific Limited, UK), diclofenac (Sigma-Aldrich, UK), epothilone B (LC Laboratories, USA) or ritonavir (TCI, UK), tivantinib (MedChemtronica, Sweden), 2.4 µM of $P450_{AluC09}$, 767 UN of ferredoxin reductase$_{SCF15A}$, 5 mM G6P, 1 mM NADP, 2 UN/ml G6PDH in a final volume of 100 µL. After 16-20 hours, reactions were extracted with an equal volume of acetonitrile, centrifuged to remove precipitated proteins and conversion assessed by UPLC-MS analysis.

UPLC data was obtained as follows:

Column: Acquity UPLC BEH Shield RP18 1.7 µm 2.1 mm i.d. 50 mm length

Solvents: $H_2O$, B: Acetonitrile, both with 0.1% Formic acid

Flow rate: 1.0 ml/min

Detector: Waters Acquity UPLC PDA (UV-Vis detection) and Waters Acquity UPLC QDA (MS)

Retention time: Bosentan substrate: 1.75 minutes; hydroxylated bosentan: 1.42 minutes The chromatographic retention and mass spectrum coincided with that for an authentic sample.

Example 8: Influence of Solution pH on Hydroxylase Activity

Figure 10:
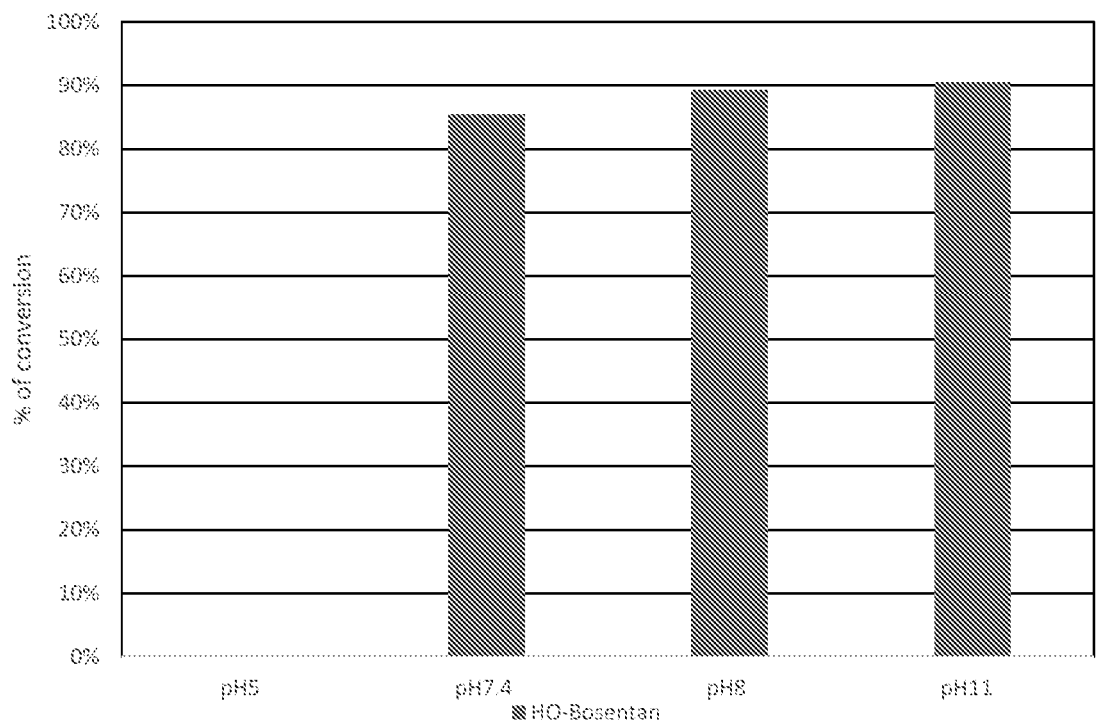
FIG. 10. Shows the percentage yield of hydroxy-bosentan product obtained from cell-free activity testing of lyophisised enzyme preparation at different reaction pHs.
Figure 11:
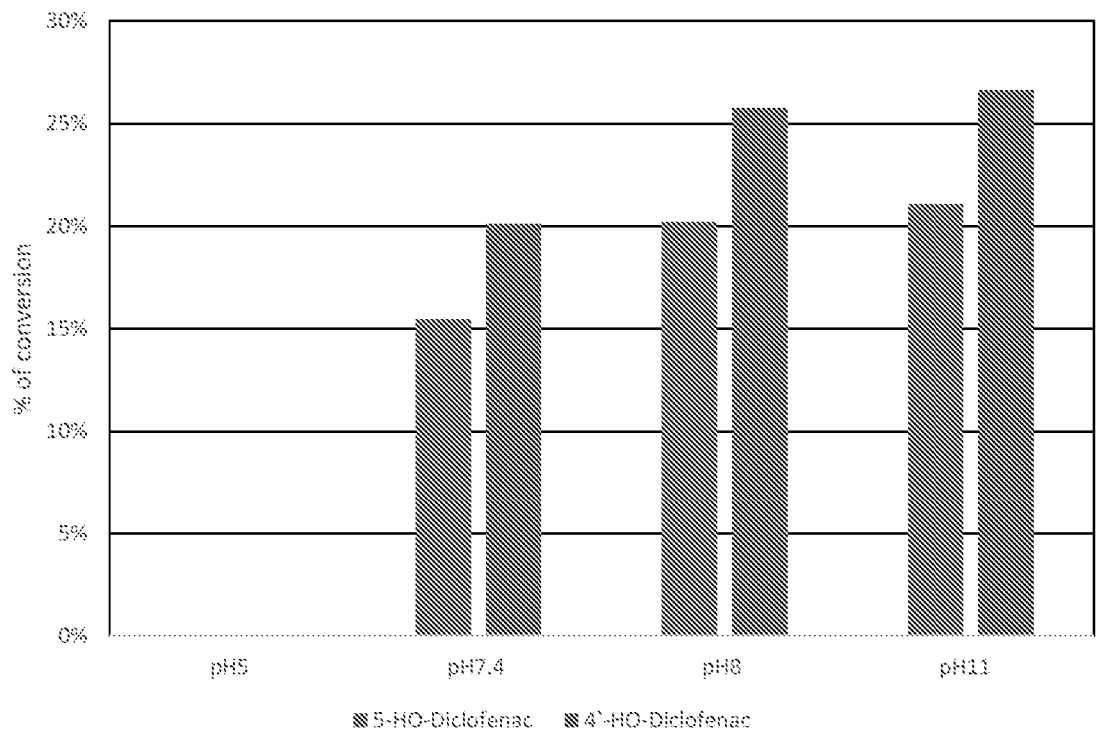
FIG. 11. Shows the percentage yield of 5-hydroxy- and 4'-hydroxy-diclofenac products obtained from cell-free activity testing of lyophilised enzyme preparation and different reaction pHs.
Figure 12:
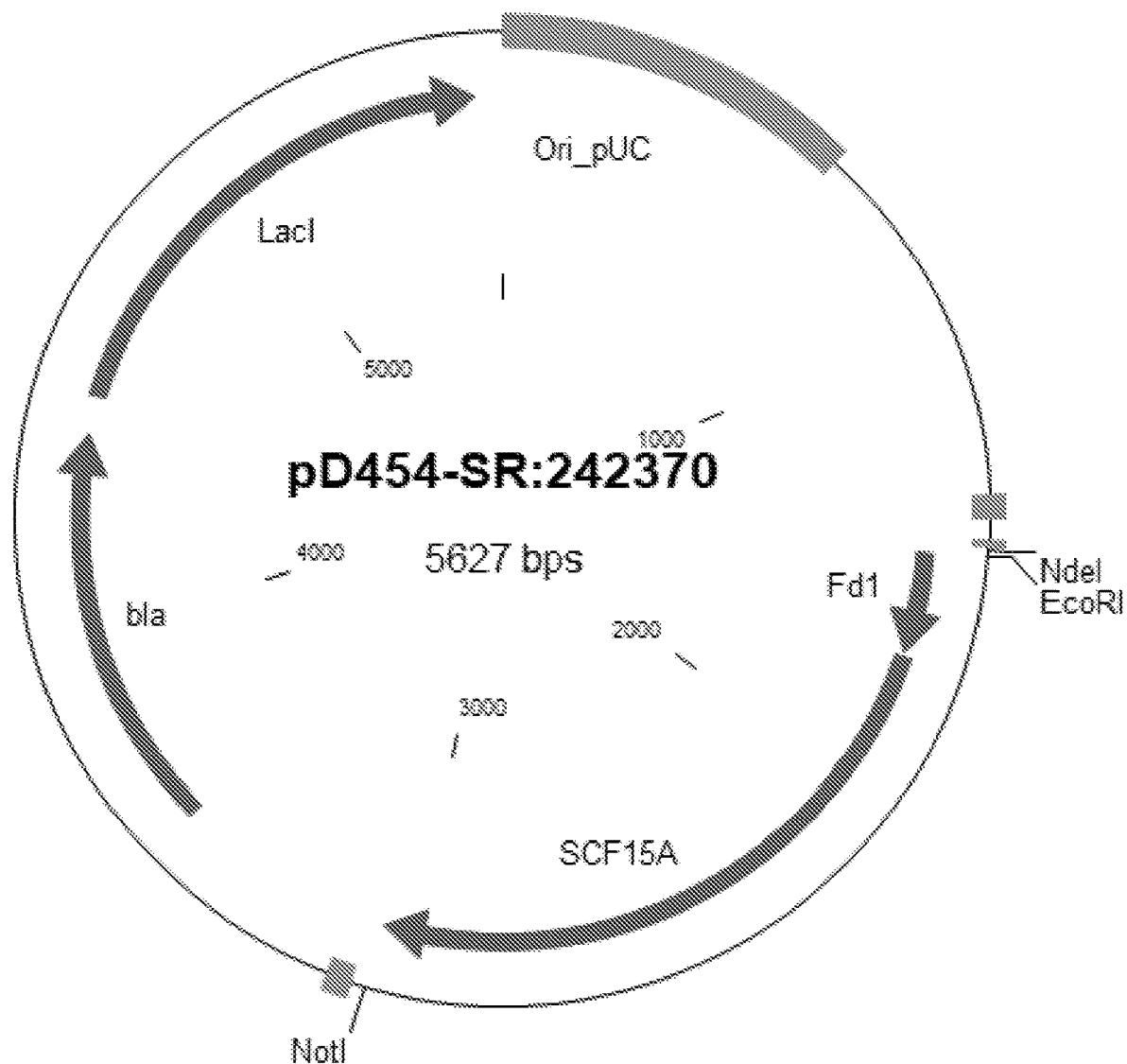
FIG. 12. shows expression vector pD454-SR:242370
Figure 13:
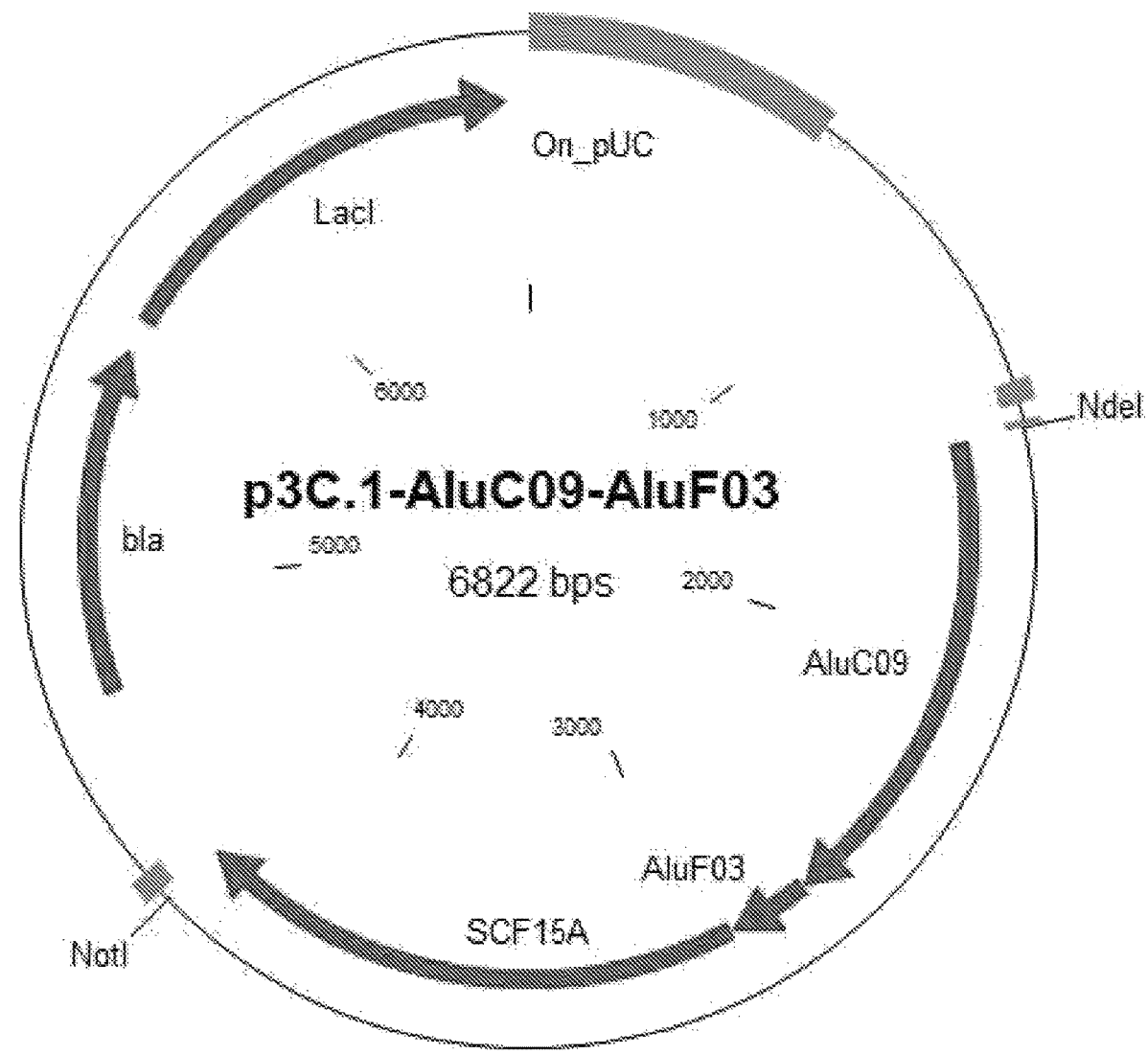
FIG. 13. Shows expression vector p3C.1-AluC09-AluF03
Figure 14:
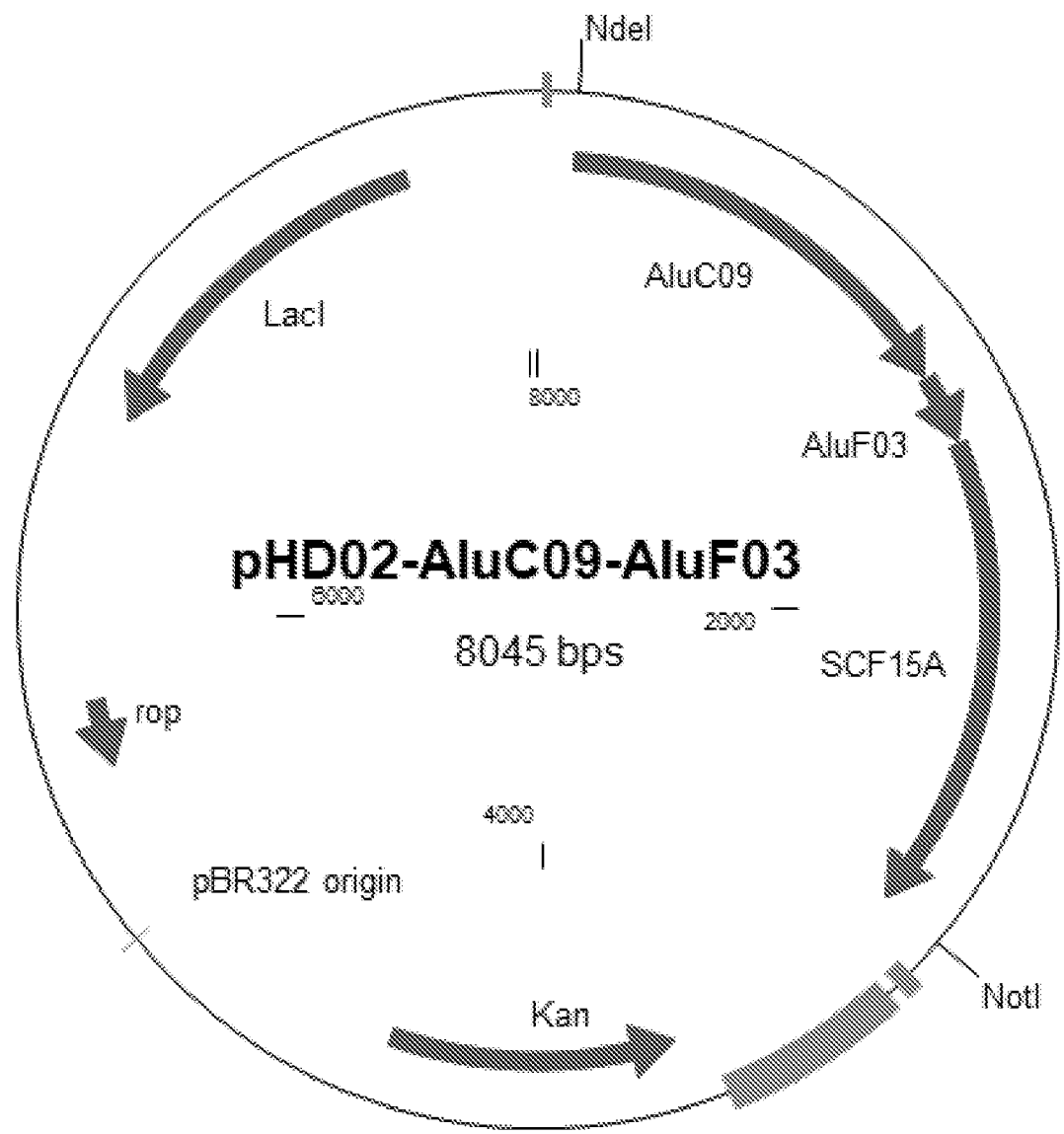
FIG. 14. Shows expression vector pHD02-AluC09-AluF03
Figure 15:
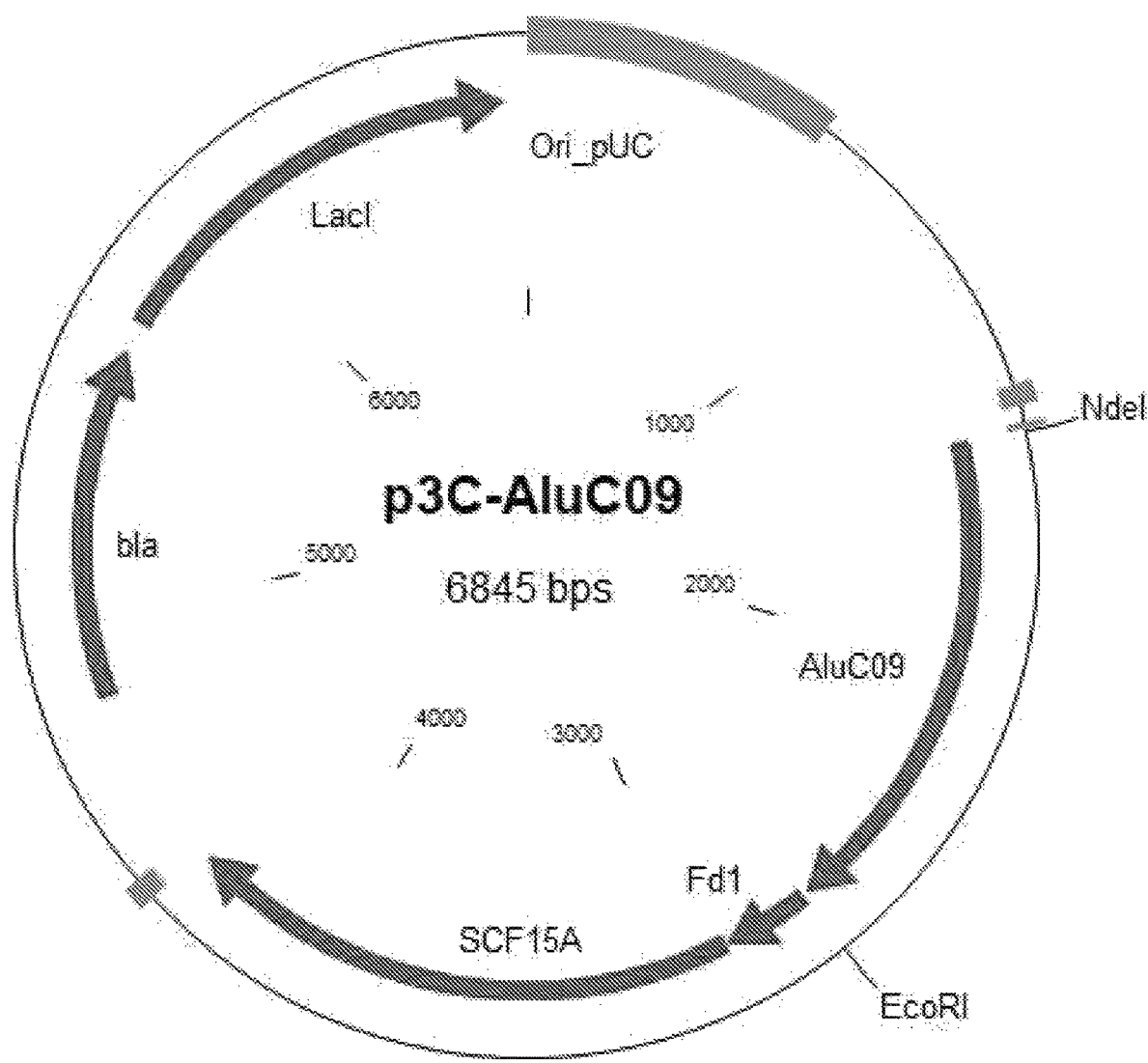
FIG. 15. Shows expression vector p3C-AluC09
Figure 16:
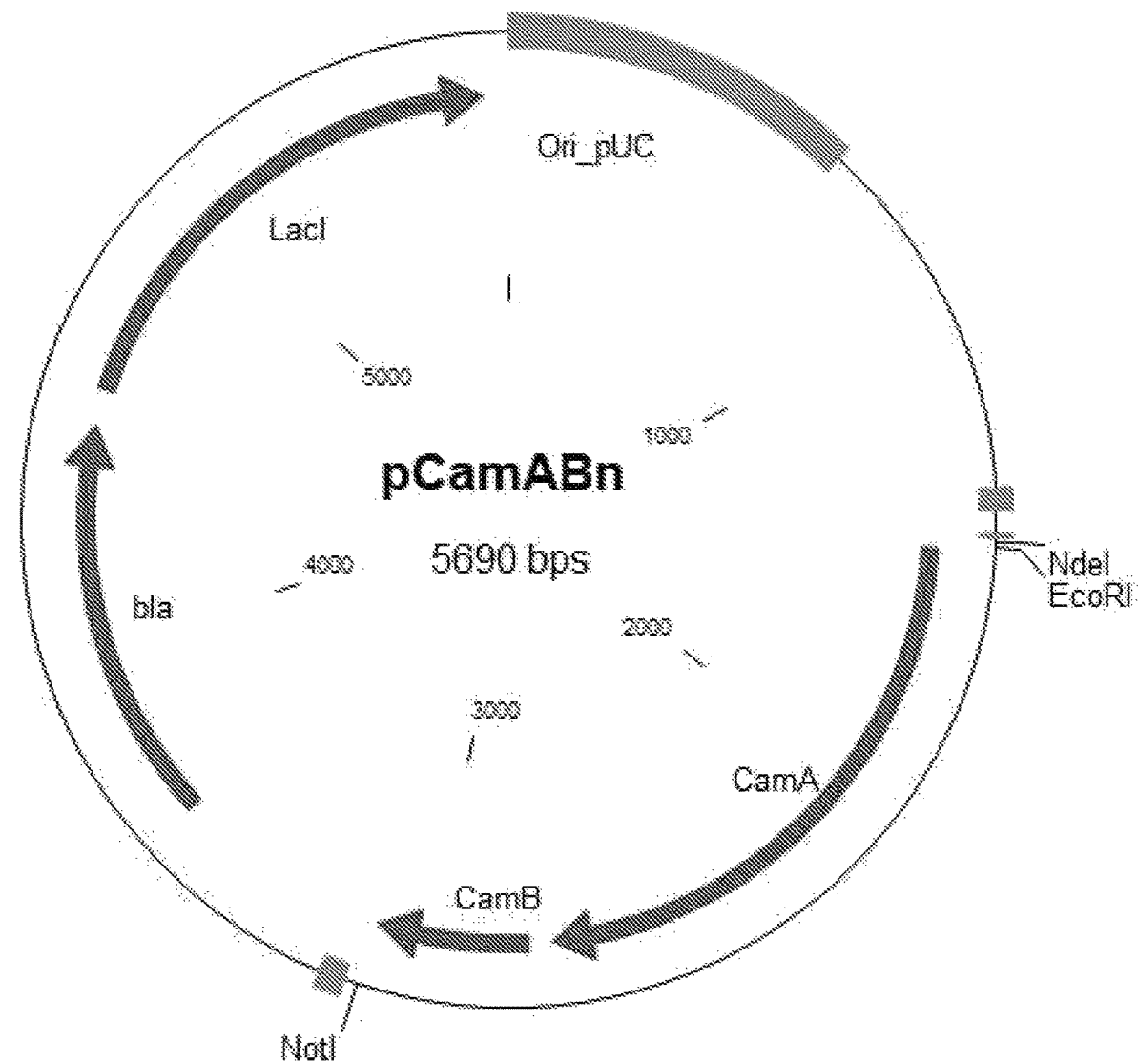
FIG. 16. Shows expression vector pCamABn
Figure 17:
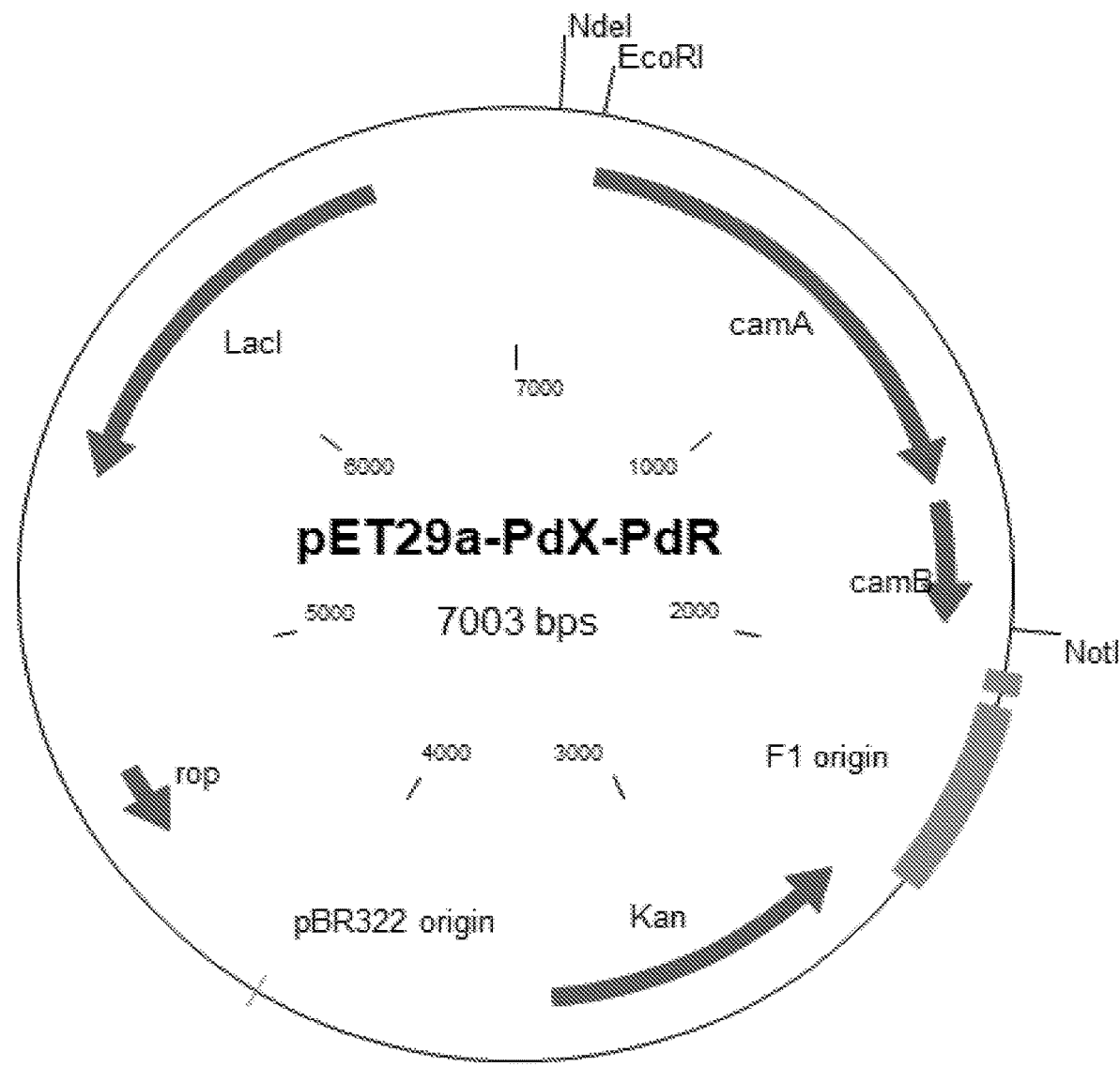
FIG. 17. Shows expression vector pET29a-PdR-PdX
Figure 18:
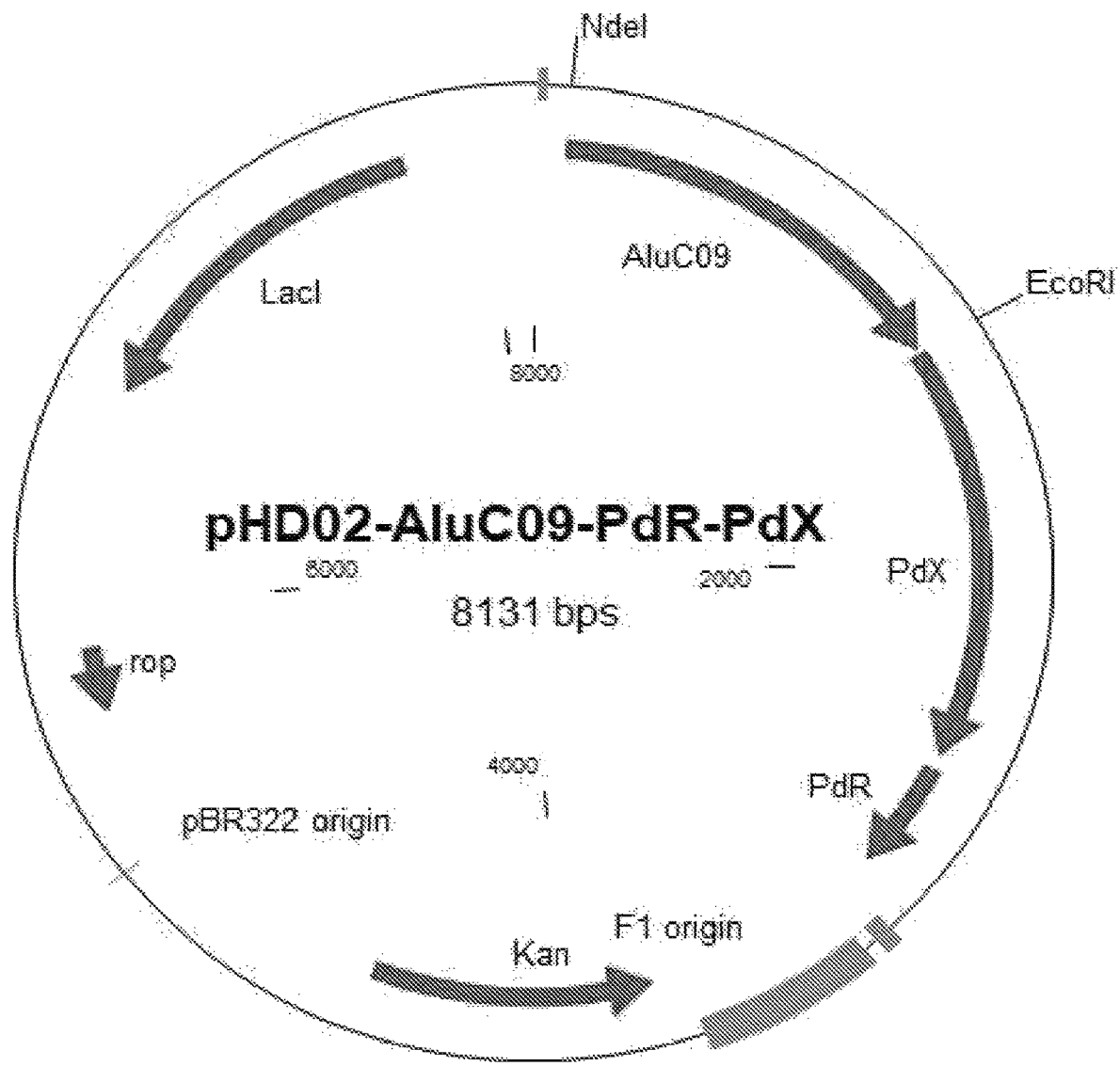
FIG. 18. Shows expression vector pHD02-AluC09-PdR-PdX
Figure 19:
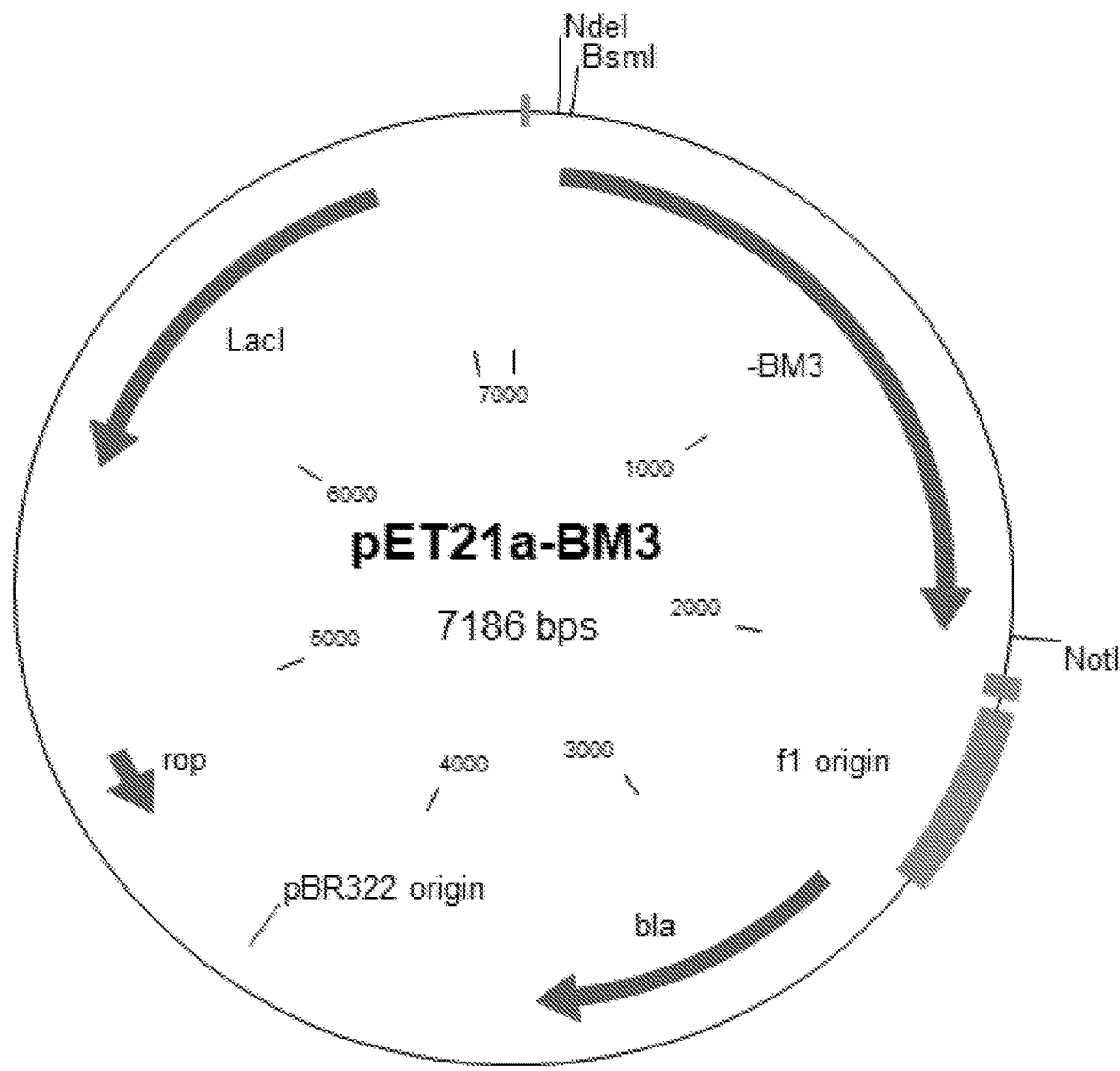
FIG. 19. Shows expression vector pET21a-BM3
Figure 20:
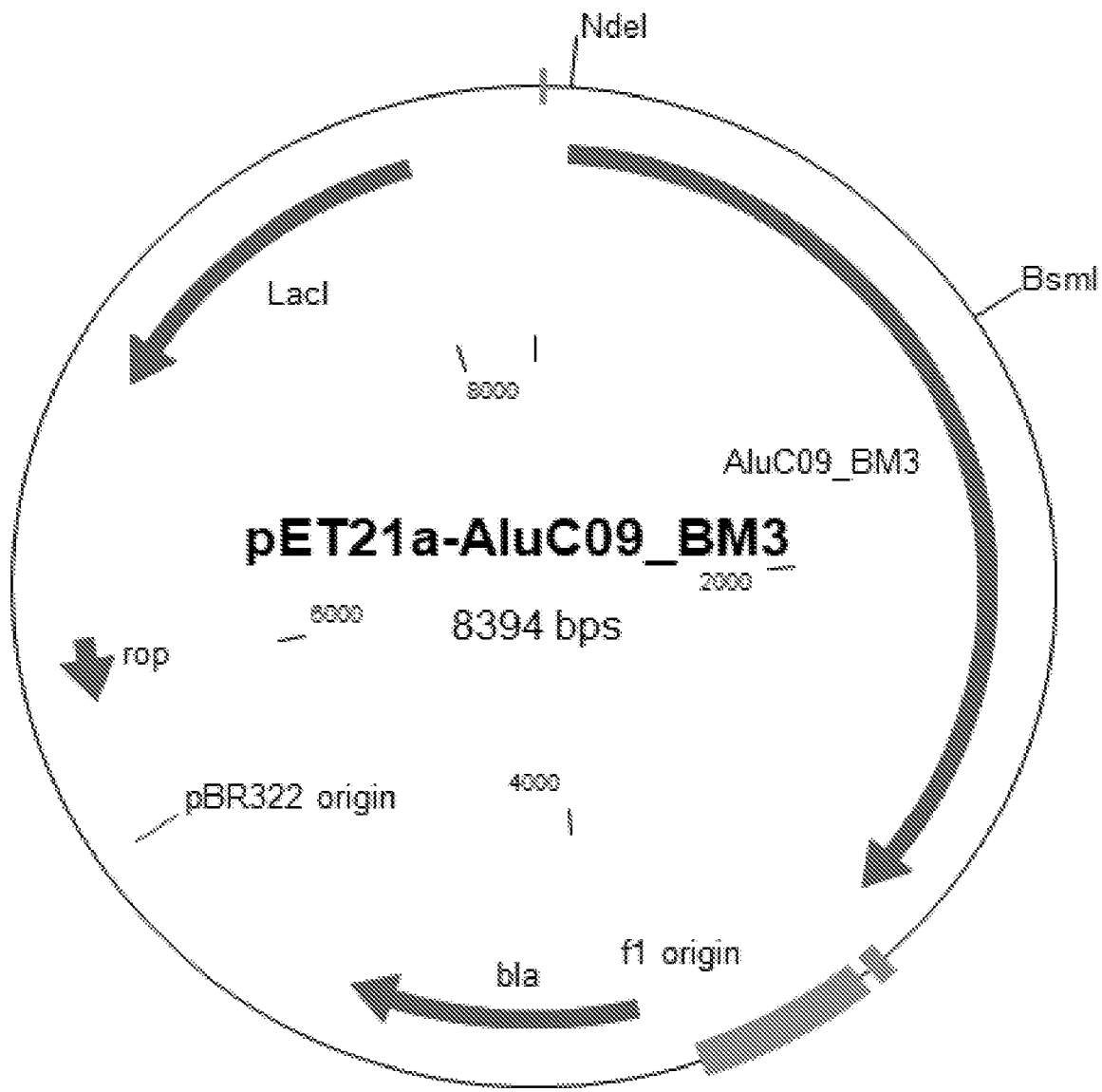
FIG. 20. Shows expression vector pET21a-AluC09_BM3

Using lyophilised material prepared in a similar manner to that described in Example 7, the effect of different reaction pH upon hydroxylase activity was assessed using two substrates: bosentan and diclofenac. The method in Example 7 was followed except for the buffer exchange section. Four different buffers were chosen: a) 50 mM Acetate pH 5, 100 mM NaCl, 5 mM $MgCl_2$; b) 50 mM potassium phosphate pH7.5, 5 mM $MgCl_2$; c) 50 mM Tris pH 8, 100 mM NaCl, 5 mM $MgCl_2$; d) 50 mM Piperidine pH11, 100 mM NaCl, 5 mM $MgCl_2$. For each buffer condition 1.5 ml of resuspended lyophilised crude extract was exchanged using Vivaspin 20K cut off by performing 3 cycles of concentration and then dilution of the material with the new buffer. Exchanging in 50 mM potassium phosphate pH7.5, 5 mM $MgCl_2$, the usual buffer for preparing and assessment of the enzyme preparations, provided the control for the robustness of the material during the buffer exchange process. After 16-20 hours of incubation at the indicated pH, reactions were extracted with an equal volume of acetonitrile, centrifuged to remove precipitated proteins and conversion assessed by UPLC-MS analysis in a similar manner to that described in Example 7. Results are shown in FIGS. 10 & 11. The hydroxylase activity is shown to remain at pH values of 7.5 and above (pH 8-11), and to be only barely detectable at pH5. Of particular note is the activity of this recombinant enzyme at such elevated pH values e.g., pH value of 11. The ability to catalyse reactions at such a pH affords a particular commercial advantage because increased substrate loading may be achieved for selected substrates with improved solubility at a higher pH, such as compounds with a carboxyl moiety. Other advantages of catalysis at higher pH are the ability to directly utilise the product from a prior step resulting in such products, such as chemical synthesis, base-catalysed hydrolysis of a feedstock, or reaction product from another enzyme where increasing pH has been used to stop that reaction Example 9: Influence of Temperature of Incubation on Hydroxylase Activity Using lyophilised material of recombinant $P450_{aluC09}$, $ferredoxin_{aluF03}$ and ferredoxin $reductase_{SCF15A}$ in a similar manner to that described in Example 7, the effect of different temperature of incubation upon hydroxylase activity was assessed using four substrates: bosentan, diclofenac, ritonavir, and tivantanib. The temperatures assessed were as indicated in the Table 1. After 16-20 hours of incubation at the indicated temperature, reactions were extracted with an equal volume of acetonitrile, centrifuged to remove precipitated proteins and conversion assessed by UPLC-MS analysis in a similar manner to that described in Example 7. Results are shown in Table 1_. The hydroxylase activity was generally highest at 10° C. with similar catalytic conversions at 22° C. and 27° C.; however conversion was greatly decreased by increasing the temperature to 37° C. and beyond to 45° C.

TABLE 1

Effect of the temperature on hydroxylase activity of $P450_{aluC09}$-$ferredoxin_{aluF03}$-ferredoxin $reductase_{SCF15A}$ against bosentan, diclofenac, ritonavir, and tivantanib

| | 10° C. | 22° C. | 27° C. (standard condition) | 37° C. | 45° C. |
|---|---|---|---|---|---|
| HO-Bosentan | 91% | 64% | 86% | 33% | 19% |
| 5-HO-Diclofenac | 17% | 14% | 12% | 1% | |
| 4'-HO-Diclofenac | 14% | 16% | 21% | 13% | |
| ε-HO-Ritonavir | 36% | 36% | 34% | 19% | |
| HO-Tivantanib (M4/M5) | 11% | 8% | 6% | | |

Example 10: Hydroxylase Activity with Different Plasmid Copy Number

Whole-cell hydroxylating activity of the recombinant strains expressing $P450_{aluF03}$, $ferredoxin_{aluF03}$ and ferredoxin $reductase_{SCF15A}$ in high (pUC origin of replication) and medium (pBR322 origin of replication) copy plasmids were compared against the substrates bosentan and diclofenac.

Construction of High Copy Version of pQR368bb-aluC09-aluF03

The $P450_{aluC09}$, $ferredoxin_{aluF03}$ and ferredoxin $reductase_{SCF15A}$ operon was digested from the pQR368bb-aluC09-aluF03 plasmid and subcloned into the vector backbone containing a high copy pUC origin of replication by T4 DNA ligase.

The $P450_{aluC09}$, $ferredoxin_{aluF03}$ and ferredoxin $reductase_{SCF15A}$ operon was obtained by digesting the pQR368bb-aluC09-aluF03 plasmid by NdeI and NotI and the band with the expected size of 2801 bp was purified from the agarose gel by QIAquick® Gel Purification Kit (Qiagen).

The pD454-SR:242370 is a high copy vector containing $ferredoxin_{fd1}$ and ferredoxin $reductase_{SCF15A}$ in a single polycistronic operon (SEQ ID NO: 9) and was constructed by DNA2.0. The pD454-SR:242370 plasmid was digested by NdeI and NotI and the band with the expected size of 4021 bp was purified as above. The digested fragment (140 mg) was ligated with the vector backbone (40 mg) by T4 DNA ligase (New England Biolabs) in a total reaction volume of 20 μL. The reaction was incubated at room temperature for 1.5 hours and further incubated at 65° C. for 20 minutes to inactivate the ligase enzyme. The ligation reaction mixture (0.5 μL) was directly introduced into 50 μL of chemically competent E. coli DH5α by chemical transformation. The sequencing and construction of recombinant strain were performed in a similar manner as described in Example 4. The constructed plasmid was designated as p3C.1-AluC09-AluF03.

Influence of Plasmid Copy Number on Whole Cell Hydroxylation Activity

The recombinant expression strains E. coli BL21 Star (DE3) pLysS with pQR368bb-aluC09-aluF03 and E. coli BL21 Star (DE3) pLysS with p3C.1-AluC09-AluF03 were cultured in Terrific Broth media as in Example 5 and gene expression was induced by adding IPTG to reach the final concentration of 1 mM. The culture was supplemented with $FeSO_4$ and 5'-aminolevulinic acid as in Example 5.

After four hours of incubation at 27° C. and 200 rpm, 2.5 mL of induced culture was dosed with 10 μL of either bosentan or diclofenac (25 mg/mL each) in a 24-well block (Enzyscreen). The whole-cell biocatalysis reaction was allowed to further incubate for 24 hours at 30° C. and 300 rpm. The reaction was stopped with an equal amount of acetonitrile and conversion assessed by UPLC-MS analysis in a similar manner to that described in Example 7.

Both recombinant strains with different number of plasmid copies were able to hydroxylate bosentan and diclofenac in whole-cell biotransformations and the percentage conversions of the parent metabolite are shown in Table 2. The medium copy expression strain (pQR368bb-aluC09-aluF03) exhibited an improved whole-cell hydroxylase activity against bosentan and diclofenac when compared to the high copy expression strain (p3C.1-aluC09-aluF03). This result indicates expression can be modified by using different plasmid copy numbers with the counterintuitive preference being the use lower rather than higher copy number plasmids.

TABLE 2

Effect of different plasmid copy number on whole cell biocatalysis.

| | % yield of-parent derived products | |
|---|---|---|
| Metabolite | Medium copy number strain (pQR368bb-aluC09-aluF03) | High copy number strain (p3C.1-AluC09-AluF03) |
| HO-bosentan 568 m/z | 52.6 | 18.2 |
| 5-HO-diclofenac 310 m/z | 60.3 | 23.8 |
| 4'-HO-diclofenac 310 m/z | 27.4 | 8.7 |

Example 11: Hydroxylase Activity with Different Antibiotic Resistance Markers Whole-cell hydroxylating activity of recombinant strains expressing P450$_{aluF03}$, ferredoxin$_{aluF03}$ and ferredoxin reductase$_{SCF15A}$ in ampicillin and kanamycin resistant plasmids were compared against the substrates bosentan and diclofenac.

Construction of Kanamycin Resistant Derivative of pQR368bb-aluC09-aluF03

The P450$_{aluC09}$, ferredoxin$_{aluF03}$ and ferredoxin reductase$_{SCF15A}$ operon was digested from the pQR368bb-aluC09-aluF03 plasmid and cloned into the pET29a vector backbone via NdeI and NotI by T4 DNA ligase in a similar manner performed in Example 10. The constructed plasmid was designated as pHD02-AluC09-AluF03.

Influence of Antibiotic Selection Marker on Whole Cell Hydroxylation Activity

Whole-cell hydroxylation activity of the recombinant expression strains E. coli BL21 Star (DE3) pLysS with pQR368bb-aluC09-aluF03 and E. coli BL21 Star (DE3) pLysS with pHD02-AluC09-AluF03 were performed in a similar manner as described in Example 10.

Both the ampicillin and kanamycin resistant recombinant expression strains were able to hydroxylate bosentan and diclofenac in whole-cell biotransformations and the percentage conversions of the parent metabolite are shown in Table 3. Kanamycin resistant expression strain (pHD02-AluC09-AluF03) exhibited an improved whole-cell hydroxylase activity against bosentan and diclofenac when compared to the ampicillin resistant expression strain (pQR368bb-aluC09-aluF03). The data show expression levels can be improved by use of different antibiotic resistance genes; using a more stable antibiotic provides greater selection pressure during the entire cultivation period.

TABLE 3

Effect of different antibiotic resistance markers on whole cell biocatalysis.

| | % yield of parent-derived products | |
|---|---|---|
| Metabolite | Ampicillin resistant strain (pQR368bb-aluC09-aluF03) | Kanamycin resistant strain (pHD02-AluC09-AluF03) |
| HO-bosentan 568 m/z | 26.6 | 41.6 |
| 5-HO-diclofenac 310 m/z | 35.2 | 48.1 |
| 4'-HO-diclofenac 310 m/z | 7.5 | 6.0 |

Example 12: Hydroxylase Activity with Different BL21-Derived Expression Hosts Whole-cell hydroxylating activity of recombinant strains expressing P450$_{aluF03}$, ferredoxin$_{aluF03}$ and ferredoxin reductase$_{SCF15A}$ in different BL21-derived expression hosts were compared against the substrates bosentan and diclofenac.

Construction of Recombinant Expression Strains

The pQR368bb-aluC09-aluF03 plasmid was introduced into various BL21-derived expression hosts in a similar manner as described in Example 4.

Influence of Expression Hosts on Whole Cell Hydroxylation Activity

Whole cell hydroxylation activity of the different recombinant expression strains E. coli BL21 Star (DE3) pLysS, E. coli BL21 Star (DE3), E. coli BL21 (DE3) and E. coli BL21 (DE3) pLysS all harbouring the pQR368bb-aluC09-aluF03 plasmid were performed in a similar manner described in Example 10.

All recombinant expression strains were able to hydroxylate bosentan and diclofenac in whole-cell biotransformations and the percentage conversions of the parent metabolite are shown in Table 4. E. coli BL21 (DE3) pLysS harbouring pQR368bb-aluC09-aluF03 exhibited greater whole-cell hydroxylase activity against bosentan and diclofenac when compared to the other BL21-derivative expression hosts. Results in Table 4 indicate the P450$_{AluF03}$, ferredoxin$_{AluF03}$ and ferredoxin reductase$_{SCF15A}$ polycistronic operon can be expressed and is catalytically active in other expression hosts e.g., other BL21-derived expression hosts.

TABLE 4

Whole-cell biocatalytic activity observed with different BL21-derived expression hosts.

| | % yield of parent-derived products | | | |
|---|---|---|---|---|
| Metabolite | E. coli BL21 Star (DE3) pLysS | E. coli BL21 Star (DE3) | E. coli BL21 (DE3) | E. coli BL21 (DE3) pLysS |
| HO-bosentan 568 m/z | 26.6 | 9.1 | 13.6 | 34.1 |
| 5-HO-diclofenac 310 m/z | 35.2 | 6.5 | 10.3 | 45.1 |
| 4'-HO-diclofenac 310 m/z | 7.5 | 1.5 | >1 | 11.3 |

Example 13: Hydroxylase Activity with Other Redox Partners

A: Swapping of Native Ferredoxin$_{aluC09}$ with Ferredoxin$_{fd1}$ from Streptomyces griseus 11796

Whole-cell hydroxylating activity of recombinant strains expressing P450$_{aluF03}$, ferredoxin reductase$_{SCF15A}$ and either the native ferredoxin$_{aluF03}$ or another ferredoxin from a closely related organism (Fd1 from S. griseus 11796, Hussain & Ward., Appl Environ Microbiol. 2003; 69(1): 373-82) were compared against the substrates bosentan and diclofenac.

PCR Reactions

The native ferredoxin$_{aluF03}$ was swapped with ferredoxin$_{fd1}$ from S. griseus 11796 by cloning P450$_{aluC09}$ from pQR368bb-aluC09-aluF03 into the pD454-SR:242370 plasmid. The P450$_{aluC09}$ gene was amplified from pQR368bbaluC09-aluF03 plasmid DNA by PCR using the primers aluC09_p3C_F (5'-primer sequence-3': cttttgagaccttaagg-aggtaaaaaATGTCTCATATGACTGACGTCGAGGAAAC-CAC) (SEQ ID NO: 12) and aluC09_p3C_R (5'-primer sequence-3': gatccgcactcacccgcatggtcatgaattctgtttcctataaT-TACCAGGTGACCGGAAGGGCG) (SEQ ID NO: 13) in a similar manner described in Example 4. The expected size amplicon of 1294 by was purified from the agarose gel.

Construction of the p3C-AluC09 Plasmid

The pD454-SR:24370 plasmid was digested with NdeI and EcoRl to give a product with an expected size of 5616 bp. The digested product was purified from the agarose as described in Example 4. The purified DNA was assembled into an NdeI and EcoRl digested pD454-SR:242370 plasmid by Gibson assembly (New England Biolabs). The protocol was followed as in the manufacturer's instructions with the isothermal incubation step performed for 20 minutes. The constructed plasmid was designated as p3C-AluC09.

Influence of Swapping Native Ferredoxin$_{aluF03}$ with Ferredoxin$_{fd1}$ from S. griseus 11796 on Whole Cell Hydroxylation Activity Whole-cell hydroxylating activity of E. coli BL21 Star (DE3) pLysS with p3C.1-AluC09-AluF03 or p3C-AluC09 plasmids were compared against the substrates bosentan and diclofenac in a similar manner described in Example 10.

Both recombinant expression strains were able to hydroxylate bosentan and diclofenac in whole-cell biotransformations and the percentage conversions of the parent metabolite are shown in Table 5. E. coli BL21 (DE3) pLysS harbouring p3C.1-AluC09-AluF03, which contains the native ferredoxin partner, exhibited greater whole-cell hydroxylase activity against bosentan and diclofenac when compared to the strain expressing ferredoxin$_{fd1}$. Results in Table 5 indicate other ferredoxin partners from closely related microorganisms, such as ferredoxin$_{fd1}$ from S. griseus 11796, are still able to support the transfer electrons from reduced cofactors NADH or NADPH to the cytochrome, albeit to a lesser extent in the case of ferredoxin$_{fd1}$.

TABLE 5

Effect of swapping ferredoxin partners on whole cell biocatalytic activity.

| | % yield of parent-derived products | |
|---|---|---|
| Metabolite | Native ferredoxin$_{aluF03}$ (p3C.1-AluC09-AluF03 | Ferredoxin$_{fd1}$ (p3C-AluC09) |
| HO-bosentan 568 m/z | 52.6 | 6.3 |
| 5-HO-diclofenac 310 m/z | 23.8 | 4.2 |
| 4'-HO-diclofenac 310 m/z | 60.3 | 11.5 |

B: Swapping of AluF03-SCF15A Ferredoxin-Ferredoxin Reductase with PdR-PdX from Pseudomonas putida To further validate P450$_{aluC09}$ can receive electrons from other redox partners. The ferredoxin$_{aluF03}$ and ferredoxin reductase$_{SCF15A}$ from pQR368bb-aluC09-aluF03 plasmid were swapped with ferredoxin$_{camB}$ and ferredoxin reductase$_{camA}$ redox partners from Psuedomonas putida ATCC 17453 (Koga et al. J Biochem. 1989; 106(5):831-6).

PCR Reactions

The ferredoxin reductase$_{camB}$ and ferredoxin$_{camA}$ operon were amplified from P. putida ATCC 17453 by PCR using the primers PdR-Pdx_op_F (5'-primer sequence-3': gtaa-aaaatgtctcatATGGGCGGCGAATTCATGAACGCAAA-CGACAACGTG) (SEQ ID NO: 17) and PdR-Pdx_op_R (5'-primer sequence-3': gtgagacctcaaccgcggccgctcaTTAC-CATTGCCTATCGGGAAC) (SEQ ID NO: 18) in a similar manner described in Example 4. The expected size amplicon of 1704 bp was purified from the agarose gel.

Construction of pCamABn Plasmid

The purified DNA was assembled into an EcoRl and NotI digested pD454-SR:242370 plasmid by Gibson assembly in a similar manner described in Example 13. The constructed plasmid was designated as pCamABn.

Construction of pET29a-PdR-PdX

The ferredoxin reductase$_{camA}$ and ferredoxin$_{camB}$ operon was subcloned from pCamABn into pET29a plasmid in a similar manner described in Example 10. The pCamABn and pET29a plasmids were digested with EcoRI and NotI; the 1658 bp and 5345 bp fragment respectively were purified from the agarose gel. The ferredoxin reductase$_{camA}$ and ferredoxin$_{camB}$ operon was subcloned into pET29a vector backbone by T4 DNA ligase. The constructed plasmid was designated as pET29a-PdR-PdX.

Construction of pHD02-AluC09-PdR-PdX

The P450$_{aluC09}$ gene was cloned into the pET29a-PdR-PdX plasmid to produce a single polycistronic operon containing P450$_{aluC09}$, ferredoxin reductase$_{camA}$ and ferredoxin$_{camB}$.

P450$_{aluC09}$ gene was amplified from pQR368bb-aluC09-aluF03 plasmid DNA by PCR using the primers AluC09_f (5'-primer sequence-3': attttgtttaactttaagaaggagatatacat-ATGACTGACGTCGAGGAAAC) (SEQ ID NO: 19) and AluC09_r (5'-primer sequence-3': gacgatgaccacgttgtcgttt-gcgttcatgaattctgtttcctataaTTACCAGGTGACCGGAAG) (SEQ ID NO: 20) in a similar manner described in Example 4. The expected size amplicon of 1295 bp was purified from the agarose gel. The purified DNA was assembled into an NdeI and EcoRl digested pET29a-PdR-PdX plasmid by Gibson assembly in a similar manner described in Example 13A. The constructed plasmid was designated as pHD02-AluC09-PdR-PdX.

Influence of Swapping Ferredoxin$_{aluF03}$ and Ferredoxin Reductase$_{SCF15A}$ with Ferredoxin Reductase$_{camA}$ and Ferredoxin$_{camB}$ from P. putida ATCC 17453 on Whole Cell Hydroxylation Activity Whole-cell hydroxylating activity of E. coli BL21 (DE3) with pHD02-AluC09-AluF03 or pHD02-AluC09-PdR-PdX plasmid were compared against the substrates bosentan and diclofenac in a similar manner described in Example 10.

Both recombinant expression strains were able to hydroxylate bosentan and diclofenac in whole-cell biotransformations and the percentage conversions of the parent metabolite are shown in Table 6. E. coli BL21 (DE3) harbouring pHD02-AluC09-AluF03, which contains the native ferredoxin partners, still exhibited greater, albeit similar whole-cell hydroxylase activity against bosentan and diclofenac when compared to the strain expressing ferredoxin reductase$_{camA}$ and ferredoxin$_{camB}$. Results in Table 6, in conjuncation with those in Table 5, indicate that the biocatalytic activity of P450$_{aluC09}$ can be altered via pairing with other, non-native ferrodoxin partners and therefore expected to be improved upon by screening a wider number of non-native ferrodoxin partners.

TABLE 6

Effect of swapping ferredoxin and ferredoxin reductase partners on whole cell biocatalytic activity.

| | % yield of parent-derived products | |
|---|---|---|
| Metabolite | ferredoxin$_{aluF03}$ and ferredoxin reductase$_{SCF15A}$ (pHD02-AluC09-AluF03) | Ferredoxin reductase$_{camA}$ and ferredoxin$_{camB}$ (pHD02-AluC09-PdR-PdX) |
| HO-bosentan 568 m/z | 27.4 | 21.2 |

C: P450$_{aluC09}$-BM3 Fusion Protein

The P450$_{aluC09}$ was engineered to fuse in-frame to the reductase domain of P450$_{BM3}$ from *Bacillus megaterium* in a similar manner described in Scheps et al. Microb Biotechnol. 2013; 6(6):694-707.

PCR Reactions

The P450$_{aluC09}$ without the stop codon was amplified from pQR368bb-aluC09-aluF03 by PCR using the primers AluC09_BM3_For (5'-primer sequence-3': tctcatATGA-CTGACGTCGAGGAAACCACC) (SEQ ID NO: 21) and AluC09_LBM3_Rev (5'-primer sequence-3': CTGTT-CAGTGCTAGGTGAAGGAATGCTGCCGCCGCTGCC-GCCGCTGCCGC CCCAGGTGACCGGAAGGGCGTG-GAGGCCG) (SEQ ID NO: 22) in a similar manner described in Example 4. The expected size amplicon of 1269 bp was obtained and purified from the agarose gel.

Construction of pET21a-AluC09_BM3 plasmid

The pET21_BM3 plasmid contains the reductase domain of the P450$_{BM3}$ (SEQ ID NO: 23) and was constructed by Genscript. The pET21a_BM3 plasmid was digested by NdeI and BsmI and the band with the expected size of 7155 bp was purified from the agarose gel in a similar manner described in Example 4.

The purified PCR DNA was also digested with NdeI and BsmI and ligated with the purified digested pET21a_BM3 fragment by T4 DNA ligase in a similar manner described in Example 10. The constructed plasmid was designated as pET21a-AluC09_BM3.

Influence of Fusing P450$_{aluC09}$ with the Reductase Domain of P450$_{BM3}$ on Whole Cell Hydroxylation Activity Whole-cell hydroxylating activity of *E. coli* BL21 Star (DE3) pLysS with either pQR368bb-aluC09-aluF03 or pET21a-AluC09_BM3 plasmid were compared against the substrates bosentan and diclofenac in a similar manner described in Example 10.

Both recombinant expression strains were able to hydroxylate bosentan and diclofenac in whole-cell biotransformations and the percentage conversions of the parent metabolite are shown in Table 7. *E. coli* BL21 Star (DE3) pLysS harbouring pQR368bb-aluC09-aluF03, which contains the native ferredoxin partners, exhibited greater whole-cell hydroxylase activity against bosentan and diclofenac when compared to the strain expressing P450$_{aluC09}$ fused in-frame with the reductase domains of P450$_{BM3}$, however the presence of activity confirmed ability of P450$_{aluC09}$ to be catalytically active when incorporated into a fusion protein product. It is expected the activity of a fusion product would be improved by varying the linker length and linker composition in a similar manner to that described in Scheps et al. Microb Biotechnol. 2013; 6(6):694-707.

TABLE 7

Effect of fusing P450$_{aluC09}$ with the reductase domain of P450$_{BM3}$ on whole cell biocatalytic activity.

| | % yield of parent-derived products | |
|---|---|---|
| Metabolite | ferredoxin$_{aluF03}$ and ferredoxin reductase$_{SCF15A}$ (pQR368bb-aluC09-aluF03) | P450$_{aluC09}$ fused with reductase domains of P450$_{BM3}$ (pET21a-AluC09__BM3) |
| HO-bosentan 568 m/z | 29.5 | 9.3 |
| 5-HO-diclofenac 310 m/z | 12.4 | <1 |
| 4-HO-diclofenac 310 m/z | 46.0 | 4.7 |

---

The invention claimed is:

1. A method for the production of a hydroxylated organic compound, comprising reacting an organic compound with a cytochrome P-450 enzyme comprising SEQ ID NO: 3, or a variant enzyme having at least 98.4% identity thereto and having CYP-450 activity, wherein the cytochrome P 450 enzyme is used to catalyze the hydroxylation of a propyl group or a butyl group.

2. The method according to claim 1, wherein the cytochrome P-450 enzyme is used to catalyze the hydroxylation of an isopropyl or isobutyl group.

3. The method according to claim 1, wherein the cytochrome P-450 enzyme is used to catalyse the hydroxylation of a tent-butyl group.

4. The method according to claim 1, wherein the cytochrome P-450 enzyme is used to catalyze the hydroxylation of a compound of formula (II), where R represents the rest of the compound and where $R^1$ is $CH_3$ or H:

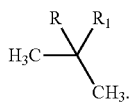

(II)

5. The method according to claim 1, wherein the compound to be hydroxylated is bosentan, buparvaquone, BIRB796 or ritonavir.

6. The method according to claim 1, wherein the cytochrome P-450 enzyme is used in combination with reductase components.

7. The method according to claim 6, wherein the reductase components are ferredoxin and ferredoxin reductase components.

8. The method according to claim 1, wherein the cytochrome P-450 enzyme comprises a sequence having at least 99% identity to SEQ ID NO: 3.

9. The method according to claim 1, wherein the P-450 enzyme is in purified form, part-purified form, crude enzyme extract, in a recombinant host cell or a natural host cell.

10. The method according to claim 1, wherein the cytochrome P-450 enzyme is present in *Amycolatopsis lurida* (NRRL-2430) cells, and wherein the cells are dosed with the organic compound to be hydroxylated.

11. The method according to claim 1, wherein the cytochrome P-450 enzyme is expressed by at least one recombinant microorganism comprising a heterologous nucleic acid encoding the enzyme, and wherein the at least one recombinant microorganism is dosed with the organic compound to be hydroxylated.

12. The method according to claim 1, wherein said reacting results in hydroxylation of the organic compound, which takes place at a pH in the range of 8-11.

13. The method according to claim 10, wherein the cells are subsequently harvested and purified to obtain the hydroxylated compound.

14. The method according to claim 11, wherein a purification step is carried out, after dosing the recombinant microorganism, to obtain the hydroxylated compound.

15. The method according to claim 1, wherein the cytochrome P-450 enzyme comprises SEQ ID NO: 3.

* * * * *

SEQUENCE LISTING

<160> NUMBER OF SEQ ID NOS: 26

<210> SEQ ID NO 1
<211> LENGTH: 1418
<212> TYPE: DNA
<213> ORGANISM: Amycolatopsis lurida

<400> SEQUENCE: 1

```
ttaagcgagc gacaaggcct gccccgggca gatgtgcacg gcggtgcggg cgtttcttc      60 cgcctcttcg ccttcaggct cggcgttcag cacgaggacc gttccgtcgt cctcgctctg    120
atcgaacaga tcgggatcgg tgagcacgca ctggcccgcg cccacgcatt tcccggtgtc    180
cgcgatgatc ttcatggctc ctcctaccag gtgaccggaa gggcgtggag gccgtagatc    240
gtcgaatcgt gcttgaacgg cagttcgtcg accggaacgg cgatccggag gcccggcact    300
cgccggaaca acgtatcgaa gacgatctgg agttccaacc tcgccaagtt ctggccgaga    360
cactggtgca ccccgaatcc gaacgcgacg tgatgccgcg cgccgcgttc gatgtcgaag    420
gtgtccgggt tctcgaagcc gtccggatcg tggttgcccg cgttgctcag gcccaccacc    480
ccttcccccg cgcggatcag cgttccgccg atctcgacgt ccgccgtggc gaagcgtgag    540
```

```
gtcgccgttt ccgcgatcgt gaagacccgc aggagttcct cgatggcggc gagggtcttg    600
ccggggtctg ccttgatctt cgcgagctga tcgggattct ccagcaggg t caccgtgccg   660 agcgagatca tgttcgccgt ggtctcgtgt ccggcgatga gcagcaggaa cgccagcccg    720
acgagttcac cgtggtcggc ctcgcccgtt tcccgctgtt tcaggatctg acggccgagg    780
aggtcgtcct cggtggcgtt cgcctccttc ttggtgacca gttcgtcgag atagttttcg    840
agctgctcga acgcggtcat ccgttcttcg gcggtgaccc ccggctgag catcctggaa     900 ctgcaggact ggaagaactc gtggtccgaa taggggacgc cgagcagttc gcagatcacc    960
agcgagggaa cgggcaggga aagcgcctgg acgagatcgg cgggtttggg gcccgcgagc    1020
agggcgtcga gatgttcgtc gacgatctgc tgaattcgcg gctggagcgc cttcatccgc    1080
ttgacggtga attccccgac gacgtcacgc ctggcccggc tgtgttccgg cggatccatc    1140
gcgatgaggg aggggcggaa cggcttgtcc tcgcggcgga tctgccgcgc gaccatcagc    1200
gggaacgacg ggctctgccg gtcggaactg aaatgcgggc tgctcagcat ttcgcggatg    1260
tcttcgagcc gggtgagcgc ccaagccgtt tgaccggacg ggagaccgac ccgggaaacc    1320
ggactttccc ggcgaagccg ttcgtattcg gcggcggcg aaaacgggca tttccgggcc     1380
agcggcaagg tcgcggtggt ttcctcgacg tcagtcat                            1418

<210> SEQ ID NO 2
<211> LENGTH: 1418
<212> TYPE: DNA
<213> ORGANISM: Amycolatopsis lurida

<400> SEQUENCE: 2
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg    120
tccggtcaaa cggcttgggc gctcacccgg ctcgaagaca tccgcgaaat gctgagcagc    180
ccgcatttca gttccgaccg gcagagcccg tcgttcccgc tgatggtcgc gcggcagatc    240
cgccgcgagg acaagccgtt ccgcccctcc ctcatcgcga tggatccgcc ggaacacagc    300
cgggccaggc gtgacgtcgt cggggaattc accgtcaagc ggatgaaggc gctccagccg    360
cgaattcagc agatcgtcga cgaacatctc gacgccctgc tcgcgggccc caaacccgcc    420
gatctcgtcc aggcgctttc cctgcccgtt ccctcgctgg tgatctgcga actgctcggc    480 gtccccta tt cggaccacga gttcttccag tcctgcagtt ccaggatgct cagccgggag    540
gtcaccgccg aagaacggat gaccgcgttc gagcagctcg aaaactatct cgacgaactg    600
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcgaa a acggcgacct cacgcttcgc cacggcggac    900
gtcgagatcg gcggaacgct gatccgcgcg ggggaagggg tggtgggcct gagcaacgcg    960
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgccctt    1200
ccggtcacct ggtaggagga gccatgaaga tcatcgcgga caccgggaaa tgcgtgggcg    1260
```

```
cgggccagtg cgtgctcacc gatcccgatc tgttcgatca gagcgaggac gacggaacgg   1320
tcctcgtgct gaacgccgag cctgaaggcg aagaggcgga agaaaacgcc cgcaccgccg   1380
tgcacatctg cccggggcag gccttgtcgc tcgcttaa                           1418
```

<210> SEQ ID NO 3
<211> LENGTH: 404
<212> TYPE: PRT
<213> ORGANISM: Amycolatopsis lurida

<400> SEQUENCE: 3

```
Met Thr Asp Val Glu Glu Thr Thr Ala Thr Leu Pro Leu Ala Arg Lys
 1               5                   10                  15

Cys Pro Phe Ser Pro Pro Glu Tyr Glu Arg Leu Arg Arg Glu Ser
                20                  25                  30

Pro Val Ser Arg Val Gly Leu Pro Ser Gly Gln Thr Ala Trp Ala Leu
            35                  40                  45

Thr Arg Leu Glu Asp Ile Arg Glu Met Leu Ser Ser Pro His Phe Ser
50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Thr Ala Thr Ser Arg Phe Ala Thr Ala Asp Val Glu Ile Gly
290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
```

-continued

```
                340                 345                 350
Cys Leu Gly Gln Asn Leu Ala Arg Leu Glu Leu Gln Ile Val Phe Asp
            355                 360                 365

Thr Leu Phe Arg Arg Val Pro Gly Leu Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp

<210> SEQ ID NO 4
<211> LENGTH: 64
<212> TYPE: PRT
<213> ORGANISM: Amycolatopsis lurida

<400> SEQUENCE: 4

Met Lys Ile Ile Ala Asp Thr Gly Lys Cys Val Gly Ala Gly Gln Cys
1               5                   10                  15

Val Leu Thr Asp Pro Asp Leu Phe Asp Gln Ser Glu Asp Asp Gly Thr
            20                  25                  30

Val Leu Val Leu Asn Ala Glu Pro Glu Gly Glu Ala Glu Glu Asn
        35                  40                  45

Ala Arg Thr Ala Val His Ile Cys Pro Gly Gln Ala Leu Ser Leu Ala
    50                  55                  60

<210> SEQ ID NO 5
<211> LENGTH: 50
<212> TYPE: DNA
<213> ORGANISM: Artificial Sequence
<220> FEATURE:
<223> OTHER INFORMATION: forward primer

<400> SEQUENCE: 5
gtttaacttt aagaaggaga tatacatatg actgacgtcg aggaaaccac              50

<210> SEQ ID NO 6
<211> LENGTH: 40
<212> TYPE: DNA
<213> ORGANISM: Artificial Sequence
<220> FEATURE:
<223> OTHER INFORMATION: reverse primer

<400> SEQUENCE: 6
gagggcgggg cataagcttc ctattaagcg agcgacaagg                         40

<210> SEQ ID NO 7
<211> LENGTH: 32
<212> TYPE: DNA
<213> ORGANISM: Artificial Sequence
<220> FEATURE:
<223> OTHER INFORMATION: forward primer

<400> SEQUENCE: 7
taataggaag cttatgcccc gccctctgcg gg                                 32

<210> SEQ ID NO 8
<211> LENGTH: 35
<212> TYPE: DNA
<213> ORGANISM: Artificial Sequence
<220> FEATURE:
<223> OTHER INFORMATION: reverse primer

<400> SEQUENCE: 8
```

```
gccgcccata tgtatatctc cttcttaaag ttaaa                              35
```

<210> SEQ ID NO 9
<211> LENGTH: 1620
<212> TYPE: DNA
<213> ORGANISM: Artificial Sequence
<220> FEATURE:
<223> OTHER INFORMATION: Coding sequence subcloned into plasmid

<400> SEQUENCE: 9

```
atgtctcata tgggcggcga attcatgacc atgcgggtga gtgcggatcg gacggtctgc      60
gtcggtgccg ggctgtgtgc gctgacggcg ccgggcgtct tcgaccagga cgacgacggg     120
atcgtcacgg tgctgacggc cgaacccgcc gccgacgacg accggcgcac cgcgcgcgag     180
gccggccatc tctgtccgtc cggtgcggtc cgcgtcgtcg aggacacgga ataataggaa     240
gcttatgccc cgccctctgc gggtagccat cgtcggatcc ggcccggccg ggatctacgc     300
cgccgacgcc ctgctcaagt ccgaagtggc cgccgacccc ggtgtttcca tcgacatctt     360
cgagcgcatg cccgccccgt tcggcctcat ccggtacggc gtcgcgcccg accacccgcg     420
gatcaagggc atcatcacgg ccctccacca ggtgctcgac aagccgcaga tccgcctctt     480
cggcaacgtg aactacccca ccgacgtcag cctggacgat ctgcgcgcct tctacgacgg     540
tgtgatcttc gccaccggcg ccacggcgga ccgggacctg tccctcccgg gcatcgacct     600
cgacggctcg tacggcgcgg ccgacttcgt cgcctggtac gacggccacc ccgacttccc     660
gcgcacctgg ccgctggagg cggagaaagt cgccgtcctc ggtgtcggca cgtcgccct      720
ggacatcgcg cgcgtcctcg ccaagacggc cgacagctg ctgccgaccg agatcccgcc      780
gaacgtctac gagggcctca aggccaacaa ggcgctggag gtgcacgtct cggccgccg      840
cggcccggcg caggcgaagt tcagcccgat ggagctgcgg gagctggacc actcccccaa     900
catcgaggtg atcgtcgacc ccgaggacat cgactacgac gagggctcga tcgcgacccg     960
gcgcggcaac aagcaggccg acatggtcgc caagaccctg gagaactggg cgatccgcga    1020
cgtcggcgac cggccgcaca agctgttcct gcacttcttc gagtcgcccg cggagatcct    1080
cggcgaggac ggcagggtga ccggcctgcg caccgagcgc acggagctgg acggcacggg    1140
caacgtcaag ggcaccggcg agttcaagga ctgggacgtc caggcggtct accgggccgt    1200
cggctacctc tccgaccagc tgcccaagct gccctgggac ctcgagacgg cacggtccc     1260
ggacgcgggc ggccgggtcg tccaggagtc cggcgagcac ctccagtcga cgtacgtcac    1320
cggctggatc cggcgcggtc cgatcggcct gatcggccac accaagggcg acgccaacga    1380
gacggtgtcc aacctgctgg acgactacgc gaacggccgt ctccagacgc cctcctcccc    1440
cgctcccgag gccgtggacg cgttcctcgc cgagcggaac gtccgcttca ccacctggga    1500
cggctggtac cggctcgacg ccgcggagaa ggcgcagggc gaaccgcacg gcgtgagcg     1560
cgtgaagtac gtcgagcgcg aggacatgct ccgcgagagc ggcgcctaat gagcggccgc    1620
```

<210> SEQ ID NO 10
<211> LENGTH: 69
<212> TYPE: PRT
<213> ORGANISM: Streptomyces griseus

<400> SEQUENCE: 10

```
Met Thr Met Arg Val Ser Ala Asp Arg Thr Val Cys Val Gly Ala Gly
1               5                   10                  15

Leu Cys Ala Leu Thr Ala Pro Gly Val Phe Asp Gln Asp Asp Asp Gly
            20                  25                  30
```

```
Ile Val Thr Val Leu Thr Ala Glu Pro Ala Ala Asp Asp Arg Arg
            35                  40                  45

Thr Ala Arg Glu Ala Gly His Leu Cys Pro Ser Gly Ala Val Arg Val
 50                  55                  60

Val Glu Asp Thr Glu
65

<210> SEQ ID NO 11
<211> LENGTH: 454
<212> TYPE: PRT
<213> ORGANISM: Streptomyces griseus

<400> SEQUENCE: 11

Met Pro Arg Pro Leu Arg Val Ala Ile Val Gly Ser Gly Pro Ala Gly
 1               5                  10                  15

Ile Tyr Ala Ala Asp Ala Leu Leu Lys Ser Glu Val Ala Ala Asp Pro
            20                  25                  30

Gly Val Ser Ile Asp Ile Phe Glu Arg Met Pro Ala Pro Phe Gly Leu
        35                  40                  45

Ile Arg Tyr Gly Val Ala Pro Asp His Pro Arg Ile Lys Gly Ile Ile
     50                  55                  60

Thr Ala Leu His Gln Val Leu Asp Lys Pro Gln Ile Arg Leu Phe Gly
65                   70                  75                  80

Asn Val Asn Tyr Pro Thr Asp Val Ser Leu Asp Asp Leu Arg Ala Phe
                85                  90                  95

Tyr Asp Gly Val Ile Phe Ala Thr Gly Ala Thr Ala Arg Asp Leu
            100                 105                 110

Ser Leu Pro Gly Ile Asp Leu Asp Gly Ser Tyr Gly Ala Ala Asp Phe
        115                 120                 125

Val Ala Trp Tyr Asp Gly His Pro Asp Phe Pro Arg Thr Trp Pro Leu
130                 135                 140

Glu Ala Glu Lys Val Ala Val Leu Gly Val Gly Asn Val Ala Leu Asp
145                 150                 155                 160

Ile Ala Arg Val Leu Ala Lys Thr Ala Asp Glu Leu Leu Pro Thr Glu
                165                 170                 175

Ile Pro Pro Asn Val Tyr Glu Gly Leu Lys Ala Asn Lys Ala Leu Glu
            180                 185                 190

Val His Val Phe Gly Arg Arg Gly Pro Ala Gln Ala Lys Phe Ser Pro
        195                 200                 205

Met Glu Leu Arg Glu Leu Asp His Ser Pro Asn Ile Glu Val Ile Val
    210                 215                 220

Asp Pro Glu Asp Ile Asp Tyr Asp Glu Gly Ser Ile Ala Thr Arg Arg
225                 230                 235                 240

Gly Asn Lys Gln Ala Asp Met Val Ala Lys Thr Leu Glu Asn Trp Ala
                245                 250                 255

Ile Arg Asp Val Gly Asp Arg Pro His Lys Leu Phe Leu His Phe Phe
            260                 265                 270

Glu Ser Pro Ala Glu Ile Leu Gly Glu Asp Gly Arg Val Thr Gly Leu
        275                 280                 285

Arg Thr Glu Arg Thr Glu Leu Asp Gly Thr Gly Asn Val Lys Gly Thr
    290                 295                 300

Gly Glu Phe Lys Asp Trp Asp Val Gln Ala Val Tyr Arg Ala Val Gly
305                 310                 315                 320

Tyr Leu Ser Asp Gln Leu Pro Lys Leu Pro Trp Asp Leu Glu Thr Gly
```

```
                    325                 330                 335
Thr Val Pro Asp Ala Gly Gly Arg Val Val Gln Glu Ser Gly Glu His
            340                 345                 350

Leu Gln Ser Thr Tyr Val Thr Gly Trp Ile Arg Arg Gly Pro Ile Gly
        355                 360                 365

Leu Ile Gly His Thr Lys Gly Asp Ala Asn Glu Thr Val Ser Asn Leu
    370                 375                 380

Leu Asp Asp Tyr Ala Asn Gly Arg Leu Gln Thr Pro Ser Ser Pro Ala
385                 390                 395                 400

Pro Glu Ala Val Asp Ala Phe Leu Ala Glu Arg Asn Val Arg Phe Thr
                405                 410                 415

Thr Trp Asp Gly Trp Tyr Arg Leu Asp Ala Ala Glu Lys Ala Gln Gly
            420                 425                 430

Glu Pro His Gly Arg Glu Arg Val Lys Tyr Val Glu Arg Glu Asp Met
        435                 440                 445

Leu Arg Glu Ser Gly Ala
    450

<210> SEQ ID NO 12
<211> LENGTH: 59
<212> TYPE: DNA
<213> ORGANISM: Artificial Sequence
<220> FEATURE:
<223> OTHER INFORMATION: forward primer

<400> SEQUENCE: 12 cttttgaga ccttaaggag gtaaaaaatg tctcatatga ctgacgtcga ggaaaccac      59

<210> SEQ ID NO 13
<211> LENGTH: 65
<212> TYPE: DNA
<213> ORGANISM: Artificial Sequence
<220> FEATURE:
<223> OTHER INFORMATION: reverse primer

<400> SEQUENCE: 13
gatccgcact cacccgcatg gtcatgaatt ctgtttccta taattaccag gtgaccggaa    60
gggcg                                                                65

<210> SEQ ID NO 14
<211> LENGTH: 1648
<212> TYPE: DNA
<213> ORGANISM: Pseudomonas putida

<400> SEQUENCE: 14
atgaacgcaa acgacaacgt ggtcatcgtc ggtaccggac tggctggcgt tgaggtcgcc    60
ttcggcctgc gcgccagcgg ctgggaaggc aatatccggt tggtggggga tgcgacggta   120
attccccatc acctaccacc gctatccaaa gcttacttgg ccggcaaagc cacagcggaa   180
agcctgtacc tgagaacccc agatgcctat gcagcgcaga catccaact actcggaggc   240 acacaggtaa cggctatcaa ccgcgaccga cagcaagtaa tcctatcgga tggccgggca   300
ctggattacg accggctggt attggctacc ggagggcgtc caagaccccct accggtggcc   360 agtggcgcag ttggaaaggc gaacaacttt cgatacctgc gcacactcga ggacgccgag   420
tgcattcgcc ggcagctgat tgcggataac cgtctggtgg tgattggtgg cggctacatt   480
ggccttgaag tggctgccac cgccatcaag gcgaacatgc acgtcaccct gcttgatacg   540
gcagcccggg ttctggagcg ggttaccgcc ccgccggtat cggccttta cgagcaccta   600
```

-continued

```
caccgcgaag ccggcgttga catacgaacc ggcacgcagg tgtgcgggtt cgagatgtcg      660
accgaccaac agaaggttac cgccgtcctc tgcgaggacg cacaaggct gccagcggat       720 ctggtaatcg ccgggattgg cctgatacca aactgcgagt tggccagtgc ggccggcctg     780
caggttgata acggcatcgt gatcaacgaa acatgcaga cctctgatcc cttgatcatg      840
gccgtcggcg actgtgcccg atttcacagt cagctctatg accgctgggt gcgtatcgaa     900
tcggtgccca atgccttgga gcaggcacga agatcgccg ccatcctctg tggcaaggtg      960
ccacgcgatg aggcggcgcc ctggttctgg tccgatcagt atgagatcgg attgaagatg    1020
gtcggactgt ccgaagggta cgaccggatc attgtccgcg gctctttggc gcaacccgac    1080
ttcagcgttt tctacctgca gggagaccgg gtattggcgg tcgatacagt gaaccgtcca    1140
gtggagttca accagtcaaa acaaataatc acggatcgtt tgccggttga accaaaccta    1200
ctcggtgacg aaagcgtgcc gttaaaggaa atcatcgccg ccgcaaagc tgaactgagt     1260 agtgcctgaa atctataccc acaataaatc accgttttgc cccatagcgt gtgaggataa    1320
acagatgtct aaagtagtgt atgtgtcaca tgatggaacg cgtcgcgaac tggatgtggc    1380
ggatggcgtc agcctgatgc aggctgcagt ctccaatggt atctacgata ttgtcggtga    1440
ttgtggcggc agcgccagct gtgccacctg ccatgtctat gtgaacgaag cgttcacgga    1500
caaggtgccc gccgccaacg agcgggaaat cggcatgctg gagtgcgtca cggccgaact    1560
gaagccgaac agcaggctct gctgccagat catcatgacg cccgagctgg atggcatcgt    1620
ggtcgatgtt cccgataggc aatggtaa                                        1648
```

<210> SEQ ID NO 15
<211> LENGTH: 422
<212> TYPE: PRT
<213> ORGANISM: Pseudomonas putida

<400> SEQUENCE: 15

```
Met Asn Ala Asn Asp Asn Val Val Ile Val Gly Thr Gly Leu Ala Gly
1               5                   10                  15

Val Glu Val Ala Phe Gly Leu Arg Ala Ser Gly Trp Glu Gly Asn Ile
            20                  25                  30

Arg Leu Val Gly Asp Ala Thr Val Ile Pro His His Leu Pro Pro Leu
        35                  40                  45

Ser Lys Ala Tyr Leu Ala Gly Lys Ala Thr Ala Glu Ser Leu Tyr Leu
    50                  55                  60

Arg Thr Pro Asp Ala Tyr Ala Ala Gln Asn Ile Gln Leu Leu Gly Gly
65                  70                  75                  80

Thr Gln Val Thr Ala Ile Asn Arg Asp Arg Gln Gln Val Ile Leu Ser
                85                  90                  95

Asp Gly Arg Ala Leu Asp Tyr Asp Arg Leu Val Leu Ala Thr Gly Gly
            100                 105                 110

Arg Pro Arg Pro Leu Pro Val Ala Ser Gly Ala Val Gly Lys Ala Asn
        115                 120                 125

Asn Phe Arg Tyr Leu Arg Thr Leu Glu Asp Ala Glu Cys Ile Arg Arg
    130                 135                 140

Gln Leu Ile Ala Asp Asn Arg Leu Val Val Ile Gly Gly Gly Tyr Ile
145                 150                 155                 160

Gly Leu Glu Val Ala Ala Thr Ala Ile Lys Ala Asn Met His Val Thr
                165                 170                 175

Leu Leu Asp Thr Ala Ala Arg Val Leu Glu Arg Val Thr Ala Pro Pro
```

180                 185                 190
Val Ser Ala Phe Tyr Glu His Leu His Arg Glu Ala Gly Val Asp Ile
            195                 200                 205
Arg Thr Gly Thr Gln Val Cys Gly Phe Glu Met Ser Thr Asp Gln Gln
    210                 215                 220
Lys Val Thr Ala Val Leu Cys Glu Asp Gly Thr Arg Leu Pro Ala Asp
225                 230                 235                 240
Leu Val Ile Ala Gly Ile Gly Leu Ile Pro Asn Cys Glu Leu Ala Ser
                245                 250                 255
Ala Ala Gly Leu Gln Val Asp Asn Gly Ile Val Ile Asn Glu His Met
            260                 265                 270
Gln Thr Ser Asp Pro Leu Ile Met Ala Val Gly Asp Cys Ala Arg Phe
        275                 280                 285
His Ser Gln Leu Tyr Asp Arg Trp Val Arg Ile Glu Ser Val Pro Asn
    290                 295                 300
Ala Leu Glu Gln Ala Arg Lys Ile Ala Ala Ile Leu Cys Gly Lys Val
305                 310                 315                 320
Pro Arg Asp Glu Ala Ala Pro Trp Phe Trp Ser Asp Gln Tyr Glu Ile
                325                 330                 335
Gly Leu Lys Met Val Gly Leu Ser Glu Gly Tyr Asp Arg Ile Ile Val
            340                 345                 350
Arg Gly Ser Leu Ala Gln Pro Asp Phe Ser Val Phe Tyr Leu Gln Gly
        355                 360                 365
Asp Arg Val Leu Ala Val Asp Thr Val Asn Arg Pro Val Glu Phe Asn
    370                 375                 380
Gln Ser Lys Gln Ile Ile Thr Asp Arg Leu Pro Val Glu Pro Asn Leu
385                 390                 395                 400
Leu Gly Asp Glu Ser Val Pro Leu Lys Glu Ile Ala Ala Ala Lys
                405                 410                 415
Ala Glu Leu Ser Ser Ala
            420

<210> SEQ ID NO 16
<211> LENGTH: 107
<212> TYPE: PRT
<213> ORGANISM: Pseudomonas putida

<400> SEQUENCE: 16

Met Ser Lys Val Val Tyr Val Ser His Asp Gly Thr Arg Arg Glu Leu
1               5                   10                  15
Asp Val Ala Asp Gly Val Ser Leu Met Gln Ala Ala Val Ser Asn Gly
            20                  25                  30
Ile Tyr Asp Ile Val Gly Asp Cys Gly Gly Ser Ala Ser Cys Ala Thr
        35                  40                  45
Cys His Val Tyr Val Asn Glu Ala Phe Thr Asp Lys Val Pro Ala Ala
    50                  55                  60
Asn Glu Arg Glu Ile Gly Met Leu Glu Cys Val Thr Ala Glu Leu Lys
65                  70                  75                  80
Pro Asn Ser Arg Leu Cys Cys Gln Ile Ile Met Thr Pro Glu Leu Asp
                85                  90                  95
Gly Ile Val Val Asp Val Pro Asp Arg Gln Trp
            100                 105

<210> SEQ ID NO 17
<211> LENGTH: 52

<212> TYPE: DNA
<213> ORGANISM: Artificial Sequence
<220> FEATURE:
<223> OTHER INFORMATION: forward primer

<400> SEQUENCE: 17
gtaaaaaatg tctcatatgg gcggcgaatt catgaacgca aacgacaacg tg         52

<210> SEQ ID NO 18
<211> LENGTH: 46
<212> TYPE: DNA
<213> ORGANISM: Artificial Sequence
<220> FEATURE:
<223> OTHER INFORMATION: reverse primer

<400> SEQUENCE: 18
gtgagacctc aaccgcggcc gctcattacc attgcctatc gggaac                46

<210> SEQ ID NO 19
<211> LENGTH: 52
<212> TYPE: DNA
<213> ORGANISM: Artificial Sequence
<220> FEATURE:
<223> OTHER INFORMATION: forward primer

<400> SEQUENCE: 19
attttgttta actttaagaa ggagatatac atatgactga cgtcgaggaa ac         52

<210> SEQ ID NO 20
<211> LENGTH: 66
<212> TYPE: DNA
<213> ORGANISM: Artificial Sequence
<220> FEATURE:
<223> OTHER INFORMATION: reverse primer

<400> SEQUENCE: 20
gacgatgacc acgttgtcgt ttgcgttcat gaattctgtt tcctataatt accaggtgac   60
cggaag                                                              66

<210> SEQ ID NO 21
<211> LENGTH: 30
<212> TYPE: DNA
<213> ORGANISM: Artificial Sequence
<220> FEATURE:
<223> OTHER INFORMATION: forward primer

<400> SEQUENCE: 21
tctcatatga ctgacgtcga ggaaaccacc                                    30

<210> SEQ ID NO 22
<211> LENGTH: 79
<212> TYPE: DNA
<213> ORGANISM: Artificial Sequence
<220> FEATURE:
<223> OTHER INFORMATION: reverse primer

<400> SEQUENCE: 22
ctgttcagtg ctaggtgaag gaatgctgcc gccgctgccg ccgctgccgc cccaggtgac   60
cggaagggcg tggaggccg                                                79

<210> SEQ ID NO 23
<211> LENGTH: 1821
<212> TYPE: DNA
<213> ORGANISM: Artificial Sequence
<220> FEATURE:

<223> OTHER INFORMATION: Coding sequence subcloned into plasmid

<400> SEQUENCE: 23

```
catatgataa tacgccggcg gcagcggcgg cagcattcct tcacctagca ctgaacagtc    60
tgctaaaaaa gtacgcaaaa aggcagaaaa cgctcataat acgccgctgc ttgtgctata   120
cggttcaaat atgggaacag ctgaaggaac ggcgcgtgat ttagcagata ttgcaatgag   180
caaaggattt gcaccgcagg tcgcaacgct tgattcacac gccggaaatc ttccgcgcga   240
aggagctgta ttaattgtaa cggcgtctta taacggtcat ccgcctgata acgcaaagca   300
atttgtcgac tggttagacc aagcgtctgc tgatgaagta aaaggcgttc gctactccgt   360
atttggatgc ggcgataaaa actgggctac tacgtatcaa aaagtgcctg ctttatcga   420
tgaaacgctt gccgctaaag gggcagaaaa catcgctgac cgcggtgaag cagatgcaag   480
cgacgacttt gaaggcacat acgaagaatg gcgtgaacac atgtggagtg acgtagcagc   540
ctactttaac ctcgacattg aaacagtga agataataaa tctactcttt cacttcaatt   600
tgtcgacagc gccgcggata tgccgcttgc gaaaatgcac ggtgcgtttt caacgaacgt   660
cgtagcaagc aaagaacttc aacagccagg cagtgcacga agcacgcgac atcttgaaat   720
tgaacttcca aaagaagctt cttatcaaga aggagatcat ttaggtgtta ttcctcgcaa   780
ctatgaagga atagtaaacc gtgtaacagc aaggttcggc tagatgcat cacagcaaat   840
ccgtctggaa gcagaagaag aaaaattagc tcatttgcca ctcgctaaaa cagtatccgt   900
agaagagctt ctgcaatacg tggagcttca agatcctgtt acgcgcacgc agcttcgcgc   960
aatggctgct aaaacggtct gcccgccgca taaagtagag cttgaagcct tgcttgaaaa  1020
gcaagcctac aaagaacaag tgctggcaaa acgtttaaca atgcttgaac tgcttgaaaa  1080
atacccggcg tgtgaaatga attcagcga atttatcgcc cttctgccaa gcatacgccc  1140
gcgctattac tcgatttctt catcacctcg tgtcgatgaa aaacaagcaa gcatcacggt  1200
cagcgttgtc tcaggagaag cgtggagcgg atatggagaa tataaaggaa ttgcgtcgaa  1260
ctatcttgcc gagctgcaag aaggagatac gattacgtgc tttatttcca caccgcagtc  1320
agaatttacg ctgccaaaag accctgaaac gccgcttatc atggtcggac cgggaacagg  1380
cgtcgcgccg tttagaggct tgtgcaggc gcgcaaacag ctaaaagaac aaggacagtc  1440
acttggagaa gcacatttat acttcggctg ccgttcacct catgaagact atctgtatca  1500
agaagagctt gaaacgcccc aaagcgaagg catcattacg cttcataccg cttttttctcg  1560
catgccaaat cagccgaaaa catacgttca gcacgtaatg aacaagacg gcaagaaatt  1620
gattgaactt cttgatcaag gagcgcactt ctatatttgc ggagacggaa gccaaatggc  1680
acctgccgtt gaagcaacgc ttatgaaaag ctatgctgac gttcaccaag tgagtgaagc  1740
agacgctcgc ttatggctgc agcagctaga agaaaaaggc cgatacgcaa aagacgtgtg  1800
ggctgggtaa tgagcggccg c                                            1821
```

<210> SEQ ID NO 24
<211> LENGTH: 596
<212> TYPE: PRT
<213> ORGANISM: Bacillus megaterium

<400> SEQUENCE: 24

```
Gly Ser Gly Gly Ser Ile Pro Ser Pro Ser Thr Glu Gln Ser Ala Lys
1               5                   10                  15

Lys Val Arg Lys Lys Ala Glu Asn Ala His Asn Thr Pro Leu Leu Val
            20                  25                  30
```

-continued

```
Leu Tyr Gly Ser Asn Met Gly Thr Ala Glu Gly Thr Ala Arg Asp Leu
            35                  40                  45

Ala Asp Ile Ala Met Ser Lys Gly Phe Ala Pro Gln Val Ala Thr Leu
 50                  55                  60

Asp Ser His Ala Gly Asn Leu Pro Arg Glu Gly Ala Val Leu Ile Val
 65                  70                  75                  80

Thr Ala Ser Tyr Asn Gly His Pro Pro Asp Asn Ala Lys Gln Phe Val
                85                  90                  95

Asp Trp Leu Asp Gln Ala Ser Ala Asp Glu Val Lys Gly Val Arg Tyr
                100                 105                 110

Ser Val Phe Gly Cys Gly Asp Lys Asn Trp Ala Thr Thr Tyr Gln Lys
                115                 120                 125

Val Pro Ala Phe Ile Asp Glu Thr Leu Ala Ala Lys Gly Ala Glu Asn
        130                 135                 140

Ile Ala Asp Arg Gly Glu Ala Asp Ala Ser Asp Asp Phe Glu Gly Thr
145                 150                 155                 160

Tyr Glu Glu Trp Arg Glu His Met Trp Ser Asp Val Ala Ala Tyr Phe
                165                 170                 175

Asn Leu Asp Ile Glu Asn Ser Glu Asp Asn Lys Ser Thr Leu Ser Leu
                180                 185                 190

Gln Phe Val Asp Ser Ala Ala Asp Met Pro Leu Ala Lys Met His Gly
        195                 200                 205

Ala Phe Ser Thr Asn Val Val Ala Ser Lys Glu Leu Gln Gln Pro Gly
        210                 215                 220

Ser Ala Arg Ser Thr Arg His Leu Glu Ile Glu Leu Pro Lys Glu Ala
225                 230                 235                 240

Ser Tyr Gln Glu Gly Asp His Leu Gly Val Ile Pro Arg Asn Tyr Glu
                245                 250                 255

Gly Ile Val Asn Arg Val Thr Ala Arg Phe Gly Leu Asp Ala Ser Gln
                260                 265                 270

Gln Ile Arg Leu Glu Ala Glu Glu Lys Leu Ala His Leu Pro Leu
        275                 280                 285

Ala Lys Thr Val Ser Val Glu Glu Leu Leu Gln Tyr Val Glu Leu Gln
        290                 295                 300

Asp Pro Val Thr Arg Thr Gln Leu Arg Ala Met Ala Ala Lys Thr Val
305                 310                 315                 320

Cys Pro Pro His Lys Val Glu Leu Glu Ala Leu Leu Glu Lys Gln Ala
                325                 330                 335

Tyr Lys Glu Gln Val Leu Ala Lys Arg Leu Thr Met Leu Glu Leu Leu
                340                 345                 350

Glu Lys Tyr Pro Ala Cys Glu Met Lys Phe Ser Glu Phe Ile Ala Leu
                355                 360                 365

Leu Pro Ser Ile Arg Pro Arg Tyr Tyr Ser Ile Ser Ser Ser Pro Arg
        370                 375                 380

Val Asp Glu Lys Gln Ala Ser Ile Thr Val Ser Val Val Ser Gly Glu
385                 390                 395                 400

Ala Trp Ser Gly Tyr Gly Glu Tyr Lys Gly Ile Ala Ser Asn Tyr Leu
                405                 410                 415

Ala Glu Leu Gln Glu Gly Asp Thr Ile Thr Cys Phe Ile Ser Thr Pro
                420                 425                 430

Gln Ser Glu Phe Thr Leu Pro Lys Asp Pro Glu Thr Pro Leu Ile Met
        435                 440                 445
```

```
Val Gly Pro Gly Thr Gly Val Ala Pro Phe Arg Gly Phe Val Gln Ala
    450                 455                 460
Arg Lys Gln Leu Lys Glu Gln Gly Gln Ser Leu Gly Glu Ala His Leu
465                 470                 475                 480
Tyr Phe Gly Cys Arg Ser Pro His Glu Asp Tyr Leu Tyr Gln Glu Glu
                485                 490                 495
Leu Glu Asn Ala Gln Ser Glu Gly Ile Ile Thr Leu His Thr Ala Phe
                500                 505                 510
Ser Arg Met Pro Asn Gln Pro Lys Thr Tyr Val Gln His Val Met Glu
            515                 520                 525
Gln Asp Gly Lys Lys Leu Ile Glu Leu Leu Asp Gln Gly Ala His Phe
530                 535                 540
Tyr Ile Cys Gly Asp Gly Ser Gln Met Ala Pro Ala Val Glu Ala Thr
545                 550                 555                 560
Leu Met Lys Ser Tyr Ala Asp Val His Gln Val Ser Glu Ala Asp Ala
                565                 570                 575
Arg Leu Trp Leu Gln Gln Leu Glu Glu Lys Gly Arg Tyr Ala Lys Asp
                580                 585                 590
Val Trp Ala Gly
        595
```

<210> SEQ ID NO 25
<211> LENGTH: 3015
<212> TYPE: DNA
<213> ORGANISM: Artificial Sequence
<220> FEATURE:
<223> OTHER INFORMATION: Fusion protein coding sequence

<400> SEQUENCE: 25

```
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgccccctc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgcccgtt ccctcgctgg tgatctgcga actgctcggc     480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa acggcgacct cacgcttcgc cacggcggac     900
gtcgagatcg gcggaacgct gatccgcgcg gggaaggggg tggtgggcct gagcaacgcg     960
ggcaaccacg atccggacgg cttcgagaac ccggacacct cgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgcccct    1200
```

-continued

```
ccggtcacct gggcggcag cggcggcagc ggcggcagca ttccttcacc tagcactgaa    1260
cagtctgcta aaaagtacg caaaaaggca gaaaacgctc ataatacgcc gctgcttgtg    1320
ctatacggtt caaatatggg aacagctgaa ggaacggcgc gtgatttagc agatattgca    1380
atgagcaaag gatttgcacc gcaggtcgca acgcttgatt cacacgccgg aaatcttccg    1440
cgcgaaggag ctgtattaat tgtaacggcg tcttataacg gtcatccgcc tgataacgca    1500
aagcaatttg tcgactggtt agaccaagcg tctgctgatg aagtaaaagg cgttcgctac    1560
tccgtatttg gatgcggcga taaaaactgg gctactacgt atcaaaaagt gcctgctttt    1620
atcgatgaaa cgcttgccgc taaggggca gaaaacatcg ctgaccgcgg tgaagcagat    1680
gcaagcgacg actttgaagg cacatacgaa gaatggcgtg aacacatgtg gagtgacgta    1740
gcagcctact ttaacctcga cattgaaaac agtgaagata taaatctac tctttcactt     1800 caatttgtcg acagcgccgc ggatatgccg cttgcgaaaa tgcacggtgc gttttcaacg    1860
aacgtcgtag caagcaaaga acttcaacag ccaggcagtg cacgaagcac gcgacatctt    1920
gaaattgaac ttccaaaaga agcttcttat caagaaggag atcatttagg tgttattcct    1980
cgcaactatg aaggaatagt aaaccgtgta acagcaaggt tcggcctaga tgcatcacag    2040
caaatccgtc tggaagcaga agaagaaaaa ttagctcatt gccactcgc taaaacagta    2100 tccgtagaag agcttctgca atacgtggag cttcaagatc ctgttacgcg cacgcagctt    2160
cgcgcaatgg ctgctaaaac ggtctgcccg ccgcataaag tagagcttga agccttgctt    2220
gaaaagcaag cctacaaaga acaagtgctg gcaaaacgtt taacaatgct tgaactgctt    2280
gaaaaatacc cggcgtgtga aatgaaattc agcgaattta tcgcccttct gccaagcata    2340
cgcccgcgct attactcgat ttcttcatca cctcgtgtcg atgaaaaaca agcaagcatc    2400
acggtcagcg ttgtctcagg agaagcgtgg agcggatatg gagaatataa aggaattgcg    2460
tcgaactatc ttgccgagct gcaagaagga gatacgatta cgtgctttat ttccacaccg    2520
cagtcagaat ttacgctgcc aaaagaccct gaaacgccgc ttatcatggt cggaccggga    2580
acaggcgtcg cgccgtttag aggctttgtg caggcgcgca acagctaaa agaacaagga    2640 cagtcacttg gagaagcaca tttatacttc ggctgccgtt cacctcatga agactatctg    2700
tatcaagaag agcttgaaaa cgcccaaagc gaaggcatca ttacgcttca taccgctttt    2760
tctcgcatgc caaatcagcc gaaaacatac gttcagcacg taatgaaaca agacggcaag    2820
aaattgattg aacttcttga tcaaggagcg cacttctata tttgcggaga cggaagccaa    2880
atggcacctg ccgttgaagc aacgcttatg aaaagctatg ctgacgttca ccaagtgagt    2940
gaagcagacg ctcgcttatg gctgcagcag ctagaagaaa aaggccgata cgcaaaagac    3000
gtgtgggctg ggtaa                                                    3015
```

<210> SEQ ID NO 26
<211> LENGTH: 1004
<212> TYPE: PRT
<213> ORGANISM: Artificial Sequence
<220> FEATURE:
<223> OTHER INFORMATION: Fusion protein

<400> SEQUENCE: 26

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
            35                  40                  45

Thr Arg Leu Glu Asp Ile Arg Glu Met Leu Ser Ser Pro His Phe Ser
 50                  55                  60

Ser Asp Arg Gln Ser Pro Ser Phe Pro Leu Met Val Ala Arg Gln Ile
 65                  70                  75                  80

Arg Arg Glu Asp Lys Pro Phe Arg Pro Ser Leu Ile Ala Met Asp Pro
                 85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Thr Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp Gly Ser Gly Gly Ser Gly Gly Ser Ile Pro Ser
                405                 410                 415

Pro Ser Thr Glu Gln Ser Ala Lys Lys Val Arg Lys Lys Ala Glu Asn
            420                 425                 430

Ala His Asn Thr Pro Leu Leu Val Leu Tyr Gly Ser Asn Met Gly Thr
        435                 440                 445

Ala Glu Gly Thr Ala Arg Asp Leu Ala Asp Ile Ala Met Ser Lys Gly

```
            450                 455                 460
    Phe Ala Pro Gln Val Ala Thr Leu Asp Ser His Ala Gly Asn Leu Pro
    465                 470                 475                 480

Arg Glu Gly Ala Val Leu Ile Val Thr Ala Ser Tyr Asn Gly His Pro
                        485                 490                 495

Pro Asp Asn Ala Lys Gln Phe Val Asp Trp Leu Asp Gln Ala Ser Ala
                    500                 505                 510

Asp Glu Val Lys Gly Val Arg Tyr Ser Val Phe Gly Cys Gly Asp Lys
                515                 520                 525

Asn Trp Ala Thr Thr Tyr Gln Lys Val Pro Ala Phe Ile Asp Glu Thr
    530                 535                 540

Leu Ala Ala Lys Gly Ala Glu Asn Ile Ala Asp Arg Gly Glu Ala Asp
    545                 550                 555                 560

Ala Ser Asp Asp Phe Glu Gly Thr Tyr Glu Glu Trp Arg Glu His Met
                        565                 570                 575

Trp Ser Asp Val Ala Ala Tyr Phe Asn Leu Asp Ile Glu Asn Ser Glu
                    580                 585                 590

Asp Asn Lys Ser Thr Leu Ser Leu Gln Phe Val Asp Ser Ala Ala Asp
                595                 600                 605

Met Pro Leu Ala Lys Met His Gly Ala Phe Ser Thr Asn Val Val Ala
    610                 615                 620

Ser Lys Glu Leu Gln Gln Pro Gly Ser Ala Arg Ser Thr Arg His Leu
    625                 630                 635                 640

Glu Ile Glu Leu Pro Lys Glu Ala Ser Tyr Gln Glu Gly Asp His Leu
                        645                 650                 655

Gly Val Ile Pro Arg Asn Tyr Glu Gly Ile Val Asn Arg Val Thr Ala
                    660                 665                 670

Arg Phe Gly Leu Asp Ala Ser Gln Gln Ile Arg Leu Glu Ala Glu Glu
                675                 680                 685

Glu Lys Leu Ala His Leu Pro Leu Ala Lys Thr Val Ser Val Glu Glu
    690                 695                 700

Leu Leu Gln Tyr Val Glu Leu Gln Asp Pro Val Thr Arg Thr Gln Leu
    705                 710                 715                 720

Arg Ala Met Ala Ala Lys Thr Val Cys Pro Pro His Lys Val Glu Leu
                        725                 730                 735

Glu Ala Leu Leu Glu Lys Gln Ala Tyr Lys Glu Gln Val Leu Ala Lys
                    740                 745                 750

Arg Leu Thr Met Leu Glu Leu Leu Glu Lys Tyr Pro Ala Cys Glu Met
                755                 760                 765

Lys Phe Ser Glu Phe Ile Ala Leu Leu Pro Ser Ile Arg Pro Arg Tyr
    770                 775                 780

Tyr Ser Ile Ser Ser Ser Pro Arg Val Asp Glu Lys Gln Ala Ser Ile
    785                 790                 795                 800

Thr Val Ser Val Val Ser Gly Glu Ala Trp Ser Gly Tyr Gly Glu Tyr
                        805                 810                 815

Lys Gly Ile Ala Ser Asn Tyr Leu Ala Glu Leu Gln Glu Gly Asp Thr
                    820                 825                 830

Ile Thr Cys Phe Ile Ser Thr Pro Gln Ser Glu Phe Thr Leu Pro Lys
                835                 840                 845

Asp Pro Glu Thr Pro Leu Ile Met Val Gly Pro Gly Thr Gly Val Ala
    850                 855                 860

Pro Phe Arg Gly Phe Val Gln Ala Arg Lys Gln Leu Lys Glu Gln Gly
    865                 870                 875                 880
```

```
Gln Ser Leu Gly Glu Ala His Leu Tyr Phe Gly Cys Arg Ser Pro His
            885             890                 895

Glu Asp Tyr Leu Tyr Gln Glu Glu Leu Glu Asn Ala Gln Ser Glu Gly
            900             905                 910

Ile Ile Thr Leu His Thr Ala Phe Ser Arg Met Pro Asn Gln Pro Lys
            915             920                 925

Thr Tyr Val Gln His Val Met Glu Gln Asp Gly Lys Lys Leu Ile Glu
        930             935             940

Leu Leu Asp Gln Gly Ala His Phe Tyr Ile Cys Gly Asp Gly Ser Gln
945             950             955             960

Met Ala Pro Ala Val Glu Ala Thr Leu Met Lys Ser Tyr Ala Asp Val
                965             970             975

His Gln Val Ser Glu Ala Asp Ala Arg Leu Trp Leu Gln Gln Leu Glu
            980             985             990

Glu Lys Gly Arg Tyr Ala Lys Asp  Val Trp Ala Gly
        995             1000
```